(12) United States Patent
Gellerfors et al.

(10) Patent No.: US 6,537,777 B1
(45) Date of Patent: Mar. 25, 2003

(54) HUMAN PORPHOBILINOGEN DEAMINASE SEQUENCES

(75) Inventors: Par Gellerfors, Lidingo (SE); Jens Fogh, Lynge (DK)

(73) Assignee: Hemebiotech A/S, Hillerod (DK)

( * ) Notice: Subject to any disclaimer, the term of this patent is extended or adjusted under 35 U.S.C. 154(b) by 0 days.

(21) Appl. No.: 09/358,856

(22) Filed: Jul. 22, 1999

Related U.S. Application Data

(60) Provisional application No. 60/094,258, filed on Jul. 27, 1998.

(51) Int. Cl.⁷ .......................... C12P 21/06; C12P 21/04; C12N 1/20; C07H 21/04
(52) U.S. Cl. .................... 435/69.1; 435/70.1; 435/71.1; 435/252.3; 536/23.1; 536/23.5
(58) Field of Search ............................ 536/23.1, 23.4, 536/23.5; 435/325, 252.3, 254.11, 254.2, 18.3, 69.1, 70.1, 71.1; 530/412

(56) References Cited

FOREIGN PATENT DOCUMENTS

WO          9937325          7/1999

OTHER PUBLICATIONS

PD Brownlie et al., Protein Science, "The three-dimensional structures of mutants of porphobilingen deaminase: Toward an understanding of the structural basis of acute intermittent porphyria," 1994, 3: 1644–1650.*

GV Louie et al., Nature, "Structure of porphobilinogen deaminase reveals a flexible multidomain polymerase with a single catalytic site," Sep. 1992, vol. 359, pp. 33–39.*

Ludish, et al., Molecular Cell Biology (Third Edition), 1995 by Scientific American Books, Inc. pp. 299–300.

* cited by examiner

Primary Examiner—Deborah Crouch
Assistant Examiner—Joseph Woitach
(74) Attorney, Agent, or Firm—Iver P. Cooper

(57) ABSTRACT

A method for treatment or prophylaxis of disease caused by deficiency, in a subject, of an enzyme belonging to the heme biosynthetic pathway, the method comprising administering, to the subject, an effective amount of a catalyst which is an enzyme or an enzymatically equivalent part or analogue thereof. The disease is selected from the group consisting of acute intermittent porphyria (AIP), ALA deficiency porphyria (ADP), Porphyria cutanea tarda (PCT), Hereditary coproporphyria (HCP), Harderoporphyria (HDP), Variegata prophyria (VP), Congenital erthropoetic porphyria (CEP), Erythropoietic protoporphyria (EPP), and Hepatoerythropoietic porphyria (HEP). The catalyst is one or more enzymes selected from the group consisting of delta-aminolevulininic acid synthetase, delta-aminolevulinic acid dehydratase (ALAD), porphobilinogen deaminase (PBGD), uroporphyrinogen III cosythetase, uroporphyrinogen decarboxylase, coproporphyrinogen oxidase, protoporphyrinogen oxidase, and ferrochelatase, or an enzymatically equivalent part or analogue thereof. In addition the invention relates to the use of PBGD, to human recombinant PBGD and to a method of gene therapy. The invention also relates to an expression plasmid pExp1-M2-BB (Seq. ID No. 1) and to use of a DNA fragment, the EcoRI-Hind III linear fragment (seq. ID No. 2), used for transformation in the hemC disruption strategy for production of rhPBGD expressed in *E. coli*.

13 Claims, 22 Drawing Sheets

SEQUENCE LISTING

<160> NUMBER OF SEQ ID NOS: 40

<210> SEQ ID NO 1
<211> LENGTH: 5446
<212> TYPE: DNA
<213> ORGANISM: Artificial Sequence
<220> FEATURE:
<223> OTHER INFORMATION: Sequence of the expression plasmid pExp1-M2-BB

<400> SEQUENCE: 1

```
gaattctaac ataagttaag gaggaaaaaa aaatgagagt tattcgtgtc ggtacccgca       60
agagccagct tgctcgcata cagacggaca gtgtggtggc aacattgaaa gcctcgtacc      120
ctggcctgca gtttgaaatc attgctatgt ccaccacagg ggacaagatt cttgatactg      180
cactctctaa gattggagag aaaagcctgt ttaccaagga gcttgaacat gccctggaga      240
agaatgaagt ggacctggtt gttcactcct tgaaggacct gcccactgtg cttcctcctg      300
gcttcaccat cggagccatc tgcaagcggg aaaaccctca tgatgctgtt gtctttcacc      360
caaaatttgt tgggaagacc ctagaaaccc tgccagagaa gagtgtggtg ggaaccagct      420
ccctgcgaag agcagcccag ctgcagagaa agttcccgca tctggagttc aggagtattc      480
ggggaaacct caacacccgg cttcggaagc tggacgagca gcaggagttc agtgccatca      540
tcctggcaac agctggcctg cagcgcatgg gctggcacaa ccgggttggg cagatcctgc      600
accctgagga atgcatgtat gctgtgggcc aggggccttt gggcgtggaa gtgcgagcca      660
aggaccagga catcttggat ctggtgggtg tgctgcacga tcccgagact ctgcttcgct      720
gcatcgctga aagggccttc ctgaggcacc tggaaggagg ctgcagtgtg ccagtagccg      780
tgcatacagc tatgaaggat gggcaactgt acctgactgg aggagtctgg agtctagacg      840
gctcagatag catacaagag accatgcagg ctaccatcca tgtccctgcc cagcatgaag      900
atggccctga ggatgaccca cagttggtag gcatcactgc tcgtaacatt ccacgagggc      960
cccagttggc tgcccagaac ttgggcatca gcctggccaa cttgttgctg agcaaaggag     1020
```

```
ccaaaaacat cctggatgtt gcacggcaat tgaacgatgc ccattaataa gcttggctgt    1080
tttggcggat gagagaagat tttcagcctg atacagatta aatcagaacg cagaagcggt    1140
ctgataaaac agaatttgcc tggcggcagt agcgcggtgg tcccacctga ccccatgccg    1200
aactcagaag tgaaacgccg tagcgccgat ggtagtgtgg ggtctcccca tgcgagagta    1260
gggaactgcc aggcatcaaa taaaacgaaa ggctcagtcg aaagactggg cctttcgttt    1320
tatctgttgt ttgtcggtga acgctctcct gagtaggaca atccgccgg gagcggattt    1380 gaacgttgcg aagcaacggc ccggagggtg cgggcagga cgcccgccat aaactgccag    1440
gcatcaaatt aagcagaagg ccatcctgac ggatggcctt tttgcgtttc tacaaactct    1500
tttgtttatt tttctaaata cattcaaata tgtatccgct catgagacaa taaccctgat    1560
aaatgcttca ataatattga aaaggaaga gtatgagtat tcaacatttc cgtgtcgccc    1620
ttattccctt ttttgcggca ttttgccttc ctgttttttgc tcacccagaa acgctggtga    1680
aagtaaaaga tgctgaagat cagttgggtg cacgagtggg ttacatcgaa ctggatctca    1740
acagcggtaa gatccttgag agttttcgcc ccgaagaacg ttttccaatg atgagcactt    1800
ttaaagttct gctatgtggc gcggtattat cccgtgttga cgccgggcaa gagcaactcg    1860
gtcgccgcat acactattct cagaatgact tggttgagta ctcaccagtc acagaaaagc    1920
atcttacgga tggcatgaca gtaagagaat tatgcagtgc tgccataacc atgagtgata    1980
acactgcggc caacttactt ctgacaacga tcggaggacc gaaggagcta accgcttttt    2040
tgcacaacat gggggatcat gtaactcgcc ttgatcgttg ggaaccggag ctgaatgaag    2100
ccataccaaa cgacgagcgt gacaccacga tgcctgtagc aatggcaaca acgttgcgca    2160
aactattaac tggcgaacta cttactctag cttcccggca acaattaata gactggatgg    2220
aggcggataa agttgcagga ccacttctgc gctcggccct tccggctggc tggtttattg    2280
ctgataaatc tggagccggt gagcgtgggt ctcgcggtat cattgcagca ctggggccag    2340
atggtaagcc ctcccgtatc gtagttatct acacgacggg gagtcaggca actatggatg    2400
aacgaaatag acagatcgct gagataggtg cctcactgat taagcattgg taactgtcag    2460
accaagttta ctcatatata ctttagattg atttaaaact tcattttaa tttaaaagga    2520 tctaggtgaa gatccttttt gataatctca tgaccaaaat cccttaacgt gagttttcgt    2580
tccactgagc gtcagacccc gtagaaaaga tcaaggatc ttcttgagat cctttttttc    2640
tgcgcgtaat ctgctgcttg caaacaaaaa aaccaccgct accagcggtg gtttgtttgc    2700
cggatcaaga gctaccaact cttttttccga aggtaactgg cttcagcaga gcgcagatac    2760
caaatactgt ccttctagtg tagccgtagt taggccacca cttcaagaac tctgtagcac    2820
cgcctacata cctcgctctg ctaatcctgt taccagtggc tgctgccagt ggcgataagt    2880
cgtgtcttac cgggttggac tcaagacgat agttaccgga taaggcgcag cggtcgggct    2940
gaacgggggg ttcgtgcaca gcccagctt ggagcgaac gacctacacc gaactgagat    3000
acctacagcg tgagctatga gaaagcgcca cgcttcccga aggagaaag gcggacaggt    3060 atccggtaag cggcagggtc ggaacaggag agcgcacgag ggagcttcca gggggaaacg    3120
cctggtatct ttatagtcct gtcgggtttc gccacctctg acttgagcgt cgatttttgt    3180
gatgctcgtc aggggggcgg agcctatgga aaaacgccag caacgcggcc ttttacggt    3240 tcctggcctt ttgctggcct tttgctcaca tgttctttcc tgcgttatcc cctgattctg    3300
tggataaccg tattaccgcc tttgagtgag ctgataccgc tcgccgcagc cgaacgaccg    3360
agcgcagcga gtcagtgagc gaggaagcgg aagagcgcct gatgcggtat tttctcctta    3420
```

```
cgcatctgtg cggtatttca caccgcatat ggtgcactct cagtacaatc tgctctgatg    3480
ccgcatagtt aagccagtat acactccgct atcgctacag atccggaaca taatggtgca    3540
gggcgctgac ttccgcgttt ccagacttta cgaaacacgg aaaccgaaga ccattcatgt    3600
tgttgctcag gtcgcagacg ttttgcagca gcagtcgctt cacgttcgct cgcgtatcgg    3660
tgattcattc tgctaaccag taaggcaacc ccgccagcct agccgggtcc tcaacgacag    3720
gagcacgatc atgcgcaccc gtggccagga cccaacgctg cccgagatgc gccgcgtgcg    3780
gctgctggag atggcggacg cgatggatat gttctgccaa gggttggttt gcgcattcac    3840
agttctccgc aagaattgat tggctccaat tcttggagtg gtgaatccgt tagcgaggtg    3900
ccgccggctt ccattcaggt cgaggtggcc cggctccatg caccgcgacg caacgcgggg    3960
aggcagacaa ggtatagggc ggcgcctaca atccatgcca acccgttcca tgtgctcgcc    4020
gaggcggcat aaatcgccgt gacgatcagc ggtccagtga tcgaagttag gctggtaaga    4080
gccgcgagcg atccttgaag ctgtccctga tggtcgtcat ctacctgcct ggacagcatg    4140
gcctgcaacg cgggcatccc gatgccgccg aagcgagaa gaatcataat ggggaaggcc    4200
atccagcctc gcgtcgcgaa cgccagcaag acgtagccca gcgcgtcggc cgccatgccg    4260
gcgataatgg cctgcttctc gccgaaacgt ttggtggcgg gaccagtgac gaaggcttga    4320
gcgagggcgt gcaagattcc gaataccgca agcgacaggc cgatcatcgt cgcgctccag    4380
cgaaagcggt cctcgccgaa aatgaccgag agcgctgccg gcacctgtcc tacgagttgc    4440
atgataaaga agacagtcat aagtgcggcg acgatagtca tgccccgcgc ccaccggaag    4500
gagctgactg ggttgaaggc tctcaagggc atcggtcgac gctctccctt atgcgactcc    4560
tgcattagga agcagcccag tagtaggttg aggccgttga gcaccgccgc cgcaaggaat    4620
ggtgcatgca aggagatggc gcccaacagt ccccggcca cggggcctgc caccataccc    4680
acgccgaaac aagcgctcat gagcccgaag tggcgagccc gatcttcccc atcggtgatg    4740
tcggcgatat aggcgccagc aaccgcacct gtggcgccgg tgatgccggc cacgatgcgt    4800
ccggcgtaga ggatccacag gacgggtgtg gtcgccatga tcgcgtagtc gatagtggct    4860
ccaagtagcg aagcgagcag gactgggcgg cggccaaagc ggtcggacag tgctccgaga    4920
acgggtgcgc atagaaattg catcaacgca tatagcgcta gcagcacgcc atagtgactg    4980
gcgatgctgt cggaatggac gatatcccgc aagaggcccg gcagtaccgg cataaccaag    5040
cctatgccta cagcatccag ggtgacggtg ccgaggatga cgatgagcgc attgttagat    5100
ttcatacacg gtgcctgact gcgttagcaa tttaactgtg ataaactacc gcattaaagc    5160
taatcgatga taagctgtca aacatgagtg atccgggctt atcgactgca cggtgcacca    5220
atgcttctgg cgtcaggcag ccatcggaag ctgtggtatg gctgtgcagg tcgtaaatca    5280
ctgcataatt cgtgtcgctc aaggcgcact cccgttctgg ataatgtttt ttgcgccgac    5340
atcataacgg ttctggcaaa tattctgaaa tgagctgttg acaattaatc atcggctcgt    5400
ataatgtgtg gaattgtgag cggataacaa tttcacacag gaaaca                  5446
```

<210> SEQ ID NO 2
<211> LENGTH: 3225
<212> TYPE: DNA
<213> ORGANISM: Artificial Sequence
<220> FEATURE:
<223> OTHER INFORMATION: Sequence of the EcoR I - Hind III linear
      fragment used for transformation in the hemC disruption strategy

<400> SEQUENCE: 2

```
aattcgtcaa gcagcagtat atgctgggtg gagccacaat cttcgccccc caggctgccg      60
ctttcattat gacggaagcg gttttcatca atcaggaaga agctgacttc cacacccagc     120
gaggcggccc agttttccag caggctacat ttacgttgta gcaattggcg ctcttcgcta     180
tcgagccagg attgatgaca gacccagata tccaggtcag aggaacaact ttgccctacg     240
gacgaggtgc tgcccatggt gtatacacca gtaattggaa gctcacctt cggcggatcc      300 tgtactgaca ttccacgata cagttcaagc tcgttcaggt agtggcgttg agtttcatca     360
ggcgtgtaaa ggcaaatgcc tttgggaacg ttaccatcaa ggtagcccgg cattagcgga     420
tggtgatagt gcaacaatgt cggcagtaga ctgtagacct gttggaatgc aggccccata     480
gcagcaagcg cgcgatccac acgcaattga tttatggcat ccagtctctg tttcagagtc     540
tcaatataga ggtacaagac gtatcgcctg atttgctacc cgtcatgact gtgattccgc     600
caacatcaac ggtaacacgc ggcattcggg atatttcgta tgtcaaaggt aaccgttacc     660
acttttcgcg cctggttttt ttagtttcac gacgaaaaaa tggtctaaaa cgtgatcaat     720
ttaacacctt gctgattgac cgtaaagaaa gatgcgctac atacaagtgt agcaccgttt     780
attctctgta aattccttat tacaacggcg tgaaacgcct gtcaggatcc actgccagac     840
ctcattttac ggtttgcgca ggcgtctacg tttcaccaca acactgacat cactctggca     900
aggatgttag gatggaccac ggatgataat gacggtaaca agcatgttag acaatgtttt     960
aagaattgcc acacgccaaa gcccacttgc actctggcag gcacactatg tcaaagacaa    1020
gttgatggcg agccatccgg gcctggtcgt tgaactggta ccgatggtga cctcgagcgg    1080
cacgtaagag gttccaactt tcaccataat gaaataagat cactaccggg cgtatttttt    1140
gagttgtcga gattttcagg agctaaggaa gctaaaatgg agaaaaaaat cactggatat    1200
accaccgttg atatatccca atggcatcgt aaagaacatt ttgaggcatt tcagtcagtt    1260
gctcaatgta cctataacca gaccgttcag ctggatatta cggcctttt aaagaccgta     1320 aagaaaaata agcacaagtt ttatccggcc tttattcaca ttcttgcccg cctgatgaat    1380
gctcatccgg aattacgtat ggcaatgaaa gacggtgagc tggtgatatg ggatagtgtt    1440 caccttgtt acaccgtttt ccatgagcaa actgaaacgt tttcatcgct ctggagtgaa    1500
taccacgacg atttccggca gtttctacac atatattcgc aagatgtggc gtgttacggt    1560
gaaaacctgg cctatttccc taaagggttt attgagaata tgtttttcgt ctcagccaat    1620
ccctgggtga gtttcaccag ttttgattta acgtggcca atatgacaa cttcttcgcc      1680 cccgttttca ccatgggcaa atattatacg caaggcgaca aggtgctgat gccgctggcg    1740
attcaggttc atcatgccgt ttgtgatggc ttccatgtcg gcagaatgct taatgaatta    1800
caacagtact gcgatgagtg cagggcggg gcgtaattct cgagaccggc atgagtatcc     1860
ttgtcacccg cccgtctccc gctggagaag agttagtgag ccgtctgcgc acactggggc    1920
aggtggcctg gcattttccg ctgattgagt tttctccggg tcaacaatta ccgcaacttg    1980
ctgatcaact ggcagcgctg ggggagagcg atctgttgtt tgccctctcg caacacgcgg    2040
ttgcttttgc ccaatcacag ctgcatcagc aagatcgtaa atggccccga ctacctgatt    2100
atttcgccat tggacgcacc accgcactgg cactacatac cgtaagtgga cagaagattc    2160
tctacccgca ggatcgggaa atcagcgaag tcttgctaca attacctgaa ttacaaaata    2220
ttgcgggcaa acgtgcgctg atattacgtg gcaatggtgg tcgtgagcta attggggata    2280
ccctgacggc gcgcggtgct gaggtcactt tttgtgaatg ttatcaacga tgcgcaatcc    2340
```

-continued

```
attacgatgg tgcagaagaa gcgatgcgct ggcaagcccg cgaggtgacg atggtcgttg    2400
ttaccagcgg tgaaatgttg cagcaactct ggtcgctgat cccacaatgg tatcgtgagc    2460
actggttact acactgtcga ctattggtcg tcagtgagcg tttggcgaaa ctcgcccggg    2520
aactgggctg gcaagacatt aaggtcgccg ataacgctga caacgatgcg cttttacggg    2580
cattacaata actctcataa caggaagcca taatgacgga acaagaaaaa acctccgccg    2640
tggttgaaga gaccagggag gccgtggaca ccacgtcaca acctgtcgca acagaaaaaa    2700
agagtaagaa caataccgca ttgattctca gcgcggtggc tatcgctatt gctctggcgg    2760
cgggcatcgg tttgtatggc tggggtaaac aacaggccgt caatcagacc gccaccagcg    2820
atgccctggc taaccaactg acggcattgc aaaaagccca ggagagccaa aaagccgagc    2880
tggaaggcat tattaagcaa caagctgcac aacttaagca ggcgaatcgt cagcaagaaa    2940
cgctggcaaa acagttggat gaagtccaac aaaaggtcgc caccatttcc ggcagcgatg    3000
ctaaaacctg gctgctggct caggccgatt ttctggtgaa actcgccgga cggaagctgt    3060
ggagcgatca ggacgtcacg accgctgcag cgttgctgaa aagtgcagac gccagcctgg    3120
cggatatgaa tgacccgagt ctgattaccg ttcgtcgggc aattaccgat gatatcgcca    3180
gcctttctgc agtatcgcag gtggattatg acggcatcat cctta                   3225
```

<210> SEQ ID NO 3
<211> LENGTH: 1035
<212> TYPE: DNA
<213> ORGANISM: Human tissue

<400> SEQUENCE: 3

```
atgagagtga ttcgcgtggg tacccgcaag agccagcttg ctcgcataca gacggacagt      60
gtggtggcaa cattgaaagc ctcgtaccct ggcctgcagt ttgaaatcat tgctatgtcc     120
accacagggg acaagattct tgatactgca ctctctaaga ttggagagaa aagcctgttt     180
accaaggagc ttgaacatgc cctggagaag aatgaagtgg acctggttgt tcactccttg     240
aaggacctgc ccactgtgct tcctcctggc ttcaccatcg gagccatctg caagcgggaa     300
aaccctcatg atgctgttgt ctttcaccca aaatttgttg ggaagaccct agaaaccctg     360
ccagagaaga gtgtggtggg aaccagctcc ctgcgaagag cagcccagct gcagagaaag     420
ttcccgcatc tggagttcag gagtattcgg ggaaacctca cacccggct cggaagctg      480 gacgagcagc aggagttcag tgccatcatc ctggcaacag ctggcctgca cgcatgggc     540 tggcacaacc gggttgggca gatcctgcac cctgaggaat gcatgtatgc tgtgggccag     600
ggggccttgg gcgtggaagt gcgagccaag gaccaggaca tcttggatct ggtgggtgtg     660
ctgcacgatc ccgagactct gcttcgctgc atcgctgaaa gggccttcct gaggcacctg     720
gaaggaggct gcagtgtgcc agtagccgtg catacagcta tgaaggatgg gcaactgtac     780
ctgactggag gagtctggag tctagacggc tcagatagca tacaagagac catgcaggct     840
accatccatg tccctgccca gcatgaagat ggccctgagg atgacccaca gttggtaggc     900
atcactgctc gtaacattcc acgagggccc cagttggctg cccagaactt gggcatcagc     960
ctggccaact tgttgctgag caaaggagcc aaaaacatcc tggatgttgc acggcaattg    1020
aacgatgccc attaa                                                     1035
```

<210> SEQ ID NO 4
<211> LENGTH: 1113
<212> TYPE: DNA
<213> ORGANISM: Human tissue

<400> SEQUENCE: 4

```
cacacagcct actttccaag cggagccatg tctggtaacg caatgcggc tgcaacggcg        60
gaagaaaaca gcccaaagat gagagtgatt cgcgtgggta cccgcaagag ccagcttgct       120
cgcatacaga cggacagtgt ggtggcaaca ttgaaagcct cgtaccctgg cctgcagttt       180
gaaatcattg ctatgtccac cacaggggac aagattcttg atactgcact ctctaagatt       240
ggagagaaaa gcctgtttac caaggagctt gaacatgccc tggagaagaa tgaagtggac       300
ctggttgttc actccttgaa ggacctgccc actgtgcttc ctcctggctt caccatcgga       360
gccatctgca gcgggaaaa ccctcatgat gctgttgtct ttcacccaaa atttgttggg        420
aagaccctag aaaccctgcc agagaagagt gtggtgggaa ccagctccct gcgaagagca       480
gcccagctgc agagaaagtt cccgcatctg agttcagga gtattcgggg aaacctcaac        540
acccggcttc ggaagctgga cgagcagcag gagttcagtg ccatcatcct ggcaacagct       600
ggcctgcagc gcatgggctg gcacaaccgg gttgggcaga tcctgcaccc tgaggaatgc       660
atgtatgctg tgggccaggg ggccttgggc gtggaagtgc gagccaagga ccaggacatc       720
ttggatctgg tgggtgtgct gcacgatccc gagactctgc ttcgctgcat cgctgaaagg       780
gccttcctga ggcacctgga aggaggctgc agtgtgccag tagccgtgca tacagctatg       840
aaggatgggc aactgtacct gactggagga gtctggagtc tagacggctc agatagcata       900
caagagacca tgcaggctac catccatgtc cctgcccagc atgaagatgg ccctgaggat       960
gacccacagt tggtaggcat cactgctcgt aacattccac gagggcccca gttggctgcc      1020
cagaacttgg gcatcagcct ggccaacttg ttgctgagca aggagccaa aaacatcctg       1080
gatgttgcac ggcaattgaa cgatgcccat taa                                   1113
```

<210> SEQ ID NO 5
<211> LENGTH: 1035
<212> TYPE: DNA
<213> ORGANISM: Human tissue

<400> SEQUENCE: 5

```
atgagagtga ttcgcgtggg tacccgcaag agccagcttg ctcgcataca gacggacagt        60
gtggtggcaa cattgaaagc ctcgtaccct ggcctgcagt ttgaaatcat tgctatgtcc       120
accacagggg acaagattct tgatactgca ctctctaaga ttggagagaa aagcctgttt       180
accaaggagc ttgaacatgc cctggagaag aatgaagtgg acctggttgt tcactccttg       240
aaggacctgc ccactgtgct tcctcctggc ttcaccatcg gagccatctg caagcgggaa       300
aaccctcatg atgctgttgt ctttcaccca aaatttgttg gaagaccct agaaaccctg       360
ccagagaaga gtgtggtggg aaccagctcc ctgcgaagag cagcccagct gcagagaaag       420
ttcccgcatc tggagttcag gagtattcgg gaaacctca cacccggct cggaagctg         480
gacgagcagc aggagttcag tgccatcatc ctggcaacag ctggcctgca gcgcatgggc       540
tggcacaacc gggtggggca gatcctgcac cctgaggaat gcatgtatgc tgtgggccag       600
ggggccttgg gcgtggaagt gcgagccaag gaccaggaca tcttggatct ggtgggtgtg       660
ctgcacgatc ccgagactct gcttcgctgc atcgctgaaa gggccttcct gaggcacctg       720
gaaggaggct gcagtgtgcc agtagccgtg catacagcta tgaaggatgg gcaactgtac       780
ctgactggag gagtctggag tctagacggc tcagatagca taagagac catgcaggct         840
accatccatg tccctgccca gcatgaagat ggccctgagg atgacccaca gttggtaggc       900
```

-continued

| | |
|---|---|
| atcactgctc gtaacattcc acgagggccc cagttggctg cccagaactt gggcatcagc | 960 |
| ctggccaact tgttgctgag caaaggagcc aaaaacatcc tggatgttgc acggcaattg | 1020 |
| aacgatgccc attaa | 1035 |

<210> SEQ ID NO 6
<211> LENGTH: 1035
<212> TYPE: DNA
<213> ORGANISM: Human tissue

<400> SEQUENCE: 6

| | |
|---|---|
| atgagagtga ttcgcgtggg tacccgcaag agccagcttg ctcgcataca gacggacagt | 60 |
| gtggtggcaa cattgaaagc ctcgtaccct ggcctgcagt ttgaaatcat tgctatgtcc | 120 |
| accacagggg acaagattct tgatactgca ctctctaaga ttggagagaa aagcctgttt | 180 |
| accaaggagc ttgaacatgc cctggagaag aatgaagtgg acctggttgt tcactccttg | 240 |
| aaggacctgc ccactgtgct tcctcctggc ttcaccatcg agccatctg caagcgggaa | 300 |
| aaccctcatg atgctgttgt ctttcaccca aaatttgttg ggaagaccct agaaaccctg | 360 |
| ccagagaaga gtgtggtggg aaccagctcc ctgcgaagag cagcccagct gcagagaaag | 420 |
| ttcccgcatc tggagttcag gagtattcgg ggaaacctca cacccggct tcggaagctg | 480 |
| gacgagcagc aggagttcag tgccatcatc ctggcaacag ctggcctgca gcgcatgggc | 540 |
| tggcacaacc gggtggggca gatcctgcac cctgaggaat gcatgtatgc tgtgggccag | 600 |
| ggggccttgg gcgtggaagt gcgagccaag gaccaggaca tcttggatct ggtgggtgtg | 660 |
| ctgcacgatc ccgagactct gcttcgctgc atcgctgaaa gggccttcct gaggcacctg | 720 |
| gaaggaggct gcagtgtgcc agtagccgtg catacagcta tgaaggatgg gcaactgtac | 780 |
| ctgactggag gagtctggag tctagacggc tcagatagca tacaagagac catgcaggct | 840 |
| accatccatg tccctgccca gcatgaagat ggccctgagg atgacccaca gttggtaggc | 900 |
| atcactgctc gtaacattcc acgagggccc cagttggctg cccagaactt gggcatcagc | 960 |
| ctggccaact tgttgctgag caaaggagcc aaaaacatcc tggatgttgc acggcaattg | 1020 |
| aacgatgccc attaa | 1035 |

<210> SEQ ID NO 7
<211> LENGTH: 1034
<212> TYPE: DNA
<213> ORGANISM: Human tissue

<400> SEQUENCE: 7

| | |
|---|---|
| atgagagtga ttcgcgtggg tacccgcaag agccagcttg ctcgcataca gacggacagt | 60 |
| gtggtggcaa cattgaaagc ctcgtaccct ggcctgcagt ttgaaatcat tgctatgtcc | 120 |
| accacagggg acaagattct tgatactgca ctctctaaga ttggagagaa aagcctgttt | 180 |
| accaaggagc ttgaacatgc cctggagaag aatgaagtgg acctggttgt tcactccttg | 240 |
| aaggacctgc ccactgtgct tcctcctggc ttcaccatcg agccatctg caagcgggaa | 300 |
| aaccctcatg atgctgttgt cttcacccaa aatttgttgg aagaccctga aaccctgc | 360 |
| cagagaagag tgtggtggga accagctccc tgcgaagagc agcccagctg cagagaaagt | 420 |
| tcccgcatct ggagttcagg agtattcggg gaaacctcaa cacccggctt cggaagctgg | 480 |
| acgagcagca ggagttcagt gccatcatcc tggcaacagc tggcctgcag cgcatgggct | 540 |
| ggcacaaccg ggtggggcag atcctgcacc ctgaggaatg catgtatgct gtgggccagg | 600 |
| gggccttggg cgtggaagtg cgagccaagg accaggacat cttggatctg gtgggtgtgc | 660 |

```
tgcacgatcc cgagactctg cttcgctgca tcgctgaaag ggccttcctg aggcacctgg      720
aaggaggctg cagtgtgcca gtagccgtgc atacagctat gaaggatggg caactgtacc      780
tgactggagg agtctggagt ctagacggct cagatagcat acaagagacc atgcaggcta      840
ccatccatgt ccctgcccag catgaagatg gccctgagga tgacccacag ttggtaggca      900
tcactgctcg taacattcca cgagggcccc agttggctgc ccagaacttg ggcatcagcc      960
tggccaactt gttgctgagc aaaggagcca aaaacatcct ggatgttgca cggcaattga     1020
acgatgccca ttaa                                                       1034
```

<210> SEQ ID NO 8
<211> LENGTH: 1035
<212> TYPE: DNA
<213> ORGANISM: Human tissue

<400> SEQUENCE: 8

```
atgagagtga ttcgcgtggg tacccgcaag agccagcttg ctcgcataca gacgggcagt       60
gtggtggcaa cattgaaagc ctcgtaccct ggcctgcagt ttgaaatcat tgctatgtcc      120
accacagggg acaagattct tgatactgca ctctctaaga ttggagagaa agcctgtttt      180
accaaggagc ttgaacatgc cctggagaag aatgaagtgg acctggttgt tcactccttg      240
aaggacctgc ccactgtgct tcctcctggc ttcaccatcg gagccatctg caagcgggaa      300
aaccctcatg atgctgttgt ctttcaccca aaatttgttg ggaagaccct agaaaccctg      360
ccagagaaga gtgtggtggg aaccagctcc ctgcgaagag cagcccagct gcagagaagg      420
ttcccgcatc tggagttcag gagtattcgg ggaaacctca cacccggct tcggaagctg      480 gacgagcagc aggagttcag tgtcatcatc ctggcaacag ctggcctgca gcgcatgggc      540
tggcacaacc gggttgggca gatcctgcac cctgaggaat gcatgtatgc tgtgggccag      600
ggggccttgg gcgtggaagt gcgagccaag gaccaggaca tcttggatct ggtgggtgtg      660
ctgcacgatc ccgagactct gcttcgctgc atcgctgaaa gggccttcct gaggcacctg      720
gaaggaggct gcagtgtgcc agtagccgtg catacagcta tgaaggatgg gcaactgtac      780
ctgactggag gagtctggag tctagacggc tcagatagca taccagagac catgcaggct      840
accatccatg tccctgccca gcatgaagat ggccctgagg atgacccaca gttggtaggc      900
atcactgctc gtaacattcc acgagggccc cagttggctg cccagaactt gggcatcagc      960
ctggccaact tgttgctgag caaaggagcc aaaaacatcc tggatgttgc acggcaattg     1020
aacgatgccc attaa                                                      1035
```

<210> SEQ ID NO 9
<211> LENGTH: 1035
<212> TYPE: DNA
<213> ORGANISM: Human tissue

<400> SEQUENCE: 9

```
atgagagtga ttcgcgtggg tacccgcaag agccagcttg ctcgcataca gacggacagt       60
gtggtggcaa cattgaaagc ctcgtaccct ggcctgcagt ttgaaatcat tgctatgtcc      120
accacagggg acaagattct tgatactgca ctctctaaga ttggagagaa agcctgtttt      180
accaaggagc ttgaacatgc cctggagaag aatgaagtgg acctggttgt tcactccttg      240
aaggacctgc ccactgtgct tcctcctggc ttcaccatcg gagccatctg caagcgggaa      300
aaccctcatg atgctgttgt ctttcaccca aaatttgttg ggaagaccct agaaaccctg      360
```

-continued

```
ccagagaaga gtgtggtggg aaccagctcc ctgcgaagag cagcccagct gcagagaaag      420
ttcccgcatc tggagttcag gagtattcgg ggaaacctca acacccggct tcggaagctg      480
gacgagcagc aggagttcag tgccatcatc ctggcaacag ctggcctgca cgcatgggc      540 tggcacaacc gggtggggca gatcctgcac cctgaggaat gcatgtatgc tgtgggccag      600
ggggccttgg gcgtggaagt gcgagccaag gaccaggaca tcttggatct ggtgggtgtg      660
ctgcacgatc ccgagactct gcttcgctgc atcgctgaaa gggccttcct gaggcacctg      720
gaaggaggtt gcagtgtgcc agtagccgtg catacagcta tgaaggatgg gcaactgtac      780
ctgactggag gagtctggag tctagacggc tcagatagca tacaagagac catgcaggct      840
accatccatg tccctgccca gcatgaagat ggccctgagg atgacccaca gttggtaggc      900
atcactgctc gtaacattcc acgagggccc cagttggctg cccagaactt gggcatcagc      960
ctggccaact tgttgctgag caaaggagcc aaaaacatcc tggatgttgc acggcaattg     1020
aacgatgccc attaa                                                      1035

<210> SEQ ID NO 10
<211> LENGTH: 1034
<212> TYPE: DNA
<213> ORGANISM: Human tissue

<400> SEQUENCE: 10
atgagagtga ttcgcgtggg tacccgcaag agccagcttg ctcgcataca gacggacagt       60
gtggtggcaa cattgaaagc ctcgtaccct ggcctgcagt ttgaaatcat tgctatgtcc      120
accacagggg acaagattct tgatactgca ctctctaaga ttggagagaa aagcctgttt      180
accaaggagc ttgaacatgc cctggagaag aatgaagtgg acctggttgt tcactccttg      240
aaggacctgc ccactgtgct tcctcctggc ttcaccatcg gagccatctg caagcgggaa      300
aaccctcatg atgctgttgt ctttcaccca aaatttgttg ggaagaccct agaaccctg      360 ccagagaaga gtgtggtggg aaccagctcc ctgcgaagag cagcccagct gcagagaaag      420
ttcccgcatc tggagttcag gagtattcgg ggaaacctca acacccggct tcggaagctg      480
gacgagcagc aggagttcag tgccatcatc ctggcaacag ctggcctgca cgcatgggc      540 tggcacaacc gggtggggca gatcctgcac cctgaggaat gcatgtatgc tgtgggccag      600
ggggccttgg gcgtggaagt gcgagccaag gaccaggaca tcttggatct ggtgggtgtg      660
ctgcacgatc ccgagactct gcttcgctgc atcgctgaaa gggccttcct gaggcacctg      720
gaaggaggct gcagtgtgcc agtagccgtg catacagcta tgaaggatgg gcaactgtac      780
ctgactggag gagtctggag tctagacggc tcagatagca tacaagagac catgcaggct      840
accatccatg tccctgccca gcatgaagat ggccctgagg atgacccaca gttggtaggc      900
atcactgctc gtaacattcc acgagggccc cagttggctg cccagaactt gggcatcagc      960
ctggccaact tgttgctgag caaaggagcc aaaaacatcc tggatgttgc acggcaatta     1020
acgatgccca ttaa                                                       1034

<210> SEQ ID NO 11
<211> LENGTH: 1035
<212> TYPE: DNA
<213> ORGANISM: Human tissue

<400> SEQUENCE: 11
atgagagtga ttcgcgtggg tacccgcaag agccagcttg ctcgcataca gacggacagt       60
gtggtggcaa cattgaaagc ctcgtaccct ggcctgcagt ttgaaatcat tgctatgtcc      120
```

```
accacagggg acaagattct tgatactgca ctctctaaga ttggagagaa aagcctgttt      180
accaaggagc ttgaacatgc cctggagaag aatgaagtgg acctggttgt tcactccttg      240
aaggacctgc ccactgtgct tcctcctggc ttcaccatcg gagccatctg caagcgggaa      300
aaccctcatg atgctgttgt ctttcaccca aaatttgttg ggaagaccct agaaaccctg      360
ccagagaaga gtgtggtggg aaccagctcc ctgcgaagag cagcccagct gcagagaaag      420
ttcccgcatc tggagttcag gagtattcgg ggaaacctca acacccggct tcggaagctg      480
gacgagcagc aggagttcag tgccatcatc ctggcaacag ctggcctgca gcgcatgggc      540
tggcacaacc gggtggggca gatcctgcac cctgaggaat gcatgtatgc tgtgggccag      600
ggggccttgg gcgtggaagt gcgagccaag gaccaggaca tcttggatct ggtgggtgtg      660
ctgcacgatc ccgagactct gcttcgctgc atcgctgaaa gggccttcct gaggcacctg      720
gaaggaggct gcagtgtgcc agtagccgtg catacagcta tgaaggatgg gcaactgtac      780
ctgactggag gagtctggag tctagacggc tcagatagca tacaagagac catgcaggcc      840
accatccatg tccctaccca gcatgaagat ggccctgagg atgacccaca gttggtaggc      900
atcactgctc gtaacattcc acgagggccc cagttggctg cccagaactt gggcatcagc      960
ctggccaact tgttgctgag caaaggagcc aaaaacatcc tggatgttgc acggcaattg     1020
aacgatgccc attaa                                                      1035

<210> SEQ ID NO 12
<211> LENGTH: 3988
<212> TYPE: DNA
<213> ORGANISM: Human tissue

<400> SEQUENCE: 12
cacctgacgc gccctgtagc ggcgcattaa gcgcggcggg tgtggtggtt acgcgcagcg       60
tgaccgctac acttgccagc gccctagcgc ccgctccttt cgctttcttc ccttcctttc      120
tcgccacgtt cgccggcttt cccgtcaag ctctaaatcg ggggctccct ttagggttcc       180
gatttagtgc tttacggcac ctcgacccca aaaaacttga ttaggtgat ggttcacgta       240 gtgggccatc gccctgatag acggttttc gccctttgac gttggagtcc acgttcttta      300
atagtggact cttgttccaa actggaacaa cactcaaccc tatctcggtc tattcttttg      360
atttataagg gatttttgccg atttt cggcct attggttaaa aaatgagctg atttaacaaa   420
aatttaacgc gaattttaac aaaatattaa cgcttacaat ttccattcgc cattcaggct      480
gcgcaactgt tgggaagggc gatcggtgcg ggcctcttcg ctattacgcc agctggcgaa      540
agggggatgt gctgcaaggc gattaagttg gtaacgcca gggttttccc agtcacgacg      600
ttgtaaaacg acggccagtg aattgtaata cgactcacta tagggcgaat tgggtaccgg      660
gccccccctc gaggtcgacg gtatcgataa gcttattaat gggcatcgtt caattgccgt      720
gcaacatcca ggatgttttt ggctccttttg ctcagcaaca agttggccag gctgatgccc      780
aagttctggg cagccaactg ggcccctcgt ggaatgttac gagcagtgat gcctaccaac      840
tgtgggtcat cctcagggcc atcttcatgc tgggcaggga catggatggt agcctgcatg      900
gtctcttgta tgctatctga gccgtctaga ctccagactc ctccagtcag gtacagttgc      960
ccatccttca tagctgtatg cacggctact ggcacactgc agcctccttc caggtgcctc     1020
aggaaggccc tttcagcgat gcagcgaagc agagtctcgg gatcgtgcag cacccccacc     1080
agatccaaga tgtcctggtc cttggctcgc acttccacgc ccaaggcccc ctggcccaca     1140
```

-continued

| | | | | |
|---|---|---|---|---|
| gcatacatgc | attcctcagg | gtgcaggatc | tgcccaaccc | ggttgtgcca gcccatgcgc | 1200 |
| tgcaggccag | ctgttgccag | gatgatggca | ctgaactcct | gctgctcgtc cagcttccga | 1260 |
| agccggtgt | tgaggtttcc | ccgaatactc | ctgaactcca | gatgcgggaa ctttctctgc | 1320 |
| agctgggctg | ctcttcgcag | ggagctggtt | cccaccacac | tcttctctgg cagggtttct | 1380 |
| agggtcttcc | caacaaattt | tgggtgaaag | acaacagcat | catgagggtt ttcccgcttg | 1440 |
| cagatggctc | cgatggtgaa | gccaggagga | agcacagtgg | gcaggtcctt caaggagtga | 1500 |
| acaaccaggt | ccacttcatt | cttctccagg | gcatgttcaa | gctccttggt aaacaggctt | 1560 |
| ttctctccaa | tcttagagag | tgcagtatca | agaatcttgt | ccctgtggt ggacatagca | 1620 |
| atgatttcaa | actgcaggcc | agggtacgag | gctttcaatg | ttgccaccac actgtccgtc | 1680 |
| tgtatgcgag | caagctggct | cttgcgggta | cccacgcgaa | tcactctcat gaattcctgc | 1740 |
| agcccggggg | atccactagt | tctagagcgg | ccgccaccgc | ggtggagctc cagcttttgt | 1800 |
| tccctttagt | gagggttaat | ttcgagcttg | gcgtaatcat | ggtcatagct gtttcctgtg | 1860 |
| tgaaattgtt | atccgctcac | aattccacac | aacatacgag | ccggaagcat aaagtgtaaa | 1920 |
| gcctgggtg | cctaatgagt | gagctaactc | acattaattg | cgttgcgctc actgcccgct | 1980 |
| ttccagtcgg | gaaacctgtc | gtgccagctg | cattaatgaa | tcggccaacg cgcggggaga | 2040 |
| ggcggtttgc | gtattgggcg | ctcttccgct | tcctcgctca | ctgactcgct gcgctcggtc | 2100 |
| gttcggctgc | ggcgagcggt | atcagctcac | tcaaaggcgg | taatacggtt atccacagaa | 2160 |
| tcaggggata | acgcaggaaa | gaacatgtga | gcaaaaggcc | agcaaaaggc caggaaccgt | 2220 |
| aaaaaggccg | cgttgctggc | gttttttccat | aggctccgcc | ccctgacga gcatcacaaa | 2280 |
| aatcgacgct | caagtcagag | gtggcgaaac | ccgacaggac | tataaagata ccaggcgttt | 2340 |
| ccccctggaa | gctccctcgt | gcgctctcct | gttccgaccc | tgccgcttac cggatacctg | 2400 |
| tccgcctttc | tcccttcggg | aagcgtggcg | ctttctcata | gctcacgctg taggtatctc | 2460 |
| agttcggtgt | aggtcgttcg | ctccaagctg | ggctgtgtgc | acgaaccccc cgttcagccc | 2520 |
| gaccgctgcg | ccttatccgg | taactatcgt | cttgagtcca | acccggtaag acacgactta | 2580 |
| tcgccactgg | cagcagccac | tggtaacagg | attagcagag | cgaggtatgt aggcggtgct | 2640 |
| acagagttct | tgaagtggtg | gcctaactac | ggctacacta | gaaggacagt atttggtatc | 2700 |
| tgcgctctgc | tgaagccagt | taccttcgga | aaaagagttg | gtagctcttg atccggcaaa | 2760 |
| caaaccaccg | ctggtagcgg | tggtttttttt | gtttgcaagc | agcagattac gcgcagaaaa | 2820 |
| aaaggatctc | aagaagatcc | tttgatcttt | tctacggggt | ctgacgctca gtggaacgaa | 2880 |
| aactcacgtt | aagggatttt | ggtcatgaga | ttatcaaaaa | ggatcttcac ctagatcctt | 2940 |
| ttaaattaaa | aatgaagttt | taaatcaatc | taaagtatat | atgagtaaac ttggtctgac | 3000 |
| agttaccaat | gcttaatcag | tgaggcacct | atctcagcga | tctgtctatt tcgttcatcc | 3060 |
| atagttgcct | gactccccgt | cgtgtagata | actacgatac | gggagggctt accatctggc | 3120 |
| cccagtgctg | caatgatacc | gcgagaccca | cgctcaccgg | ctccagattt atcagcaata | 3180 |
| aaccagccag | ccggaagggc | cgagcgcaga | agtggtcctg | caactttatc cgcctccatc | 3240 |
| cagtctatta | attgttgccg | ggaagctaga | gtaagtagtt | cgccagttaa tagtttgcgc | 3300 |
| aacgttgttg | ccattgctac | aggcatcgtg | gtgtcacgct | cgtcgtttgg tatggcttca | 3360 |
| ttcagctccg | gttcccaacg | atcaaggcga | gttacatgat | cccccatgtt gtgcaaaaaa | 3420 |
| gcggttagct | ccttcggtcc | tccgatcgtt | gtcagaagta | agttggccgc agtgttatca | 3480 |
| ctcatggtta | tggcagcact | gcataattct | cttactgtca | tgccatccgt aagatgcttt | 3540 |

```
tctgtgactg gtgagtactc aaccaagtca ttctgagaat agtgtatgcg gcgaccgagt     3600
tgctcttgcc cggcgtcaat acgggataat accgcgccac atagcagaac tttaaaagtg     3660
ctcatcattg gaaaacgttc ttcggggcga aaactctcaa ggatcttacc gctgttgaga     3720
tccagttcga tgtaacccac tcgtgcaccc aactgatctt cagcatcttt tactttcacc     3780
agcgtttctg ggtgagcaaa aacaggaagg caaaatgccg caaaaaaggg aataagggcg     3840
acacggaaat gttgaatact catactcttc cttttcaat attattgaag catttatcag       3900
ggttattgtc tcatgagcgg atacatattt gaatgtattt agaaaaataa acaaataggg     3960
gttccgcgca catttccccg aaaagtgc                                         3988

<210> SEQ ID NO 13
<211> LENGTH: 1260
<212> TYPE: DNA
<213> ORGANISM: Human tissue

<400> SEQUENCE: 13
cacaggaaac agctatgacc atgattacgc caagctcgaa attaaccctc actaaaggga       60
acaaaagctg gagctccacc gcggtggcgg ccgctctaga actagtggat ccccccgggct    120 gcaggaattc atgagagtga ttcgcgtggg tacccgcaag agccagcttg ctcgcataca     180
gacggacagt gtggtggcaa cattgaaagc ctcgtaccct ggcctgcagt ttgaaatcat     240
tgctatgtcc accacagggg acaagattct tgatactgca ctctctaaga ttggagagaa     300
aagcctgttt accaaggagc ttgaacatgc cctggagaag aatgaagtgg acctggttgt     360
tcactccttg aaggacctgc ccactgtgct tcctcctggc ttcaccatcg agccatctg      420 caagcgggaa aaccctcatg atgctgttgt cttcacccca aaatttgttg ggaagaccct     480
agaaaccctg ccagagaaga gtgtggtggg aaccagctcc ctgcgaagag cagcccagct     540
gcagagaaag ttcccgcatc tggagttcag gagtattcgg ggaaacctca cacccggct      600 tcggaagctg gacgagcagc aggagttcag tgccatcatc ctggcaacag ctggcctgca     660
gcgcatgggc tggcacaacc gggttgggca gatcctgcac cctgaggaat gcatgtatgc     720
tgtgggccag ggggccttgg gcgtggaagt gcgagccaag gaccaggaca tcttggatct     780
ggtgggtgtg ctgcacgatc ccgagactct gcttcgctgc atcgctgaaa gggccttcct     840
gaggcacctg gaaggaggct gcagtgtgcc agtagccgtg catacagcta tgaaggatgg     900
gcaactgtac ctgactggag gagtctggag tctagacggc tcagatagca tacaagagac     960
catgcaggct accatccatg tccctgccca gcatgaagat ggccctgagg atgacccaca    1020
gttggtaggc atcactgctc gtaacattcc acgagggccc cagttggctg cccagaactt    1080
gggcatcagc ctggccaact tgttgctgag caaggagcc aaaaacatcc tggatgttgc     1140
acggcaattg aacgatgccc attaataagc ttatcgatac cgtcgacctc gaggggggc     1200 ccggtaccca attcgcccta tagtgagtcg tattacaatt cactggccgt cgttttacaa    1260

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 14
cgtggaattc atgagagtga ttcgcgtggg ta                                     32
```

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 15
ggagaagctt attaatgggc atcgttcaat tgccgtgcaa catccag         47

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 16
tcgcctccct ctagtctctg                                        20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 17
cagcaggagt tcagtgccat c                                      21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 18
gatggcactg aactcctgct g                                      21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 19
cagcaaccca ggcatctgtg                                        20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 20
gtaatacgac tcactatagg gc                                     22

```
<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 21
ctaaagggaa caaaagctgg ag                                              22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 22
cagctatgac catgattacg c                                               21

<210> SEQ ID NO 23
<211> LENGTH: 54
<212> TYPE: DNA
<213> ORGANISM: Artificial Sequence
<220> FEATURE:
<221> NAME/KEY: CDS
<222> LOCATION: (32)..(52)
<223> OTHER INFORMATION: Description of Artificial Sequence: Modified 5'
      untranslated region of plasmid pExp1 (P 27, L 17-25)

<400> SEQUENCE: 23
aattctaaca taagttaagg aggaaaaaaa a atg aga gtt att cgt gtc ggt ac    54
                                    Met Arg Val Ile Arg Val Gly
                                     1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: N-terminal
      of peptide encoded by ID 23; related to N-terminal of PBGD
      (P 27, L 23-27)

<400> SEQUENCE: 24

Met Arg Val Ile Arg Val Gly
              5

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 25
aattctaaca taagttaagg aggaaaaaaa aatgagagtt attcgtgtcg gtac           54

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Primer for
      PCR amplification
```

<400> SEQUENCE: 26
cgacacgaat aactctcatt tttttttcct ccttaactta tgttag           46

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 27
gatcactcat gtttgacagc ttatcatcga tt                          32

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 28
agctaatcga tgataagcgt caaacatgag                             30

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 29
agtcagaatt cagacgcacg gcggtacgat aa                          32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 30
attcactcga ggtcaccatc ggtaccagtt ca                          32

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 31
agatcaagct tcggccagac gcaggttatc ta                          32

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Primer for
      PCR amplification -continued

<400> SEQUENCE: 32
atacactcga gaccggcatg agtatccttg tcac                              34

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 33
actgacctcg agcggcacgt aagaggttcc                                   30

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 34
actgaactcg agaattacgc cccgccctg                                    29

<210> SEQ ID NO 35
<211> LENGTH: 60
<212> TYPE: DNA
<213> ORGANISM: Artificial Sequence
<220> FEATURE:
<221> NAME/KEY: CDS
<222> LOCATION: (1)..(60)
<223> OTHER INFORMATION: Description of Artificial Sequence: Primer for
      PCR amplification

<400> SEQUENCE: 35 atg tct ggt aac ggc att gcg gct gca acg gcg gaa gaa aac agc cca    48
Met Ser Gly Asn Gly Ile Ala Ala Ala Thr Ala Glu Glu Asn Ser Pro
 1               5                  10                  15 aag atg aga gtg                                                    60
Lys Met Arg Val
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Primer for
      PCR amplification

<400> SEQUENCE: 36

Met Ser Gly Asn Gly Ile Ala Ala Ala Thr Ala Glu Glu Asn Ser Pro
 1               5                  10                  15

Lys Met Arg Val
            20

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Fragment of
      normal chromosomal sequence

<400> SEQUENCE: 37

-continued

```
agcgcatggg ctggcacaac cgggt                                            25

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: encoded by
      SEQ ID NO:37

<400> SEQUENCE: 38

Gln Arg Met Gly Trp His Asn Arg Val
 1               5

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Fragment of
      AIP chromosomal sequence

<400> SEQUENCE: 39
agcgcatggg ctagcacaac cgggt                                            25

<210> SEQ ID NO 40
<211> LENGTH: 68
<212> TYPE: DNA
<213> ORGANISM: Artificial Sequence
<220> FEATURE:
<223> OTHER INFORMATION: Description of Artificial Sequence: linear
      single-stranded chimeric (RNA/DNA) oligonucleotide with hairpin
      secondary structure
<221> NAME/KEY: stem loop
<222> LOCATION: (1)..(25)
<223> OTHER INFORMATION: base pairs to (55)...(31), respectively
<221> NAME/KEY: stem loop
<222> LOCATION: (31)..(55)
<223> OTHER INFORMATION: base pairs to (25)...(1), respectively
<221> NAME/KEY: misc_RNA
<222> LOCATION: (31)..(40)
<223> OTHER INFORMATION: modified RNA region in chimeric DNA/RNA
      molecule
<221> NAME/KEY: misc_RNA
<222> LOCATION: (46)..(55)
<223> OTHER INFORMATION: modified RNA region in chimeric DNA/RNA
      molecule
<223> OTHER INFORMATION: modified_base (31), (49)
      am
<223> OTHER INFORMATION: modified_base (35), (36), (39), (51), (53)
      gm
<223> OTHER INFORMATION: modified_base (32), (33), (34), (46), (47),
      (48), (52), (54) cm
<223> OTHER INFORMATION: modified_base (37), (38), (40), (50), (55)
      um

<400> SEQUENCE: 40
agcgcatggg ctggcacaac cgggtttttta cccggttgtg ccagcccatg cgctccgggt      60
tttcccgg                                                               68
```

HUMAN PORPHOBILINOGEN DEAMINASE SEQUENCES

Figure 1:
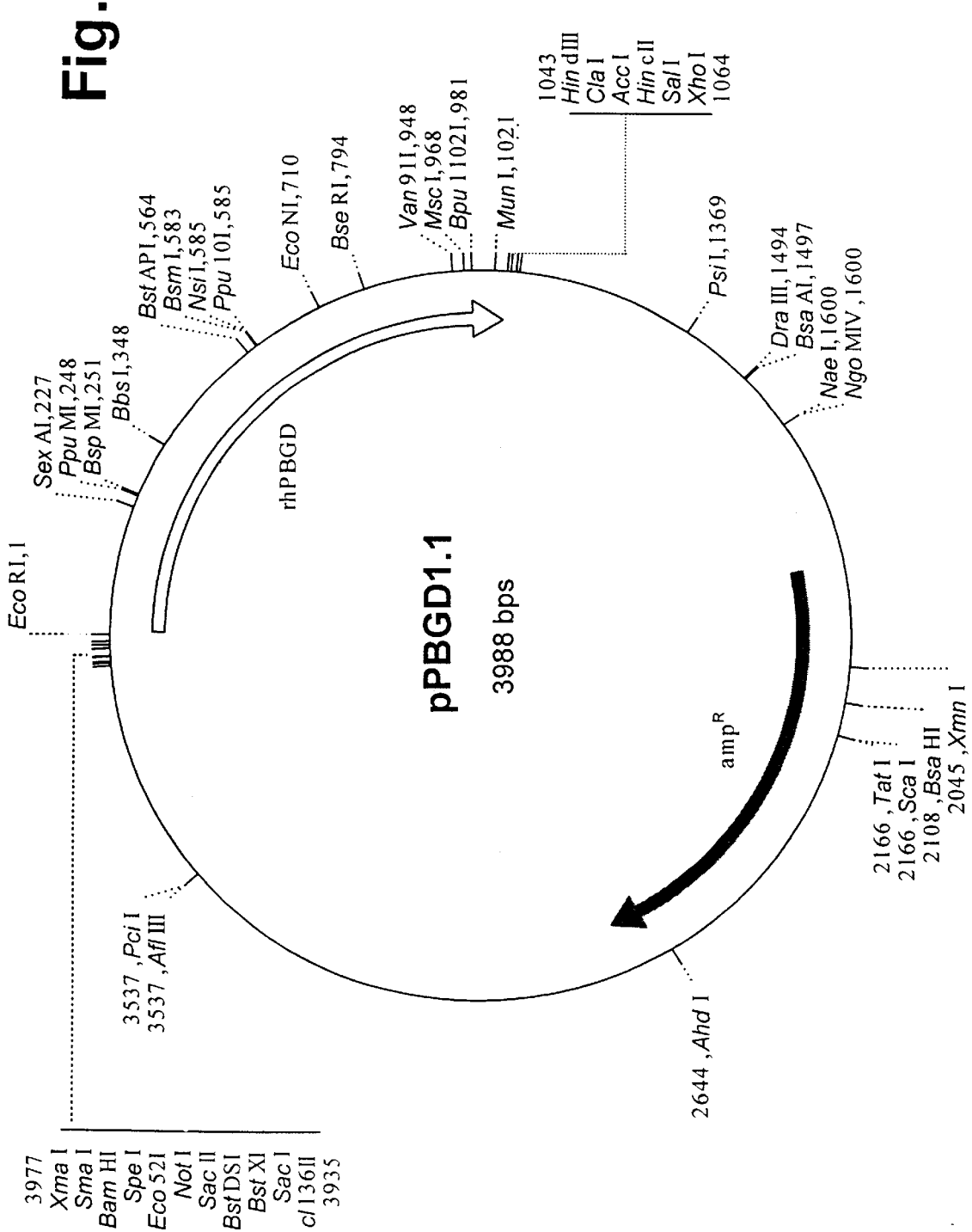

This application is a nonprovisional of 60/094,258 filed Jul. 27, 1998.

FIELD OF THE INVENTION

The present invention relates to novel methods of treating and preventing disease caused by absence or deficiency of the activity of enzymes belonging to the heme biosynthetic pathway. More specifically, the invention pertains to methods of alleviating the symptoms of certain porphyrias, notably acute intermittent porphyria including gene therapy, therapy with a combination of encymatically active substances and therapy with recombinant produced enzymes such as PBGD. In addition the invention relates to an expression plasmid and a linear DNA fragment for use in the production of rhPBGD.

BACKGROUND OF THE INVENTION

Heme Biosynthetic Pathway

Heme is a vital molecule for life in all living higher animal species. Heme is involved in such important processes as oxygen transportation (haemoglobin), drug detoxification (cytochrome P450), and electron transfer for the generation of chemical energy (ATP) during oxidative phosphorylation in mitochondria.

Heme is synthesised in eight consecutive enzymatic steps starting with glycin and succinyl-CoA. Sassa S. 1996, Blood Review, 10, 53–58 shows a schematic drawing (FIG. 1 in the article) of the heme biosynthetic pathway indicating that the first enzymatic step (delta-aminolevulinic-synthetase) and the last three steps (coproporphyrinogen oxidase, protoporphyrinogen oxidase and ferrochelatase) are located in the mitochondrion whereas, the remaining are cytosolic enzymes.

Important regulation of the heme biosynthetic pathway is delivered by the end product of the metabolic pathway, namely heme, which exerts a negative inhibition on the first rate-limiting enzymatic step (conducted by delta-aminolevulinic-synthetase) in the heme biosynthetic pathway (Strand et al. 1970, Proc. Natl. Acad. Sci. 67, 1315–1320).

Deficiencies in the heme biosynthetic enzymes have been reported leading to a group of diseases collectively called porphyrias.

A defect in the third enzymatic step leads to acute intermittent porphyria, AIP.

Acute Intermittent Porphyria

Acute intermittent porphyria (AIP) is an autosomal dominant disorder in man caused by a defect (50% reduction of activity) of the third enzyme in the heme biosynthetic pathway, prophobilinogen deaminase, (also known as porphobilinogen ammonia-lyase (polymerizing)), E.C. 4.3.1.8. (Waldenström 1937, J. Acta.Med. Scand. Suppl.82). In the following, this enzyme and the recombinant human form will be termed "PBGD" and "rhPBGD", respectively.

Clinical Manifestation of AIP

The reduction is enzymatic PBGD activity makes this enzyme the rate limiting step in the heme biosynthetic pathway, with a concomitant increase in urinary and serum levels of delta-aminolevulinic acid (ALA) and porphobilonogen (PBG).

The clinical manifestation of API involves abdominal pain and a variety of neuropsychiatric and circulatory dysfunctions. As a result of the enzymatic block, heme precursors such as PBG and ALA are excreted in excess amounts in the urine and stool. In acute attacks, high levels of PGB and ALA are also found in serum. These precursors are normally undetectable in serum in healthy individuals.

The neuropsychiatric disturbances observed in these patients are thought to be due to interference of the precursors with the nervous system or due to the lack of heme. For instance, ALA bears a close resemblance to the inhibitory neurotransmitter 4-aminobutyric acid (GABA) and has been suggested to be a neurotoxin. (Jeans J. et al. 1996, American J. of Medical Genetics. 65, 269–273).

Abdominal pain is the most frequent symptom in AIP patients and occurs in more than 90% during acute attacks, which will be followed rapidly by the development of peripheral neuropathy with weakness in proximal muscles, loss of pinprick sensation, and paraesthesia. Tachycardia, obstipation or diarrhoea may also be present. During acute attacks behavioral changes, confusion, seizures, respiratory paralysis, coma and hallucinations may be present.

Hypertension is also associated with AIP, with as high as 40% of patients showing sustained hypertension between attacks. An association between chronic renal failure (Yeung L. et al. 1983, Q J. Med 52, 92–98) and AIP as well as hepatocellular carcinoma. (Lithner F. et al. 1984, Acta.Med-.Scand. 215, 271–274), has been reported.

The AIP is a lifelong disease, which usually becomes manifest in puberty.

Factors Precipitating Acute Attacks

Most precipitating factors exhibit an association with the first rate-limiting enzyme in the heme biosynthetic pathway through heme, the final product of the pathway. A lowering of the heme concentration will immediately increase the rate of ALA-synthetase. An overproduction of ALA then makes the partially deficient PBGD enzyme (50% activity) now rate-limiting with an accumulation of the heme precursors ALA and PBG. Drugs that induces cytochrome P450 such as barbiturates, estrogens, sulphonamides, progesterone, carbamyazepine, and phenytoin can all precipitate acute attacks. (Wetterberg L. 1976, In Doss M. Nowrocki P. eds. Prophyrias in Human Disease. Reports of the discussion. Matgurg an der Lahn, 191–202).

The clinical manifestation is more common in women, especially at time of menstruation. Endocrine factors such as synthetic estrogens and progesterone are known precipitating factors. A significant factor is also the lack of sufficient caloric intake. Hence, caloric supplementation during acute attacks reduces clinical symptoms. (Welland, F. H. et al. 1964, Metabolism, 13, 232).

Finally, various forms of stress including illness, infection, surgery and alcoholic excess have been shown to lead to precipitation of acute attacks. There are also cases of acute attacks where no precipitating factor can be identified. Prevalence of AIP Prevalence of 0.21% has been reported (Tishler P. V. et al. 1985, Am.J.Psychiatry 142, 1430–1436), with as high a prevalence as 1 per 1500 in geographic isolates in northern Sweden (Wetterberg L. 1967, Svenska bokförlaget Nordstedt, Stockholm). Prevalence up to 200 per 10,000 inhabitants has been reported from Arjepong in Northern Sweden (Andersson, Christer, Thesis, 1997, ISBN 91/7191/280/0, pp. 22–23).

Existing Treatment of AIP

The treatment of AIP as well as of other types of porphyrias such as variegata, hereditary coproporphyria, harderoporphyria, and aminolevulinic acid dehydratase deficiency, are basically the same. Existing therapies for AIP, are all aimed at reducing circulating PBG and ALA by inhibiting the first rate-limiting enzymatic step ALA-synthetase. This inhibition of ALA-synthetase is achieved by increasing circulating heme, since heme is a negative feed back regulator of ALA-synthetase. Hematin treatment, high caloric intake or inhibition of heme breakdown by Sn-mesoporphyrin administration are the existing therapies today. These therapies have shown limited efficacy.

Treatment between acute attacks involves sufficient caloric intake and avoidance of drugs and immediate treatment of infections.

Patients that experience acute attacks are treated with intravenous carbohydrates usually dextrose (300 g/day) and intravenous hematin (3–8 mg/(kg day)).

Treatments with long acting agonistic analogues of LHRH, have been shown to reduce the incidence of premenstrual attacks by inhibiting ovulation in AIP patients. Finally, treatments involving heme analogous Sn-mesoporphyrin, which inhibit heme breakdown have also been attempted.

Medical Need in AIP

The lack of effective treatment for AIP is well recognized. In a US mortality study in AIP patients requiring hospitalization it was concluded that the mortality rate was 3.2-fold higher as compared to a matched general population. Suicide was also a major cause of death, occurring at a rate of 370 times that expected in the general population (Jeans J. et al. 1996, Am. J. of Medical Genetics 65, 269–273).

Hematin therapy is usually initiated when high caloric intake is not sufficient to alleviate acute attacks. Studies with hematin have been performed but these studies generally used the patients as their own control after the patients did not respond to high carbohydrate treatment (Mustajoki et al. 1989, Sem. Hematol. 26, 1–9).

The one controlled study with hematin treatment reported, failed to reach statistical significance due to too small a patient number (Herric A. L. et al 1989, Lancet 1, 1295–1297).

In conclusion, there is a definite need for the provision of novel therapeutic/prophylactic methods aimed at these disease.

DISCLOSURE OF THE INVENTION

Levels of ALA and PBG found in urine in patients with symptomatic AIP, are in the range of 1-203 mg/day and 4-782 mg/day, respectively. Normal excretion of ALA and PBG is very low (0–4 mg/day). Important is the observation that these patients also have elevated levels of ALA and PBG in serum. It was shown in a study that AIP patients had significantly elevated levels of ALA (96 $\mu$g %) and PBG (334 $\mu$g %) in serum in connection with acute attacks and that the severity of the attacks were correlated to high levels of ALA and PBG. Hence, it is important to reduce the circulating levels of ALA and PBG in order to eliminate clinical symptoms and to normalize the heme pool.

The present inventors present a new therapeutic rational in the treatment of AIP, a rationale using PBGD, preferably recombinant human PBGD (rhPBGD), in order to reduce circulating high levels of PBG in serum by metabolizing (by enzymatic conversion) PBG to hydroxymethylbilane (HMB), which is the normal product of the reaction. This substitution therapy will lead to a normalization of PBG in serum as well as to a normalization of the heme pool. It will also lead to a normalization of ALA in serum, since these heme precursors are in equilibrium with each other. A lowering of serum ALA and PBG is expected to result in a concomitant relief of symptoms. The product of the reaction (HMB) will diffuse back into the cells and enter the normal heme biosynthetic pathway and will become subsequently metabolized to heme.

Alternatively investigations in treating the porphyrias have also suggested gene therapy, thus aiming at introducing genetic material in relevant cells, which will then take over the in vivo production of the enzyme of interest.

Hence, PBGD administered by injections will carry out its normal catalytic function by converting PBG to HMB in serum (extracellulary, not inside the cells). The new therapeutic idea is based on the assumption that ALA, PBG and HMB permeate cellular membranes or is transported specifically across them. An alternative to this is to administer a form of PBGD, which will be able to act intracellulary, either as a consequence of formulation or as consequence of modification of PBGD so as to facilitate its entry into cells from the extracellular compartment.

The observation that AIP patients have large amounts of these heme precursors in the serum supports the idea that PBG does not accumulate intracellularly, but is released from the cells into serum when the intracellular concentration increases due to the PBGD enzymatic block.

The basic new therapeutic concept for AIP is valid for all porphyrias and therefore the invention is in general aimed at treating these diseases by substituting the reduced or missing enzymatic activity characterizing the porphyrias.

Hence, in its broadest aspect, the invention pertains to a method for treatment or prophylaxis of disease caused by deficiency, in a subject, of an enzyme belonging to the heme biosynthetic pathway, the method comprising administering, to the subject, an effective amount of a catalyst which is said enzyme or an enzymatically equivalent part or analogue thereof.

Hence, by the term "catalyst" is herein meant either the relevant enzyme which is substituted as it is, or an enzymatically equivalent part or analogue thereof. One example of an enzymatically equivalent part of the enzyme could be a domain or subsequence of the enzyme which includes the necessary catalytic site to enable the domain or subsequence to exert substantially the same enzymatic activity as the full-length enzyme or alternatively a gene coding for the catalyst.

An example of an enzymatically equivalent analogue of the enzyme could be a fusion protein which includes the catalytic site of the enzyme in a functional form, but it can also be a homologous variant of the enzyme derived from another species. Also, completely synthetic molecules that mimic the specific enzymatic activity of the relevant enzyme would also constitute "enzymatic equivalent analogues".

In essence, the inventive concept is based on the novel idea of substituting the reduced enzymatic activity in the subject simply by administering a catalyst which will "assist" the enzyme which is in deficit. The precise nature, however, of the catalyst is not all-important. What is important is merely that the catalyst can mimic the enzymatic in vivo activity of the enzyme.

The term "the heme biosynthetic pathway" refers to the well-known enzymatic steps (cf. e.g. Sassa S. 1996, Blood Review, 10, 53–58) which leads from glycin and succinyl-CoA to heme, and enzymes belonging to this synthetic pathway are delta-aminolevulininic acid synthetase, delta-aminolevulinic acid dehydratase, porphobilinogen deaminase, uroporphyrinogen III cosythetase, uroporphyrinogen decarboxylase, coproporphyrinogen oxidase, protoporphyrinogen oxidase and ferrochelatase. Hence, in line with the above, a catalyst used according to the invention is such an enzyme or an enzymatically equivalent part or analogue thereof. It should be noted that the genes encoding all of the above-mentioned enzymes have been sequenced, thus allowing recombinant or synthetic production thereof.

The diseases related to reduced activity of these enzymes are acute intermittent porphyria (AIP), ALA deficiency porphyria (ADP), Porphyria cutanea tarda (PCT), Hereditary coproporphyria (HCP), Harderoporphyria (HDP), Variegata porphyria (VP), Congenital erthropoietic porphyria (CEP), Erythropoietic protoporphyria (EPP), and Hepatoerythropoietic porphyria (HEP).

By the term "effective amount" is herein meant a dosage of the catalyst which will supplement the lack or deficiency of enzymatic activity in a subject suffering from porphyria caused by reduced activity of one of the above-mentioned enzymes. The precise dosage constituting an effective amount will depend on a number of factors such as serum half-like of the catalyst, specific activity of the catalyst etc. but the skilled person will be able to determine the correct dosage in a given case by means of standard methods (for instance starting out with experiments in a suitable animal model such as with transgenic animals so as to determine the correlation between blood concentration and enzymatic activity).

The disease which is the preferred target for the inventive method is AIP, and therefore the catalyst is PBGD or an enzymatically equivalent part or analogue thereof. It is most preferred that the catalyst is a recombinant form of the enzyme belonging to the heme biosynthetic pathway or of the enzymatically equivalent part or analogue thereof, since recombinant production will allow large-scale production which, with the present means available, does not seem feasible if the enzyme would have to be purified from a native source.

Preferred formulations and dosage forms of the catalyst are exemplified for, but not limited to, PBGD in the detailed description hereinafter, and these formulations also are apparent from the claims. It will be appreciated that these formulations and dosage forms are applicable for all catalysts used according to the invention.

One important embodiment of the method of the inventions in one wherein the catalyst, upon administration, exerts at least part of its enzymatic activity in the intracellular compartment. This can e.g. be achieved when the catalyst is an enzymatically equivalent part or analogue of the enzyme, since such variations of the enzyme can be tailored to render them permeate cell membranes. Hence, when the catalyst is a small artificial enzyme or an organic catalyst which can polymerize porphobilinogen to hydroxymethylbilane, it should be possible for the skilled man to introduce relevant side chains which facilitates entry into the intracellular compartment. Alternatively, the catalyst is the enzyme, but formulated in such a manner that it exerts at least part of its enzymatic activity intracellularly upon administration to the subject. This can be achieved by tagging the enzyme with specific carbohydrates or other liver cell specific structures for specific liver uptake, i.e. the enzyme (or analogue) is modified so as to facilitate active transport into e.g. liver cells.

Although the above embodiments are interesting, it is believed that the normal, practical embodiment of the invention will involve use of a catalyst which exerts substantially all its enzymatic activity extracellularly in the bloodstream, since it is believed that the metabolic products of the enzymatic conversion of the relevant heme precursor will permeate freely into the intracellular compartment where the remaining conversions of the heme biosynthetic pathway can take place. Alternatively, the metabolic product may be excreted from the subject via urine and/or faeces at least to some extent.

As mentioned above, it is preferred that the catalyst is produced recombinantly, i.e. by a method comprising
a) introducing, into a suitable vector, a nucleic acid fragment which includes a nucleic acid sequence encoding the catalyst;
b) transforming a compatible host cell with the vector;
c) culturing the transformed host cell under conditions facilitating expression of the nucleic acid sequence; and
d) recovering the expression product from the culture and optionally subjecting the expression product to post-translational processing, such as in vitro protein refolding, enzymatic removal of fusion partners, alkylation of amino acid residues, and deglycosylation, so as to obtain the catalyst.

For relatively small catalysts (e.g. those constituted mainly of the active site of the enzyme), the catalyst can alternatively be prepared by liquid-phase or solid-phase peptide synthesis.

A more detailed explanation of the recombinant production of the model enzyme PBGD is given in the detailed section hereinafter, but as mentioned herein the same considerations apply for all other peptide catalysts of the invention. One of the main advantages of producing the catalyst by recombinant or synthetic means is, that if produced in a non-human cell, the catalyst is free from any other biological material of human origin, thus reducing problems with known or unknown pathogens such as viruses etc.

The dosage regiment will normally be comprised of at least one daily dose of the catalyst, (preferably by the intravenous route). Normally 2, 3, 4 or 5 daily dosages will be necessary, but if sustained release compositions are employed, less than 1 daily dosage are anticipated.

The daily dosage should be determined on a case by case basis by the skilled practitioner, but as a general rule, the daily dosage will be in the range between 0.01–1.0 mg/kg body weight per day of the catalyst. More often the dosage will be in the range of 0.05–0.5 mg/kg body weight per day, but is should never be forgotten that precise dosage depends on the dosage form and on the activity of the catalyst as well as on the degree of deficiency of the relevant enzyme or combinations of enzymes and an individualized treatment, where the dose is adjusted to normalize patient serum and urine precursor levels.

The most correct way of determining the correct dosage is based on the patient specific precursor levels. The precursor being the product of the enzymatic reaction.

For PBGD, the daily dosage is about 0.08–0.2 mg per kg body weight per day, and most often 0.1 mg per kg body weight per day will be the dosage of choice. It is believed that comparable dosages will be applicable for the other full-length enzymes or combinations of enzymes.

Finally, as will be appreciated from the above disclosure, the invention is based on the novel idea of providing substitution for the enzymes lacking in activity. To the best of the knowledge of the inventors, therapeutic use of catalysts having such effects have never been suggested before, and therefore the invention also pertains to a catalyst as defined herein for use as a pharmaceutical. Furthermore, use of such catalysts or combination of different catalysts for the preparation of pharmaceutical compositions for treatment of the above-discussed disease is also part of the invention.

LEGENDS TO FIGURES

FIG. 1: Circular map of plasmid pPBGD1.1

Figure 2:
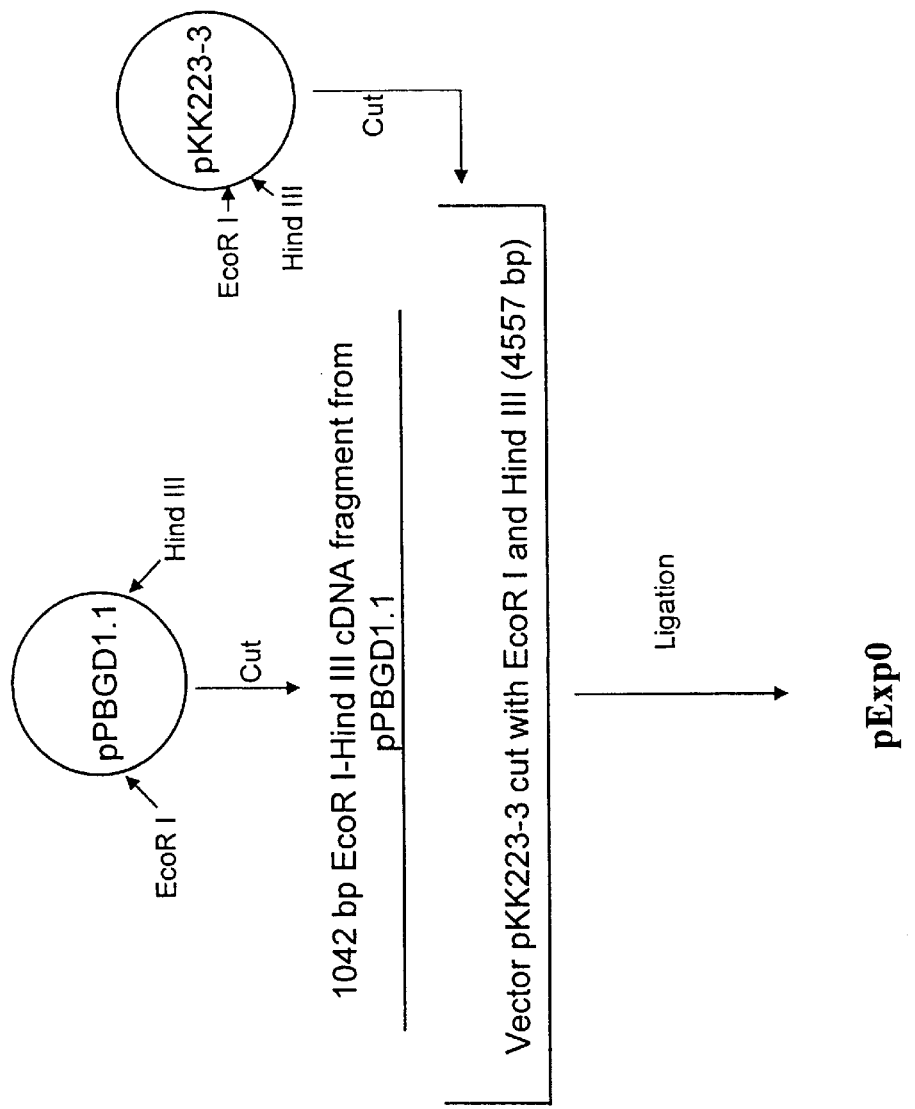

FIG. 2: Flow chart for construction of plasmid pExp0

Figure 3:
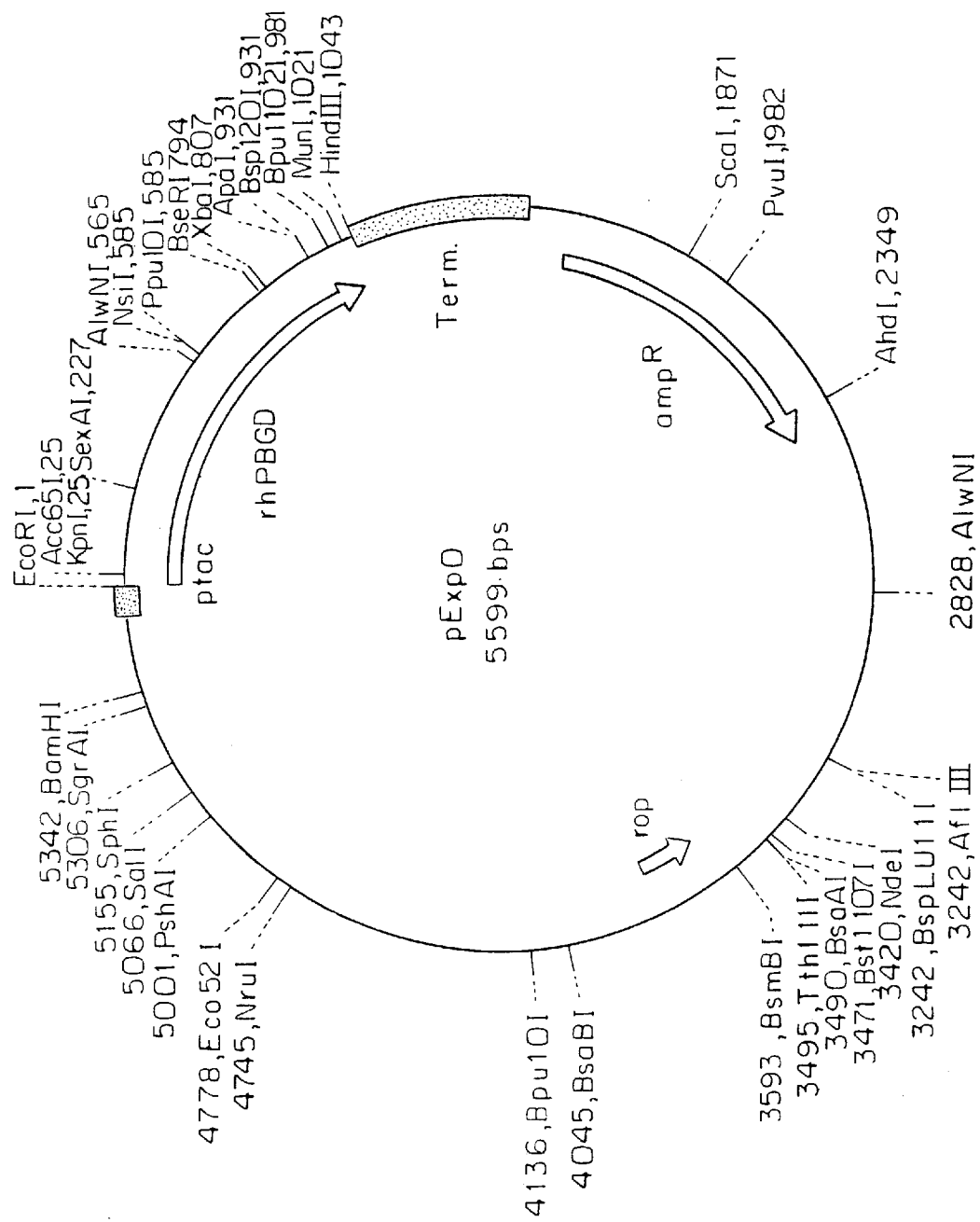

FIG. 3: Circular map of plasmid pExp0

Figure 4:
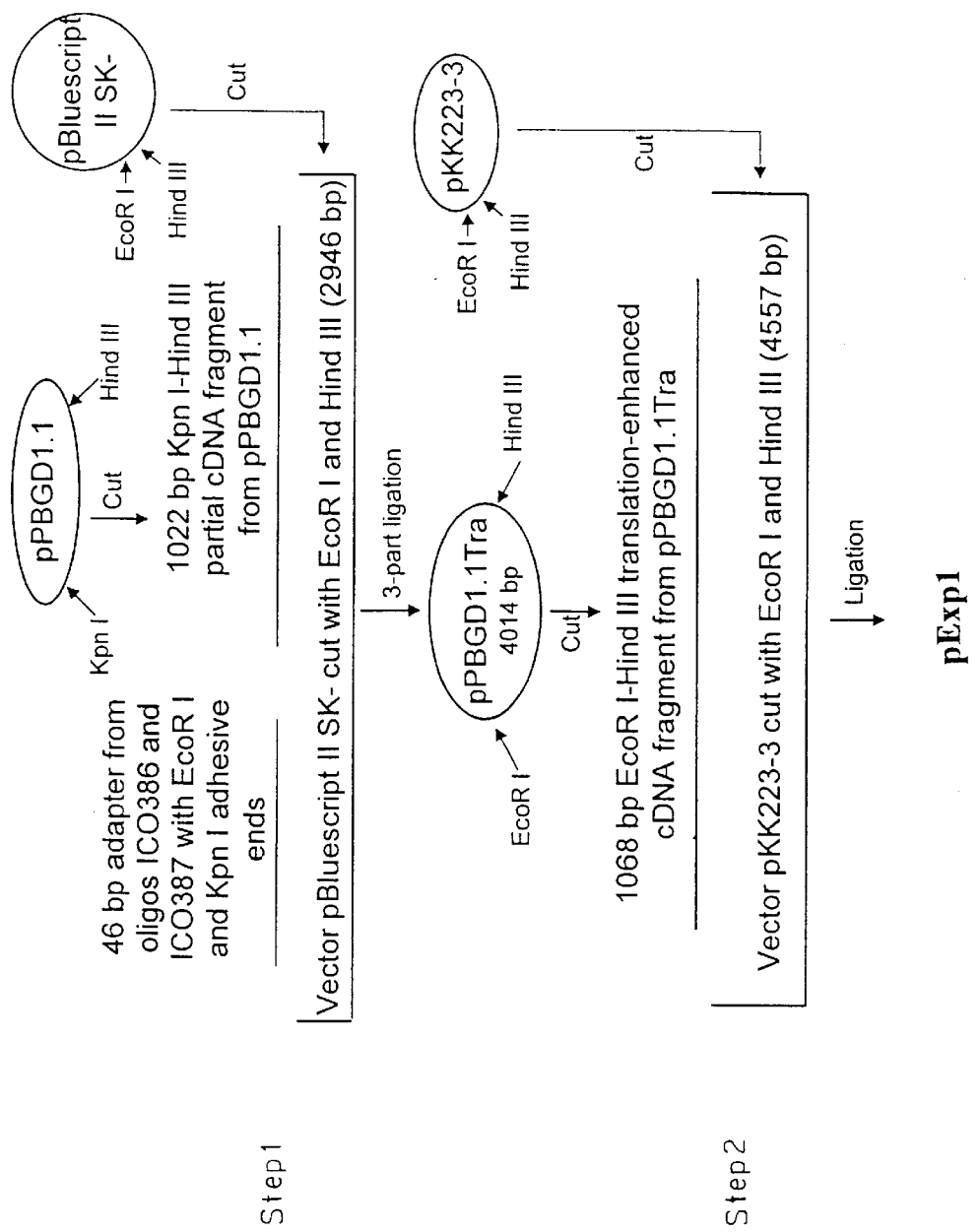

FIG. 4: Flow chart for construction of plasmid pExp1

Figure 5:
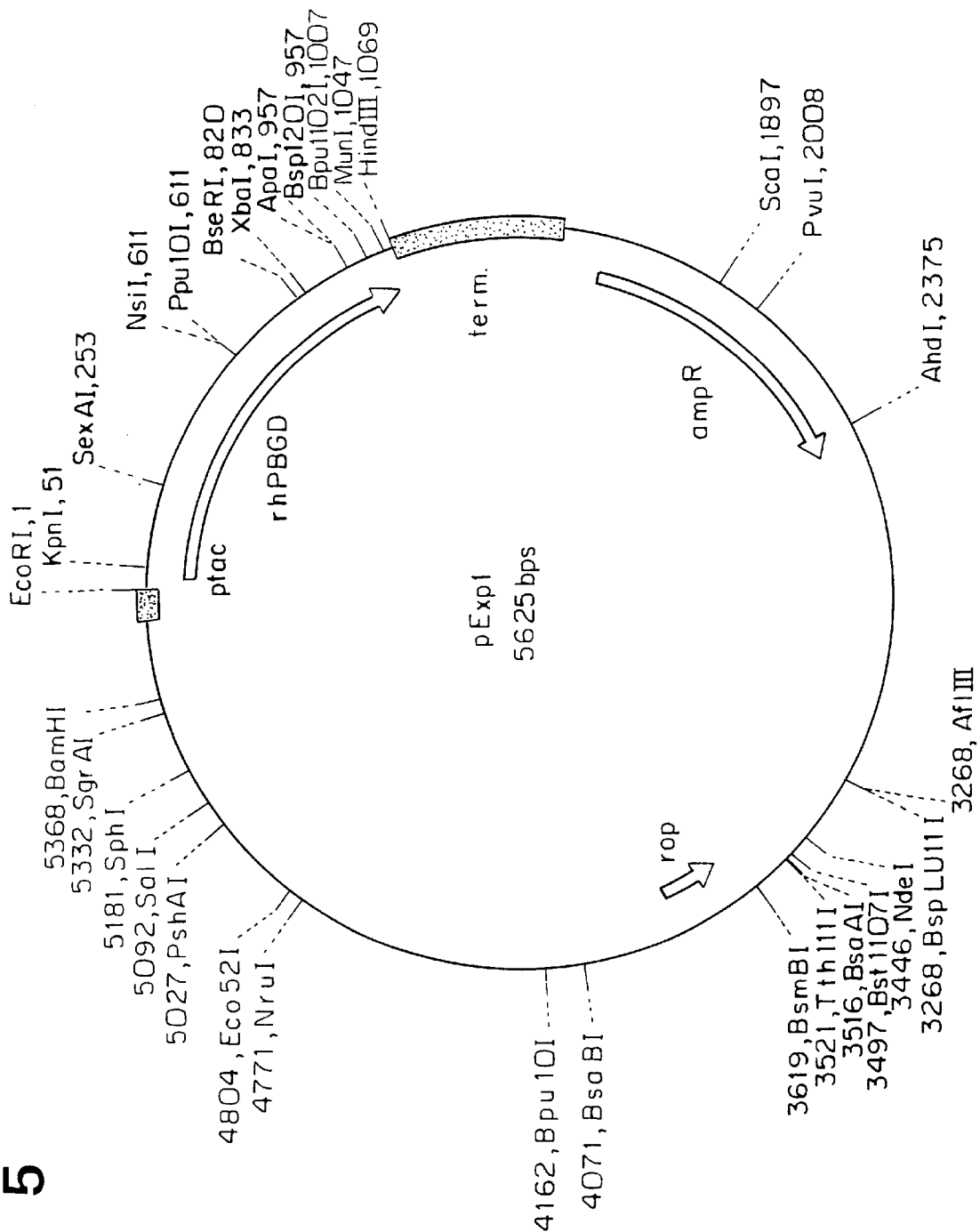

FIG. 5: Circular map of plasmid pExp1

Figure 6:
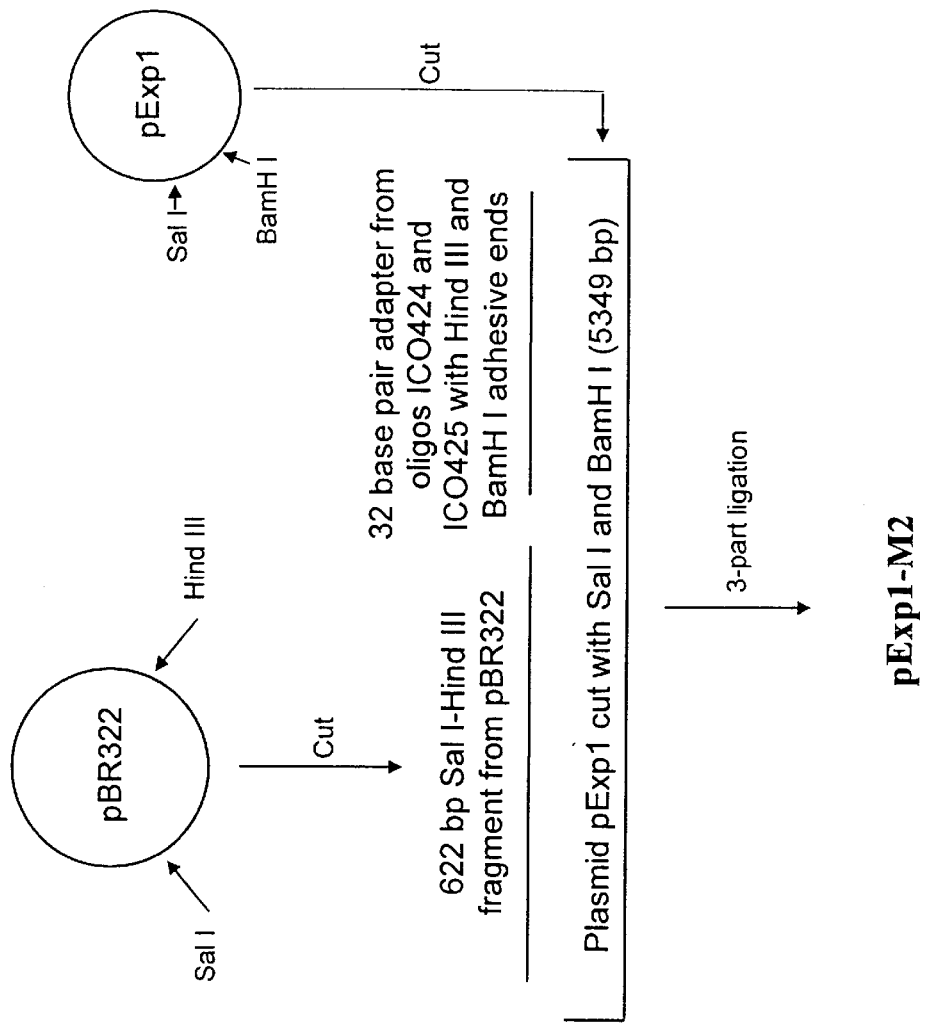

FIG. 6: Flow chart for construction of pExp1-M2

Figure 7:
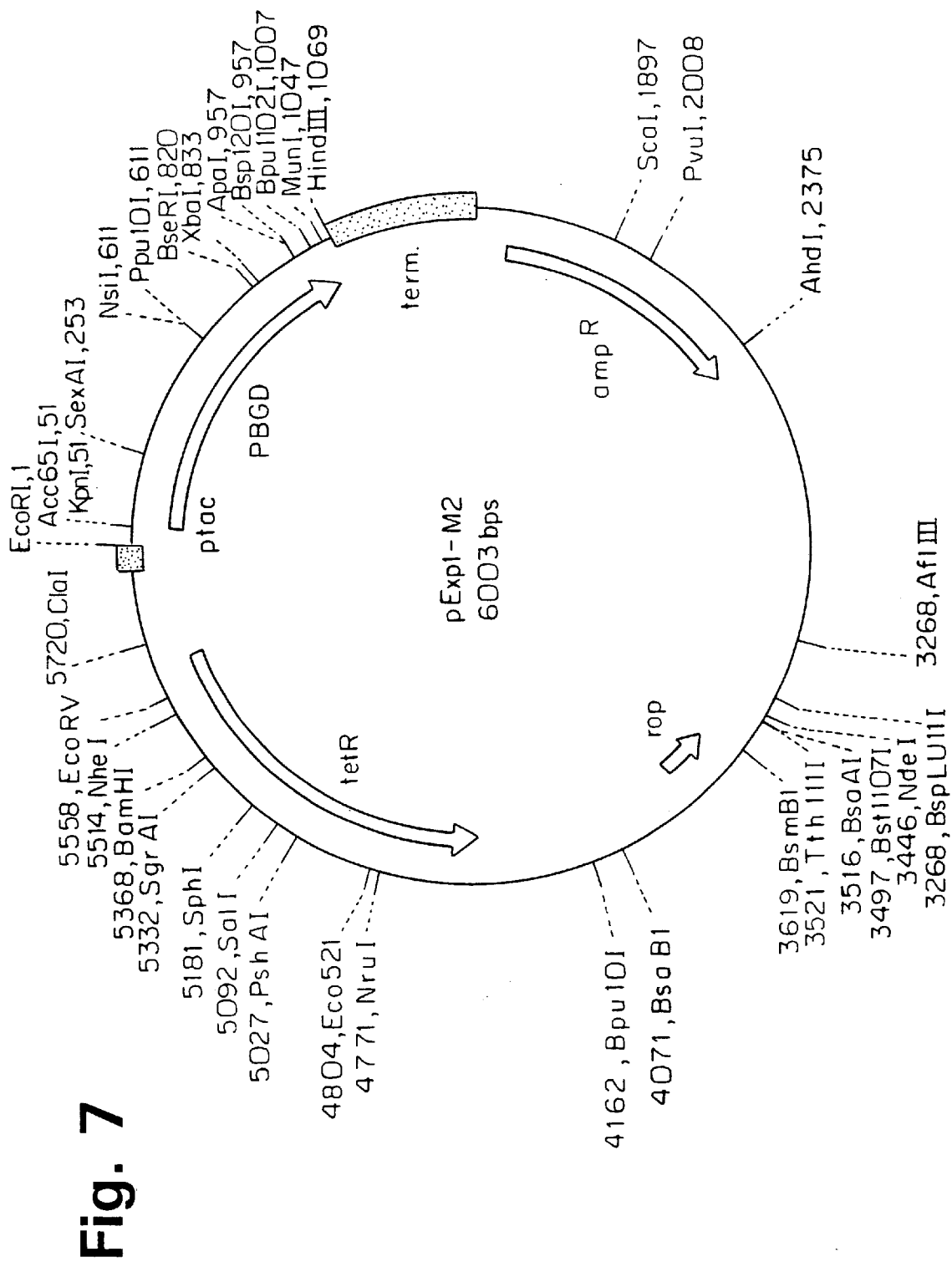

FIG. 7: Circular map of plasmid pExp1-M2

Figure 8:
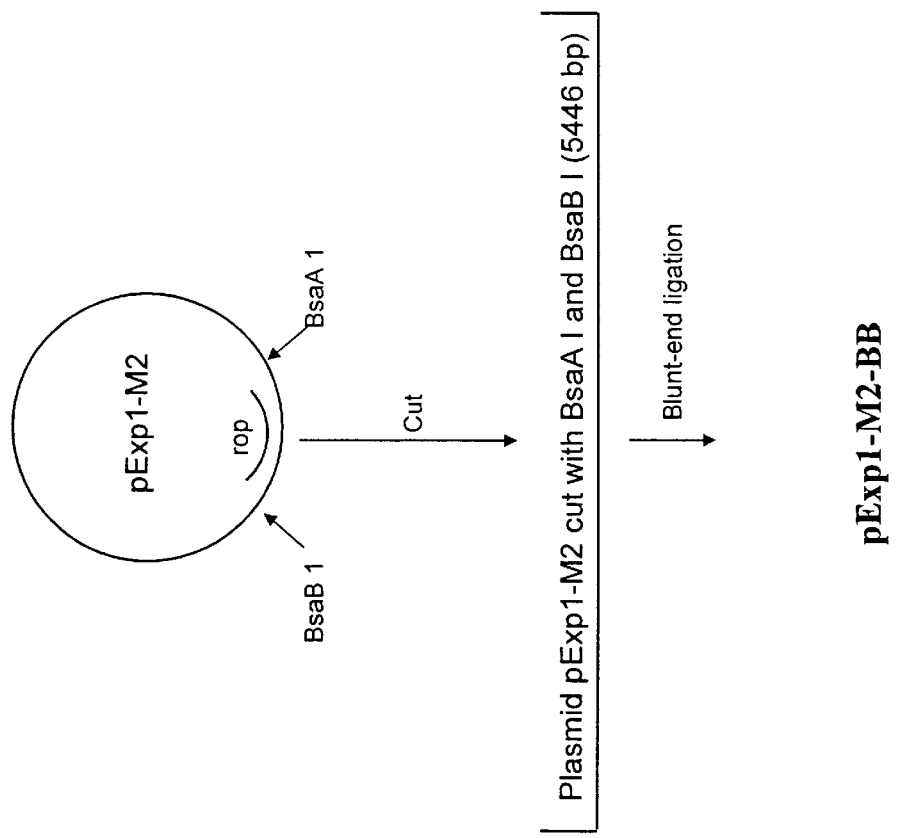

FIG. 8: Flow chart for construction of rhPBGD expression plasmid pExp1-M2-BB FIG. 9: Circular map of rhPBGD expression plasmid pExp1-M2-BB FIG. 10: PCR strategy for construction of the EcoR I-Hind III linear DNA-fragment FIG. 11: Structure of the EcoR I-Hind III linear DNA-fragment used for transformation FIG. 12: Respiration and growth data from fermentation PD14 with strain PBGD-2

Figure 13:
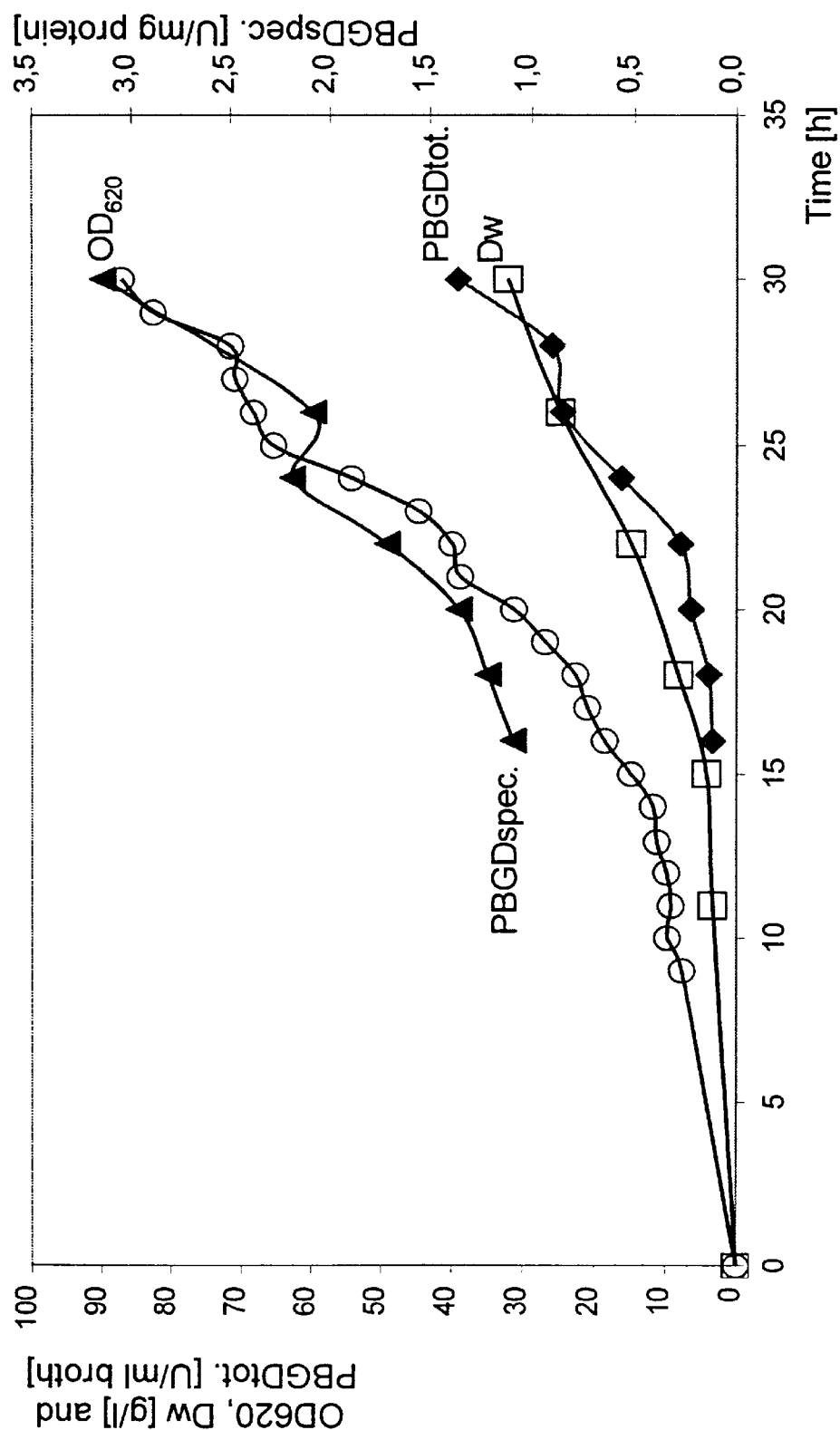

FIG. 13: rhPBGD expression in fermentation PD14 with strain PBGD-2

Figure 14:
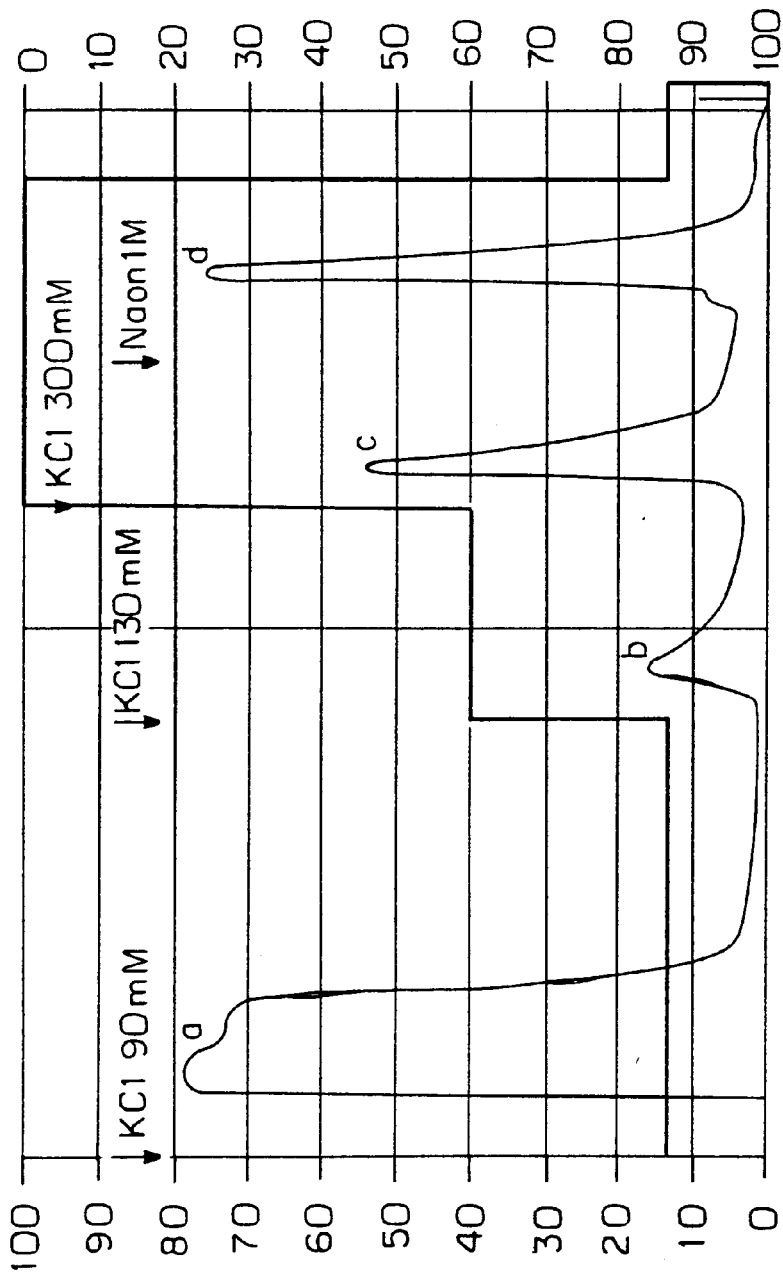

FIG. 14: Chromatography on DEAE-Sepharose FF (DEAE1)

Figure 15:
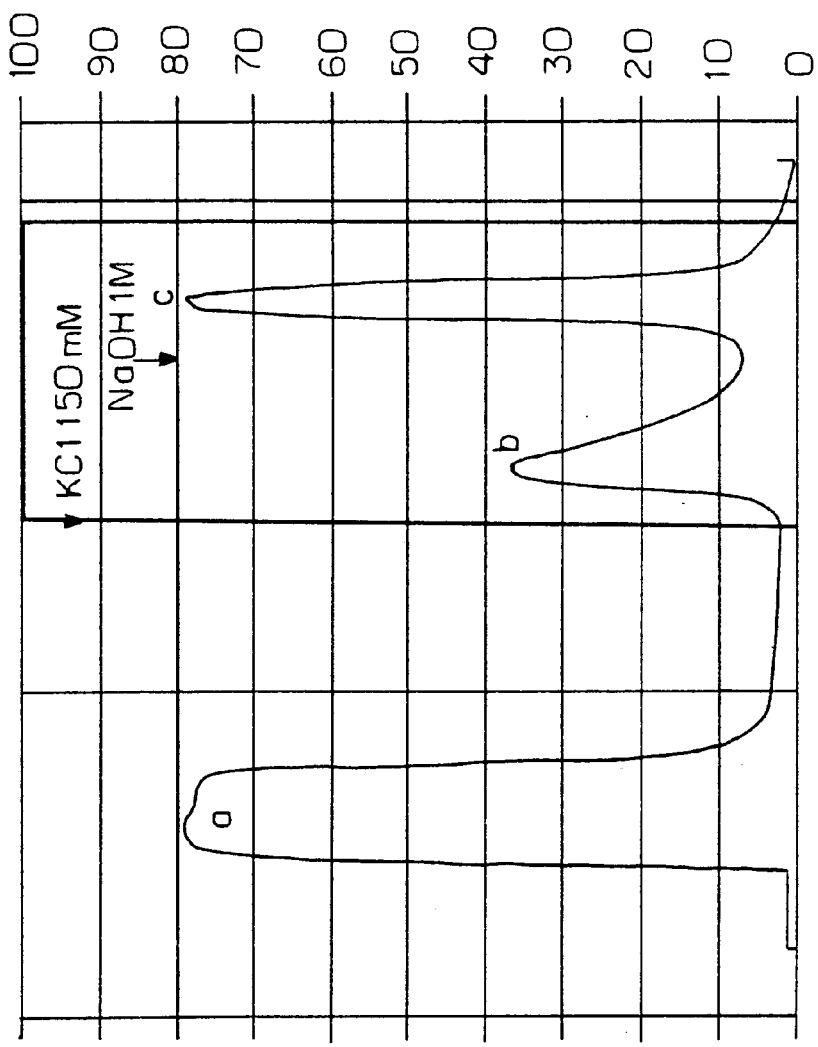

FIG. 15: Chromatography on DEAE-Sepharose FF (DEAE2)

Figure 16:
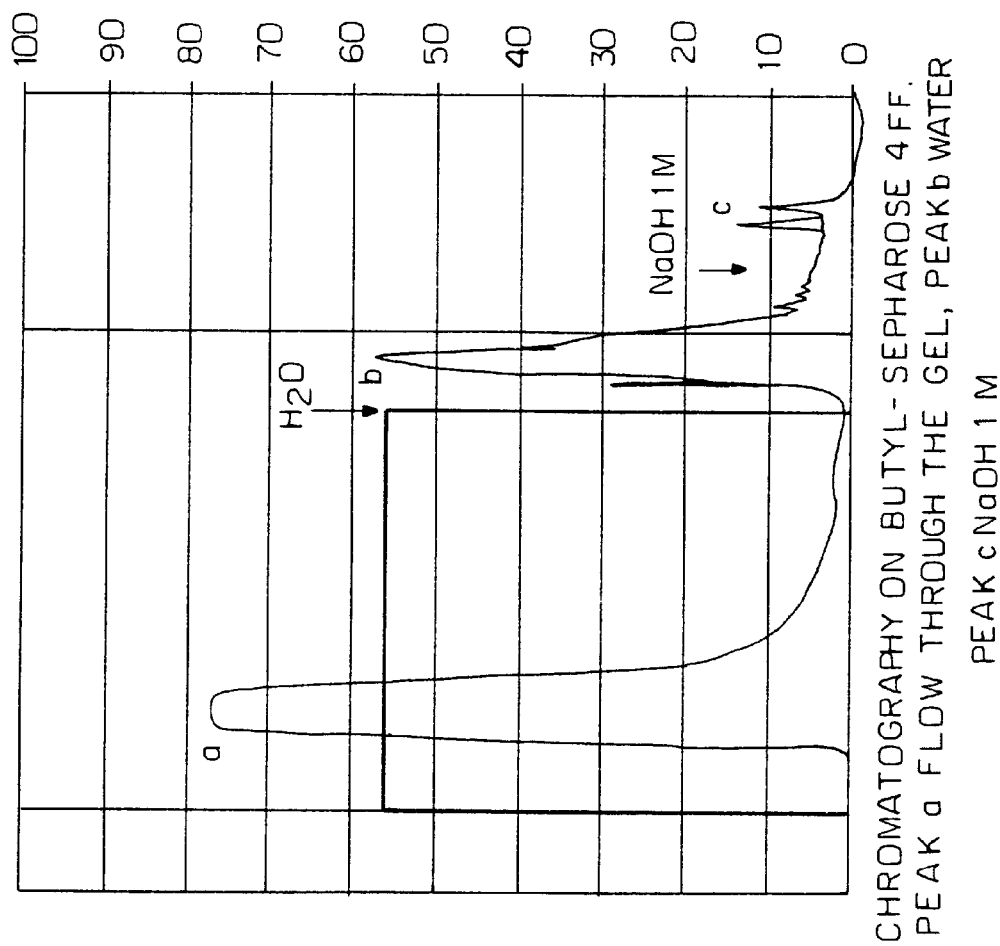

FIG. 16: Chromatography on Butyl-Sepharose 4 FF

Figure 17:
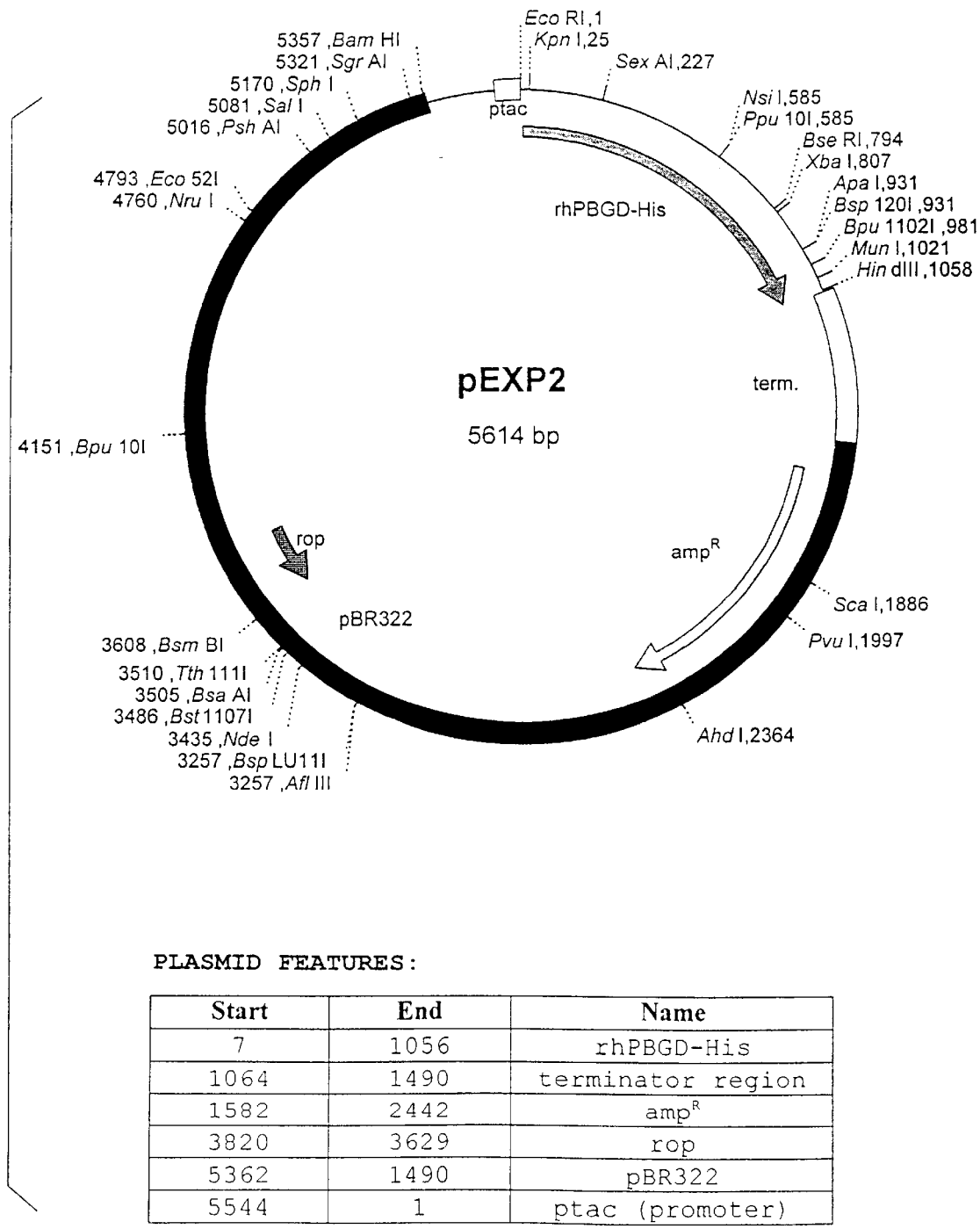

FIG. 17: Circular map of rhPBGD-His expression plasmid pExp2

Figure 18:
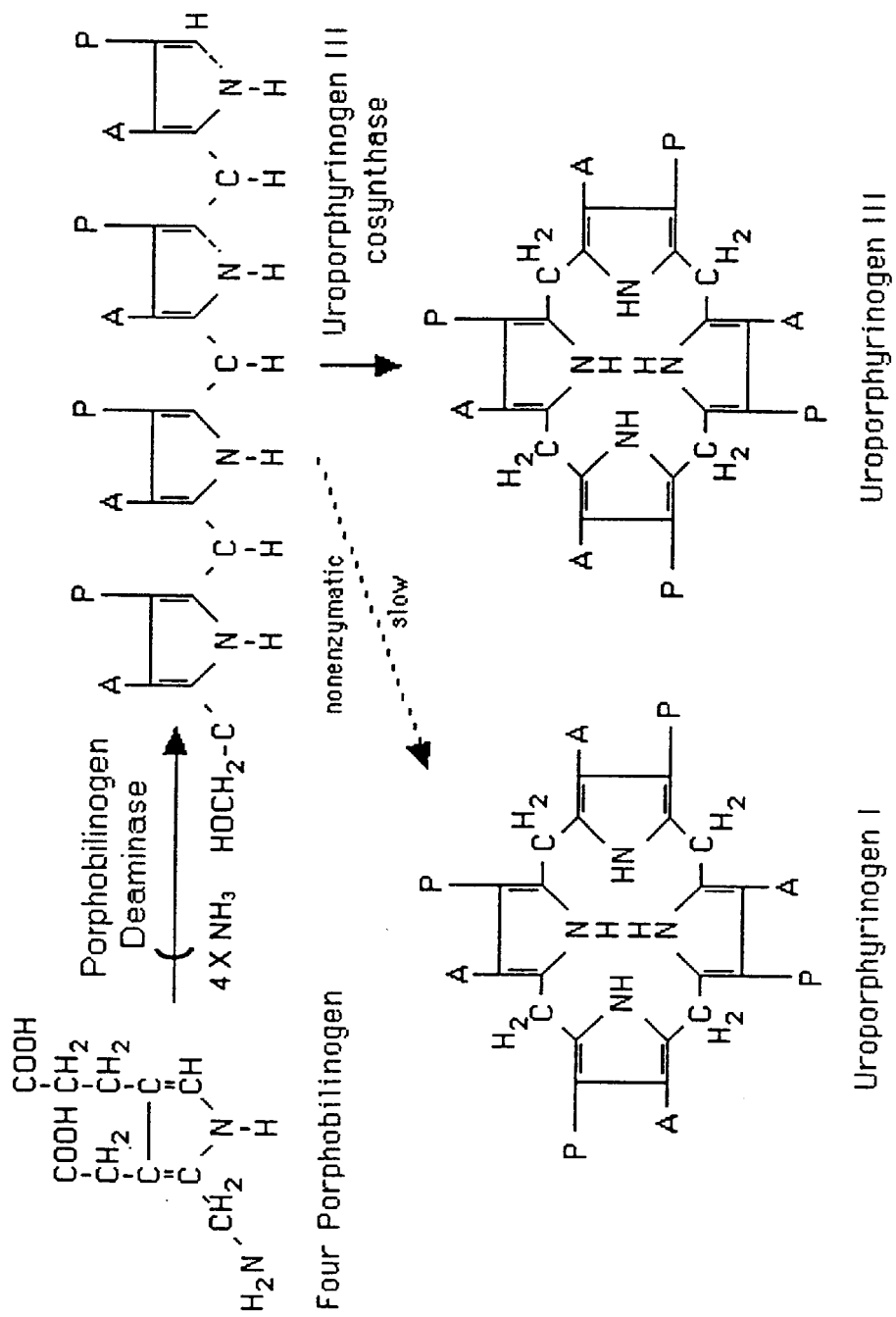

FIG. 18: PBGD reaction mechanism

Figure 19:
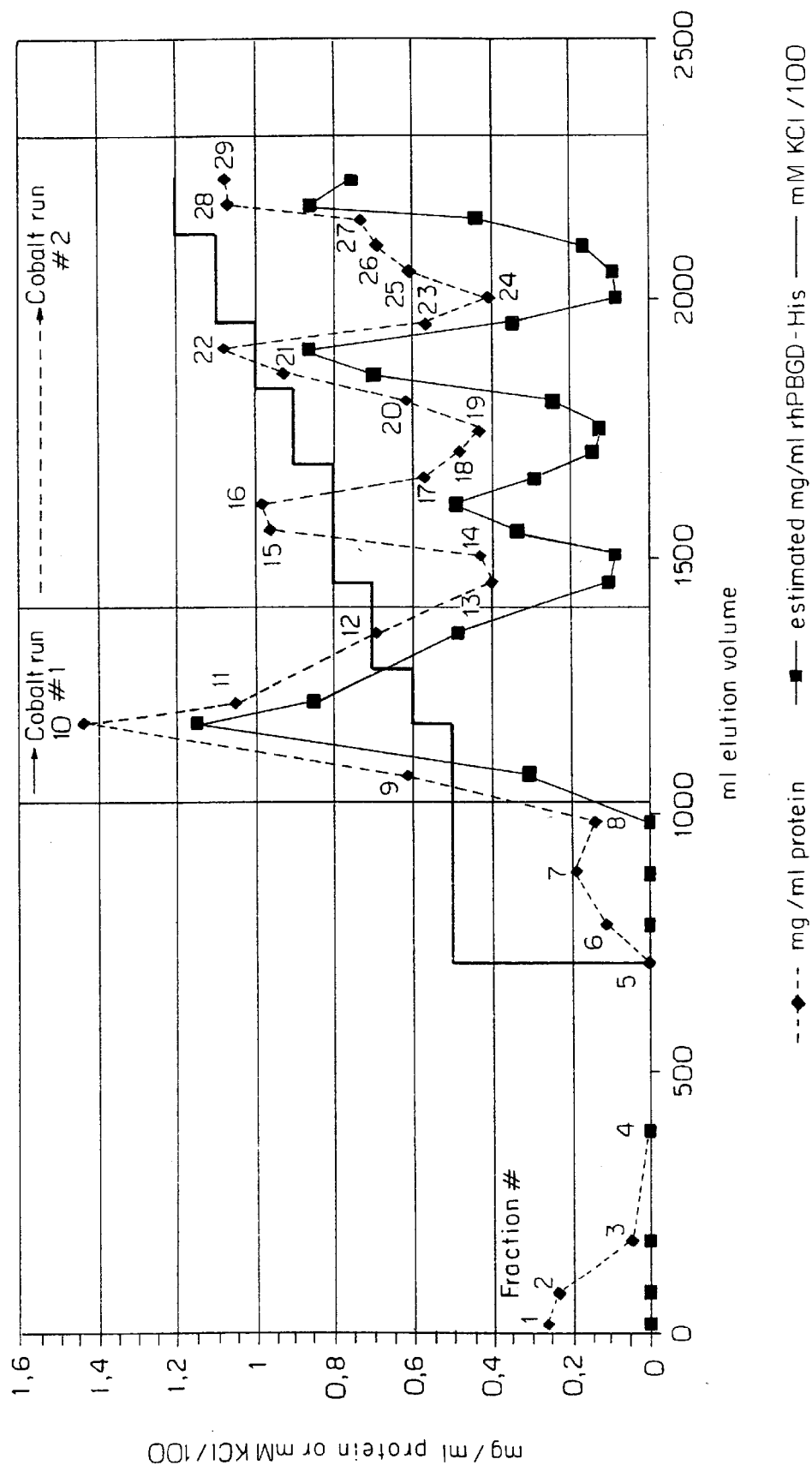

FIG. 19: DEAE chromatography elution profile

Figure 20:
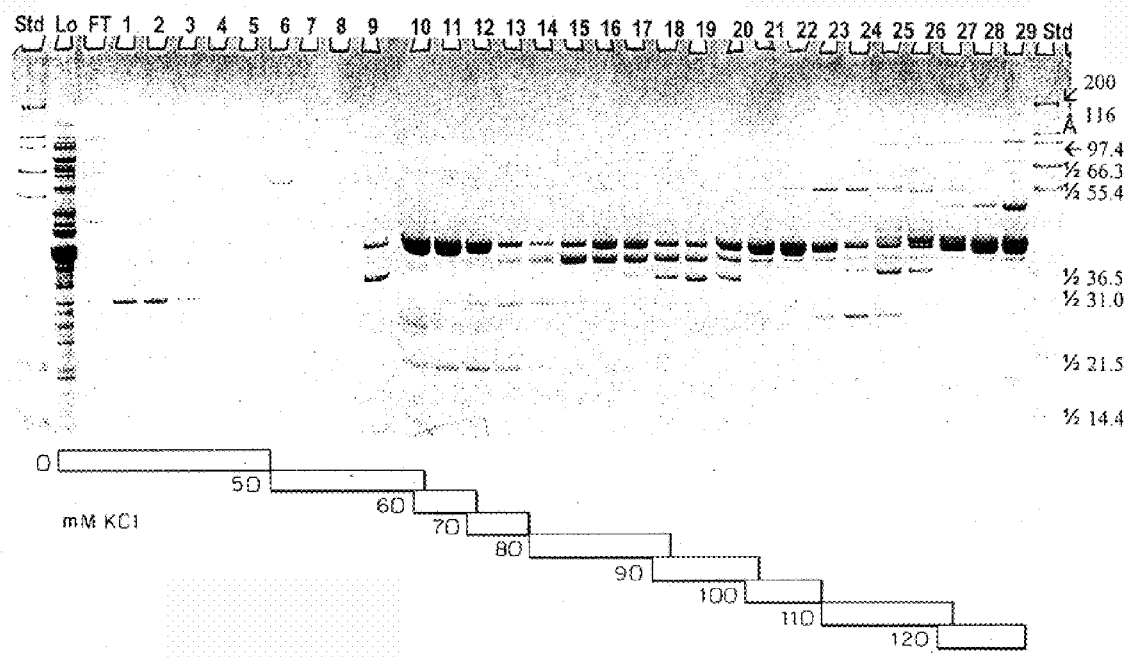

FIG. 20: SDS-PAGE gel of DEAE eluates

Figure 21:
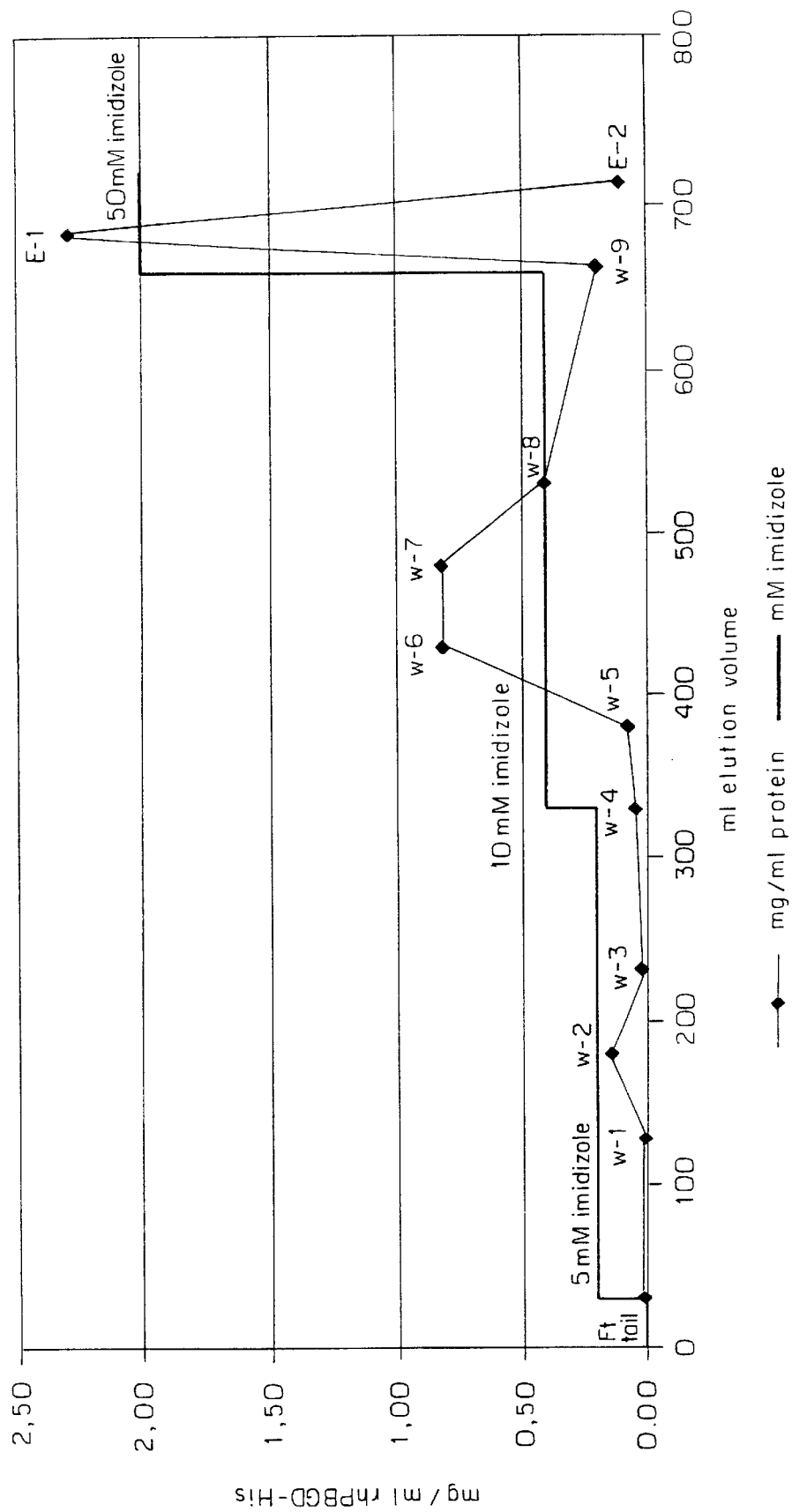

FIG. 21: Cobalt chromatography elution profile

Figure 22:
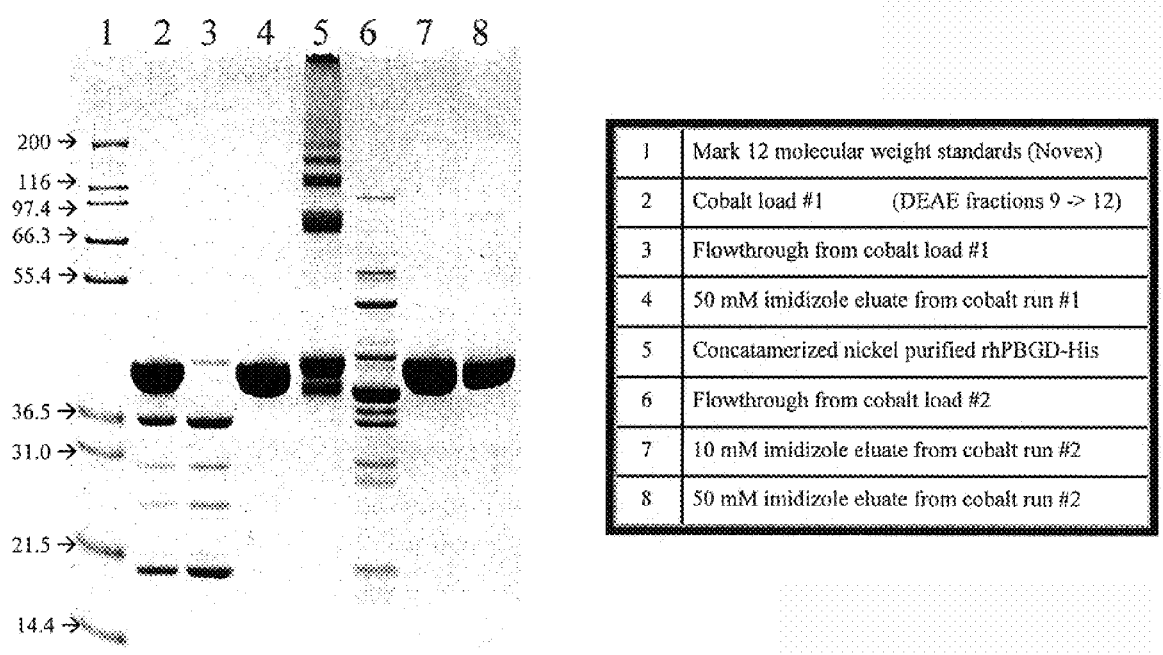

FIG. 22: SDS-PAGE gel results of cobalt eluates

SEQUENCE LIST

Seq. ID NO 1: Sequence of the expression plasmid pExp1-M2-BB

Seq. ID NO 2: Sequence of the EcoR I-Hind III linear fragment used for transformation in the hemC disruption strategy Seq. ID NO 3: Sequence of the erythropoietic form (PBGD 1.1)

Seq. ID NO 4: Sequence of the non-erythropoietic form (PBGD 1.1.1)

Seq. ID NO 5: Sequence of PDGB from Spleen (PBGD 1.3)

Seq. ID NO 6: Sequence of PDGB from bone marrow (PBGD 2.1)

Seq. ID NO 7: Sequence of PDGB from bone marrow (PBGD 2.2)

Seq. ID NO 8: Sequence of PDGB from lymph node (PBGD 3.1)

Seq. ID NO 9: Sequence of PDGB from lymph node (PBGD 3.3)

Seq. ID NO 10: Sequence PDGB from total brain (PBGD 5.3)

Seq. ID NO 11: Sequence of PDGB from total brain (PBGD 6.1)

DETAILED DISCLOSURE OF THE INVENTION

In a first embodiment of the invention relates to a method for treatment or prophylaxis of disease caused by deficiency, in a subject, of one or more enzymes belonging to the heme biosynthetic pathway, the method comprising administering, to the subject, an effective amount of a catalyst which is said enzyme or combination of enzymes or an enzymatically equivalent part or analogue thereof. The disease may be selected from the phorphyria group and the catalyst may be an enzyme selected from the group consisting of delta-aminolevulinic acid dehydratase (ALAD), porphobilinogen deaminase (PBGD), uroporphyrinogen III cosythetase, uroporphyrinogen decarboxylase, coproporphyrinogen oxidase, protoporphyrinogen oxidase, and ferrochelatase, or an enzymatically equivalent part or analogue thereof.

The invention also relates to any combination of the enzymes mentioned above because one enzymatic deficiency may cause such alterations of the pathway that alternative enzymatic reactions are needed wherein an otherwise normal production of an enzyme for such alternative pathway is not sufficient. In alternative, the disease relating to the heme biosynthetic pathway may also be due to a deficiency of more than only one enzyme. Accordingly, en the present context the term catalyst may also be interpreted as a combination of catalyst and the term enzyme may also include a mixture of different enzymes.

In a preferred embodiment, the disease is AIP and the enzyme is PBGD or an enzymatically equivalent part or analogue thereof optionally in combination with ALAD. In a further embodiment, the catalyst is a recombinant form of the enzyme belonging to the heme biosynthetic pathway or of the enzymatically equivalent part or analogue thereof.

The catalyst may be administered by a route selected from the group consisting of the intravenous route, the intraarterial route, the intracutaneous route, the subcutaneous route, the oral route, the buccal route, the intramuscular route, the anal route, the transdermic route, the intradermal route, and the intratechal route.

The catalyst is preferable formulated in an isotonic solution, such as 0.9% NaCl and 10–50 mM sodium phosphate pH 7.0+/−0.5 up to pH 8.0 or sodium phosphate, glycine, mannitol or the corresponding potassium salts. The catalyst may also be lypohilized, sterile filtered, and in a further embodyment formulated as lipid vesicles comprising phosphatidylcholine or phosphatidylethanolamine or combinations thereof. In a still other embodiment the catalyst is incorporated into erthrocyte ghosts.

Also a sustained release formulation may be performed involving biodegradable microspheres, such as microspheres comprising polylactic acid, polyglycolic acid or mixtures of these.

A further method according to the invention is wherein the catalyst is lyophilized in a two-compartment cartridge, where the catalyst will be in the front compartment and water for reconstitution in the rear compartment. The two compartment cartridge may be combined with an injection device to administer the catalyst either by a needle or by a needle-less (high pressure) device.

It may also be very convenient to administer the catalyst in a formulation of a physiological buffer containing an enhancer for nasal administration.

Other formulations for the catalyst include an oral formulation containing lipid vesicles, such as those comprising phospatidylcholine, phosphatidylethanolamine, or sphingomyeline, or dextrane microspheres.

The formulation is preferable one that is able to enhance the half-life of the catalyst in the subject's bloodstream. This may be use of a formulation wherein the catalyst has a polyethylene glycol coating.

The catalyst may also be complexed with a heavy metal.

In a further aspect the catalyst is an enzymatically equivalent part or analogue of the enzyme and exerts at least part of its enzymatic activity intracellularly upon administration to the subject. This may be when the catalyst is a small artificial enzyme or an organic catalyst that can polymerise porphobilinogen to hydroxymethylbilane.

Furthermore, the catalyst may be said enzyme formulated in such a manner that it exerts at least part of its enzymatic activity intracellularly upon administration to the subject.

In addition the catalyst may be tagged with specific carbohydrates or other liver cell specific structures for specific liver uptake.

In a further aspect the catalyst exerts substantially all its enzymatic activity extracellulary in the bloodstream.

In a still further aspect, the enzymatic activity of the catalyst on its relevant heme precursor results in a metabolic product which 1) either moves into the intracellular compartment and is converted further via the remaining steps of the heme biosynthetic pathway or 2) is excreted from the subject via urine and/or faeces.

A further embodiment of the invention relates to a method wherein the catalyst has been prepared by a method comprising
a) introducing, into a suitable vector, a nucleic acid fragment which includes a nucleic acid sequence encoding the catalyst;
b) transforming a compatible host cell with the vector;
c) culturing the transformed host cell under conditions facilitating expression of the nucleic acid sequence; and
d) recovering the expression product from the culture and optionally subjecting the expression product to post-translational processing, such as in vitro protein refolding, enzymatic removal of fusion partners, alkylation of amino acid residues, and declycosylation, so as to obtain the catalyst.

The catalyst may be prepared by liquid-phase or solid-phase peptide synthesis and it is preferable free from any other biological material of human origin.

As mentioned above the catalyst may be administered at least once a day, such as 2, 3, 4, and 5 times daily depending on the specific treatment regimen outlined for the patient in that precursor levels for each patient are measured before and/or during treatment for evaluation of the specific dosage.

Accordingly the daily dosage may be in the range of 0.01–1.0 mg/kg body weight per day, such as in the range of 0.05–0.5 mg/kg body weight per day. And the present invention also relates to the use of the catalyst for the preparation of a pharmaceutical composition.

It is estimated that a dosage will often be about 0.1 mg per kg body weight per day.

Accordingly, the invention also relates to a catalyst which is an enzyme of the heme biosynthetic pathway or an enzymatically equivalent part or analogue thereof, for use as a medicament. Thus in a further embodiment, the invention relates to a catalyst which is an enzyme of the heme biosynthetic pathway of an enzymatically equivalent part or analogue thereof for the preparation of a pharmaceutical composition for the treatment or prophylaxis of diseases caused by deficiency of said enzyme.

Naturally, the catalyst may be a recombinant form of the enzyme. An example is a recombinant human PBGD based on any of Seq. ID NO 3 and Seq. ID NO 4.

In a preferred embodiment and as will be disclosed in detail below, the invention also relates to a method for treating a patient having a mutation in the PBGD gene causing an enzyme defect, the method comprising use of a human PBGD cDNA sequence of either non-erythropoietic form or erythropoietic form according to the tissue in which PBGD should be expressed, and transfecting the patient with the relevant cDNA. Preferably the enzyme deficiency is selected from enzyme deficiencies resulting in a disease selected from Acute intermittent porphyria, (AIP), ALA deficiency porphyria (ADP), Porphyria cutanea tarda (PCT), Hereditary coproporphyria (HCP), Harderoporphyria (HDP), Variegata porphyria (VP), Congenital erythropoietic porphyria (CEP), Erythropoietic protoporphyria (EPP), and Hepatoerythropoietic porphyria (HEP).

In a preferred embodiment, the human PBGD cDNA sequence is selected from Seq. ID NO 3 and Seq. ID NO 4.

The transfection may be by use of a vector selected from adenovirus, retrovirus and associated adenovirus. The PBGD gene transfer vector into human cells (erythropoietic and/or non-erythropoietic) preferable results in normal PBGD activity or in an activity wherein the patient is free of symptoms of disease.

A further method of gene therapy treatment of patients with Acute Intermittent Porphyria (AIP) according to the invention is by a correction of one of the specific point mutations identified causing AIP by use of chimeraplasty gene repair. This involve specific designed oligonucleotides and a specific knowledge of both the mutation to be corrected and to the sequence on both sides on the mutation.

In a specific embodiment of chimeraplasty gene repair is by use of a delivery system for transfection by use of a non-viral vectors formulated in a vehicle preparation comprising one or more components selected from cationic phospholipids, phospholipids, phospholipids mixed with neutral lipids, lictosylated PEI, liposomes liposomes comprising mixtures of natural phospholipids and neutral lipids.

The mutation may be selected from the mutation shown in Table A.

The following description of preferred embodiments of the invention will focus on recombinant production of PBGD and formulations and uses thereof. It will be appreciated, however, that all disclosures relating to this polypeptide apply also for the other enzymes mentioned above. Hence, production and use of PBGD only exemplifies the invention, but all other enzymes of the heme biosynthetic pathway can substitute PBGD in the embodiments described hereinafter.

Production of Recombinant Human PBGD (rhPBGD)

As mentioned above, it is preferred to administer recombinant human versions of the various enzymes of the heme biosynthetic pathway. In the following will be described recombinant production of one of these enzymes, namely PBGD.

The gene for the erythropoietic PBGD, which is located in the human genome in the chromosomal region 11q 24, is composed of 15 exons spanning 10 kb of DNA and is shown in Grandchamp B. et al. 1996, J. of Gastroenerology and Hepatology 11, 1046–1052.

The gene coding the erythropoietic PBGD enzyme (344 amino acids) (Raich N. et al 1986, Nucleic. Acid. Res, 14, 5955–5968), will be cloned from a human erythropoietic tissue by use of a nested PCR (polymerase chain reaction) strategy.

The PBGD coding region will be inserted in a plasmid and transformed into a suitable host cell (a bacterium such as *E. coli* and *B. subtilis,* or a fungus as Saccharomyces). The expression of the PBGD gene will be regulated by a promoter which is compatible with the selected host cell.

For bacterial production: An endogenous ATG sequence is located at the $NH_2$-terminal end of the PBGD structural gene for initiation of transition and cytoplasmic expression. Alternatively insert in front of the PBGD coding region a bacterial signal sequence for example an *E. coli* periplasmic enzyme signal peptide or a signal peptide from a secreted enterotoxin or endotoxin in *E. coli,* to obtain secretion in *E. coli.*

The plasmid used for production of rhPBGD in E. coli was constructed in the following way:

Construction of the Plasmid Harboring the Coding Region of Human Wild Type PBGD (pBPGD1.1)

Introduction:

The erythropoietic expressed form of porphobilinogen deaminase (PBGD) (Raich N. et al. Nucleic Acids Research 1986 14(15): 5955–67) was cloned and sequence determined. Two forms of PBGD are known. The erythropoietic form is expressed specifically in erythroid progenitors and the constitutive form is expressed in all cells (Grandchamp B. et al. 1987, Eur J Biochem. 162(1): 105–10). The two are expressed from the same gene and are identical except for the addition of 17 amino acids at the amino terminus of the constitutive form through alternative exon usage. It was decided to clone and express the erythropoietic form. There are three sequences for PBGD in the Genebank, the two isoforms mentioned above and the genomic sequence (Yoo H W. et al. 1993, Genomics, 15(1):21–9). These all have nucleotide differences translating to amino acid changes. Before choosing a specific sequence to be expressed for a human therapeutic it was therefore necessary to determine what is the wild type allele. To accomplish this, PBGD cDNA clones were isolated and sequences from a number of sources to define the most common amino acid usage. Oligonucleotide primers were designed to amplify the coding region from cDNAs by Polymerase Chain Reaction (PCR) (Saiki R. K. et al. 1985, Science 230(4732):1350–4). These were used to isolate cDNAs from 5 sources of mRNA which were then cloned into a plasmid vector. Eight of these clones were sequenced and along with the published sequences define a wild type allele, which should be the most common amino acid sequence in the population. This wild type allele will be used for protein expression.

Strategy:

A nested PCR strategy was devised to clone PBGD. The first primer set, (see Table 1) Ico379 and Ico382, are 20 mers that bind to sequences outside of the coding region. Ico379 is specific for the 5' untranslated region of the mRNA (cDNA) of the erythropoietic form of PBGD. The binding site is in an exon region not expressed in the constitutive form of the enzyme. Ico382 binds to the 3' untranslated region of both forms of PBGD. Internal to these are a second set of oligonucleotides primers to be used for the second round of PCR, Ico375 and Ico376, designed to distal ends of the PBGD coding region. Ico375 has 22 bases of sequence homologous to the 5' end of the coding region of the erythropoietic form of PBGD with the ATG start codon followed by an EcoR I endonuclease cleavage site for cloning of the PCR product and 4 bases of sequence to ensure efficient restriction. Ico376 has 33 based homologous to the 3' end of the PBGD coding region with 3 bases changed internally to introduce a Mun I/Mfe I endonuclease cleavage site through silent mutations and ending with the TAA stop codon. This restriction site will be used to easily introduce sequence encoding a His-Tag to the DNA with oligonucleotide adapters or to enable other 3' modifications. Following the stop codon is a second stop codon to ensure good termination of translation and a HindIII endonuclease cleavage site for cloning the PCR product followed by 4 bases to ensure efficient restriction. The EcoRI and HindIII endonuclease cleavage sites introduced onto the ends of the PBGD PCR product ligate into the respective unique restriction sites in the high copy number pBluescriptII SK-(Stratagene) vector for sequencing and will then be used to move the PBGD DNA into an E. coli expression vector for production of recombinant human porphobilinogen deaminase, rhPBGD.

PCR:

Six cDNAs were used as a PCR source; spleen, bone marrow, lymph node, lung, whole brain and adipose tissue each from a different pool of human donors (produced by Donald Rao using BRL Superscript II with 500 ng Clontech poly-A RNA in 20 $\mu$l reaction volumes per manufacturers instructions except adipose which was made from 5 $\mu$g of Clontech total RNA from a single donor). List of equipment and supplies used (see lists below). One $\mu$l of each cDNA (approximately 25 ng) was amplified with Advantage cDNA polymerase mix (Clontech) with 0.2 mM dNTP (PE/ABI) and 0.3 $\mu$M each of Ico379 and Ico382 in 50 $\mu$l reaction volumes. Two cycle PCR was used, with an initial heat denaturation step at 94° C. for 1'40" then 28 cycles of 96° C. for 16" and 68° C. for 2'. A final extension of 6'at 74° C. ensured that extension products were filled out. One fifth of the reaction was run out on a 1.2% agarose gel with 2 $\mu$l of 6X ficol loading dye in 0.5X TBE buffer (Maniatis T., E. F. Fritsch, J. Sambrook. Molecular Cloning (A laboratory Manual) Cold Spring Harbor Laboratory. 1982). The predicted band of 1.1 kb. was observed by ethidium bromide staining with all sources but lung tissue cDNA. These bands were excised and DNA was isolated with Microcon-30 with micropure inserts (Amicon/Millipore) per manufacturers instructions and buffer exchanged with dH$_2$O. One tenth of the recovered DNA was amplified with Advantage cDNA polymerase mix (Clontech) with 0.2 mM dNTP (PE/ABI) and 0.3 $\mu$M each of the internal nested oligonucleotides (Ico375 and Ico376) at 0.3 $\mu$M in 50 $\mu$l reactions. Two cycles PCR was used again with an initial heat denaturation step at 94° C. for 1'40" then 2 cycles of 96° C. for 16" and 68° C. for 2' then 13 cycles of 96° C. for 16" and 72° C. for 2' with a final extension of 6' at 74° C. Ten $\mu$l of the 50 $\mu$l reactions were run on a 1.2% agarose gel with 2 $\mu$l 6X loading dye. The resulting bands were of the expected size, 1.05 kb. The remainder of the PCR reactions were passed through Chromaspin-400 columns (Clontech) per manufacturers instructions to remove reaction components and to exchange buffer with TE (10 mM Tris-HCl pH8.0/1 mM EDTA). The DNA containing eluates were washed with dH$_2$O and concentrated with Microcon-100 spin-filters (Amicon/Millipore) as described by the manufacturer's instructions.

Cloning:

The purified PBGD DNA was digested for 6 hours with 40 Units each of EcoR I and Hind III in EcoR I "U" buffer (New England Biolaps (NEB)) in 50 $\mu$l reactions at 37° C. Enzymes were heat killed for 20 minutes at 68° C. and reactions were spun in Microcon 100 spin-filters to remove small DNA end pieces, washed with dH$_2$O and concentrated. One fifth of the resulting DNA was ligated with approximately 50 ng EcoR I and Hind III digested and twice gel purified pBluescriptII SK-(Statagene) and 200 units T4 DNA ligase (NEB cohesive end units) for 15 hours at 16° C. The ligase was heat killed at 75° C. for 10 minutes. The reactions were then buffer exchanged with dH$_2$O and concentrated in Microcon-100 spin filters and volumes taken up to 5 $\mu$l with dH$_2$O. One $\mu$l each was electroporated into 25 $\mu$l DH10B Electromax cells (Gibco/BRL) at 2.5 Kv/200 Ohms/25 $\mu$F in 0.1 cm cuvets with a BioRad electroporator. One ml of SOC medium (Gibco/BRL) was added and the cells were outgrown at 37° C. for one at 250 rpm. Cells were plated out on LB plates (Maniatis T., E. F. Fritsch, J. Sambrook. Molecular Cloning (A laboratory Manual) Cold Spring Harbor Laboratory. 1982) with 150 $\mu$g/ml ampicillin. The efficiency of all five were approximately twice background (vector ligated without insert). Colony PCR was used to analyze 18 transformants of each electroporation for the presence of PBGD. An internal PBGD specific primer (ICO381) was used with a pBluescript specific primer (ICO385) to both confirm identity and proper orientation in the vector. The 25 µl reactions were set up on ice to inactivate proteases with primer concentrations of 0.4 µM, 0.125 U Taq polymerase (Fisher), and 0.2 mM dNTP(PE/ABI). Two cycle PCR was used, with an initial heat denaturation step at 94° C. for 1'40" a further denaturing step at 96° C. for 20 seconds, then 30 cycles of 96° C. for 16" and 68° C. for 1' with a final extension of 4' at 74° C. Five µl of 6X loading dye was added and 12.5 µl each were run out on a 1.2% agarose gel. Results are as follows: 12/18 positive colonies for spleen; 10/18 for bone marrow; 8/18 for lymph node; 9/18 for brain and 10/18 for adipose tissue. Two positive colonies each for the first 3 and 1 each for the latter two were grown up in 25 ml. liquid LB culture with 150 µg/ml ampicillin over night at 37° C. with 250 rpm. Plasmid DNA was purified from the cultures with Qiagen's Tip-100 DNA purification kit per manufacturer's instructions. UV absorbance at 260 nm was used to determine the plasmid yields which varied from between 131 and 169 µg of highly purified DNA.

Sequencing:

Sequencing reactions of double stranded plasmid DNA with Big Dye terminator cycle sequencing were performed in a 9700 thermocycler (Perkin Elmer/Applied Biosystems) Two vector primers (ICO383 and ICO384) and two PBGD specific internal primers (ICO380 and ICO381) were used for all 8 plasmids. In addition a fifth vector primer (ICO385) was used for the brain and adipose derived clones. Reaction conditions were per manufacturers protocol as follows: 500 ng plasmid DNA and 4 pmol oligonucleotide primer with 8 µl ready mix in 20 µl volumes with 30 cycles of 96° C. for 12" and 60° C. for 4'. Extension products were purified by isopropanol precipitation. To each reaction 20 µl of dH$_2$O and 60 µl isopropanol were added. These were mixed by inversion and allowed to sit at room temperature for 15 minutes then spun for 40' at 3250 rpm in a Beckman GS-6-KR centrifuge with the GH3 rotor and Microplate+ carriers. Reactions were inverted then spun at 1680 rpm for 1' to remove liquid from the pelleted DNA. DNA sequence analysis was performed at the University of Washington Biochemistry Department sequencing Laboratory with an Applied Biosystems 377 sequencer.

Analysis:

The inserts of all 8 clones were confirmed to be PBGD by complete double strand sequence analysis (see sequences 1–8). Each has some change(s) from the published sequences. Some changes are unique and some are shared with other clones (see Table 2 and Table 3). For differences found only in one clone, it is difficult to distinguish between PCR or cloning artifacts and actual allelic variations without additional sampling. However, when the same base difference is found in more than one sequence it is unlikely to be from cloning errors. From the alignment of all 11 PBGD sequences a set of common bases emerged, the consensus or wild type allele sequence. Five of the eight clones (1.1, 1.3, 2.1, 3.3, and 5.3.) have the wild type amino acid sequence. Within this set with wild type amino acid sequence, there is only one difference at the nucleic acid level. At position 555, 4 of the 5 sequences have a dGTP while 1 along with the published erythropoietic and genomic PBGD have a dTTP. These appear to be two common alleles, which result in no amino acid difference. There are 2 base changes between clone number 1.1 and the published erythropoietic PBGD. An adenine to guanine change at base 513 (Leu 171) is a silent mutation, which is also present in 9 out of the 11 sequences, compared. The second difference is a cytosine to adenine substitution at base 995 (Thr 332.) This is not a silent change, with a threonine to asparagine non-conservative mutation. It appears however that the difference is an error in the published erythropoietic PBGD sequence since all 10 other sequences have an adenine at this position. In addition to these natural variations, there are three additional silent mutations introduced during the cloning at positions 1017, 1018 and 1020 to create a Mun I site for future manipulations. The PBGD gene was ligated into pBluescript SK plasmid generating the pSK-PBGD 3988 bp plasmid, which was sequenced.

Conclusion:

For any recombinant therapeutic protein it is important that the wild type allele be used to reduce the potential for immunogenicity. We feel confident through over survey of the literature and analysis of PBGD sequence from different individuals that clone number 1.1 represents the most prevalent "wild type" allele in the population with respect to amino acid sequence. Clone number 1.1 contains the consensus wild type amino acid sequence and differs from the published erythropoietic PBGD sequence by only one amino acid. Because this differences is found in all the other PBGD clones besides the erythropoietic PBGD sequence, it, rather than the published erythropoietic sequence, is deemed to be the prevalent wild type sequence. For this reason PBGD encoded by clone number 1.1 was chosen for production of recombinant human porphobilinogen deaminase (rhPBGD). In the following, the plasmid encoding the human wild type PBGD in clone number 1.1 will be termed "pPBGD1.1".

Equipment and supplies lists are shown in appendix 1 and 2, respectively.

TABLE 1

Oligonucleotide primers used for PCR amplification and sequencing of PBGD

| | | |
|---|---|---|
| Ico375-pbgds | (32 mer) | coding region 5' end w/EcoRI site sense |
| 5' CGT GGA ATT CAT GAG AGT GAT TCG CGT GGG TA 3' | | (SEQ ID NO: 14) |
| Ico376-pbgds | (47 mer) | coding region 3' end w/HindIII site antisense |
| 5' GGA GAA GCT TAT TAA TGG GCA TCG TTC AAT TGC CGT GCA ACA TCC AG 3' | | (SEQ ID NO: 15) |
| Ico379-esnonc | (20 mer) | erythropoietic form non-coding sense |
| 5' TCG CCT CCC TCT AGT CTC TG 3' | | (SEQ ID NO: 16) |
| Ico380-sinter | (21 mer) | internal coding sense |
| 5' CAG CAG GAG TTC AGT GCC ATC 3' | | (SEQ ID NO: 17) |
| Ico381-ainter | (21 mer) | internal coding antisense |
| 5' GAT GGC ACT GAA CTC CTG CTG 3' | | (SEQ ID NO: 18) |
| Ico382-anonc | (20 mer) | non-coding antisense |
| 5' CAG CAA CCC AGG CAT CTG TG 3' | | (SEQ ID NO: 19) |
| Ico383-pSKT7 | (22 mer) | pBluescript T7 promoter |
| 5' GTA ATA CGA CTC ACT ATA GGG C 3' | | (SEQ ID NO: 20) |
| Ico384-pSKpjrev | (22 mer) | pBluescript reverse2 |
| 5' CTA AAG GGA ACA AAA GCT GGA G 3' | | (SEQ ID NO: 21) |

TABLE 1-continued

Oligonucleotide primers used for PCR amplification and sequencing of PBGD

| Ico385-pSKrev | (21 mer) | pBluescript reverse2 | |
|---|---|---|---|
| 5' CAG CTA TGA CCA TGA TTA CGC 3' | | | (SEQ ID NO: 22) |

TABLE 2

Variation of PBGD clones from published erythroid sequence:

| PBGD clone | Differences from Erythroid mRNA | | | Genebank No. | Reference/Source |
|---|---|---|---|---|---|
| | silent | non-silent | total diffs | | |
| Erythroid | 0 | 0 | 0 | X04217 | Raich, N. et. al. 1986, Nucleic Acids Res. 14 (15), 5955–5968 |
| Constitutive | 1 | 2 | 3 | X04808 | Grandchamp, B. et. al. 1987, Eur. J. Biochem. 162 (1), 105–110 |
| Genomic | 1 | 2 | 3 | M95623 | Yoo, H. W. et. al. 1993, Genomics 15 (1), 21–29 |
| 1.1 | 1 | 1 | 2 | — | Spleen (Clontech mRNA Lot No. 7120266) |
| 1.3 | 2 | 1 | 3 | — | Spleen (Clontech mRNA) |
| 2.1 | 2 | 1 | 3 | — | Bone Marrow (Clontech mRNA) |
| 2.2 | 2 | 2 | 4 | — | Bone Marrow (Clontech mRNA) |
| 3.1 | 2 | 4 | 6 | — | Lymph Node (Clontech mRNA) |
| 3.3 | 3 | 1 | 4 | — | Lymph Node (Clontech mRNA) |
| 5.3 | 2 | 1 | 3 | — | Total Brain (Clontech mRNA) |
| 6.1 | 3 | 2 | 5 | — | Adipose Tissue (Clontech mRNA) |

Table 2:

Summary of the number of differences in amino acid sequence of our sequenced PBGD clones and clones from Genebank entries for the constitutive and genomic PBGD with published Erythropoietic PBGD sequence. Shown in different columns are the total number of silent mutations with a DNA base change not causing a corresponding amino acid change, the number of non-silent mutations with a DNA change causing an amino acid difference and the sum of the two types of mutations. Not included in this table are the three silent mutations introduced into the clones to create an internal Mun I endonuclease cleavage site. Note that clone number 1.1 which will be used for production of recombinant human porphobilinogen deaminase (rhPBGD) has only one of each type of difference with the least number of total differences.

TABLE 3

Summary of mutations found in PBGD clones:

| aa | aa No. | bp No. | mutation | aa change | cons. | gen. | 1.1 | 1.3 | 2.1 | 2.2 | 3.1 | 3.3 | 5.3 | 6.1 | No./10 |
|---|---|---|---|---|---|---|---|---|---|---|---|---|---|---|---|
| Asp | 19 | 56 | A→G | Asp→Gly | | | | | | | X | | | | 1 |
| Phe | 108 | 322 | T deletion | frame shift | | | | X | | | | | | | 1 |
| Lys | 140 | 419 | A→G | Lys→Arg | | | | | | | X | | | | 1 |
| Leu | 160 | 478 | C→A | Leu→Met | X | | | | | | | | | | 1 |
| Ala | 168 | 503 | C→T | Ala→Val | | | | | | | X | | | | 1 |
| Leu | 171 | 513 | A→G | silent | | X | X | X | X | X | X | X | X | X | 9 |
| Val | 185 | 555 | T→G | silent | X | | | X | X | X | | X | X | X | 7 |
| Glu | 193 | 577 | G→A | Glu→Lys | X | | | | | | | | | | 1 |
| Gly | 243 | 729 | C→T | silent | | | | | | | X | | | | 1 |
| Ala | 280 | 840 | T→C | silent | | | | | | | | | X | | 1 |
| Ala | 286 | 856 | G→A | Ala→Thr | | | | | | | | | X | | 1 |
| Lys | 328 | 984 | A→G | silent | | | | | | | X | | | | 1 |
| Thr | 332 | 995 | C→A | Thr→Asn | X | X | X | X | X | X | X | X | X | X | 10 |
| Gln | 339 | 1017 | G→A | silent | | | X | X | X | X | X | X | X | | 8 |
| Gln | 339 | 1018 | C→T | silent | | | X | X | X | X | X | X | X | | 8 |
| Leu | 340 | 1020 | T→G | silent | | | X | X | X | X | X | | X | | 7 |
| Leu | 340 | 1020 | T deletion | frame shift | | | | | | | | | X | | 1 |

Table 3: Summary of the genetic differences of our sequenced PBGD clones and Genbank entries for the constitutive and genomic PBGD with published erythropoletic PBGD sequence from the allele sequence alignment. Listed in different columns are the amino acid, base number from the ATG start codon, the actual genetic difference with corresponding amino acid change if any and a listing of the clones with differences shown with an X. In the final column the total number of clones with the different mutations are shown.
The three mutations at position 1017, 1018 and 1020 are introduced with ICO376 during PCR amplification to create a Mun 1 endonuclease cleavage site.
Note that clone number 1.1 which will be used for production of rhPBGD only has genetic differences which also are represented by a number of other clones.

Expression Plasmids
Construction of the Basic Expression Plasmid pExp0

The basic expression plasmid pExp0 was constructed by excising the PBGD coding sequence (cDNA) from plasmid pPBGD1.1 (see FIG. 1) with EcoR I and Hind III and inserting it into the vector pKK223-3 (Pharmacia, Catalogue #27-4935) cut with the same enzymes, thus operatively linking it to the IPTG-inducible tac promoter (Amann E. et al. 1983, Gene 25(2–3):167–178). FIG. 1 shows the construction details. Plasmid pExp0 was constructed for a preliminary assessment of the expression levels and does not directly lead to the construction of the final expression plasmid.

Construction of the Final Expression Plasmid

The final expression plasmid pExp1-M2-BB (FIG. 9) was constructed in a multi-step process. The individual steps used and all the intermediate plasmids are outlined below.

Construction of Plasmid pExp1

Plasmid pExp1 was first constructed with modifications to the 5' untranslated region and the initial part of the coding sequence both aimed at improving translation efficiencies (Gold L. and Stormo G. D. 1990, Methods Enzymol 185:89–93). The changes are indicated below, and include, insertion of a second ribosome binding site, an AT-rich sequence preceding the ATG and three silent base substitutions shown in boldface.

AATTCTAACA TAAGTTAAGG AGGAAAAAAA A ATG AGA
GTT ATT CGT GTC GGT AC (SEQ ID NO:23)

Met-Arg-Val-Ile-Arg-Val-Gly (SEQ ID NO:24)

A naturally occurring Kpn I site six amino acid residues into the coding sequence of the human cDNA for PBGD (pPBGD1.1) was exploited for this purpose. Oligonucleotides ICO386 and ICO387 were designed to provide upon annealing to each other a 5' EcoR I adhesive end and a 3' Kpn I sticky end and the elements described above including the codons for the first six amino acid residues as shown. Oligonucleotides ICO386 and ICO387 were annealed and ligated with the Kpn I-Hind III, PBGD fragment from pPBGD1.1 into EcoR I-Hind III linearised pBluescript II SK-(Stratagene, Catalogue #212206) to yield plasmid pPBGD1.1Tra. In the second step, the EcoR I-Hind III fragment from pPBGD1.1Tra was ligated into pKK223-3 cut with the same enzmes resulting in plasmid pExp1 (FIGS. 4 and 5).

Construction of Plasmid pExp1-M2

The tetracycline resistance gene was next restored using the following strategy. Plasmid pExp1 was cut with Sal I and BamH I and the 5349 base-pair fragment containing part of the tetracycline coding sequence and the bulk of the plasmid was isolated. Into this was ligated the Sal I-Hind III fragment from pBR322 (New England BioLabs, Catalogue #303-3S) containing rest of the coding sequence and an adapter formed by annealing oligonucleotides ICO424 and ICO425 to each other. The adapter contains part of the tetracycline promoter and provides Hind III and BamH I overhands for ligation but destroys the Hind III and BamH I restriction sites. The resulting plasmid was called pExp1-M2 (FIGS. 6 and 7).

Construction of Plasmid pExp1-M2-BB

Figure 9:
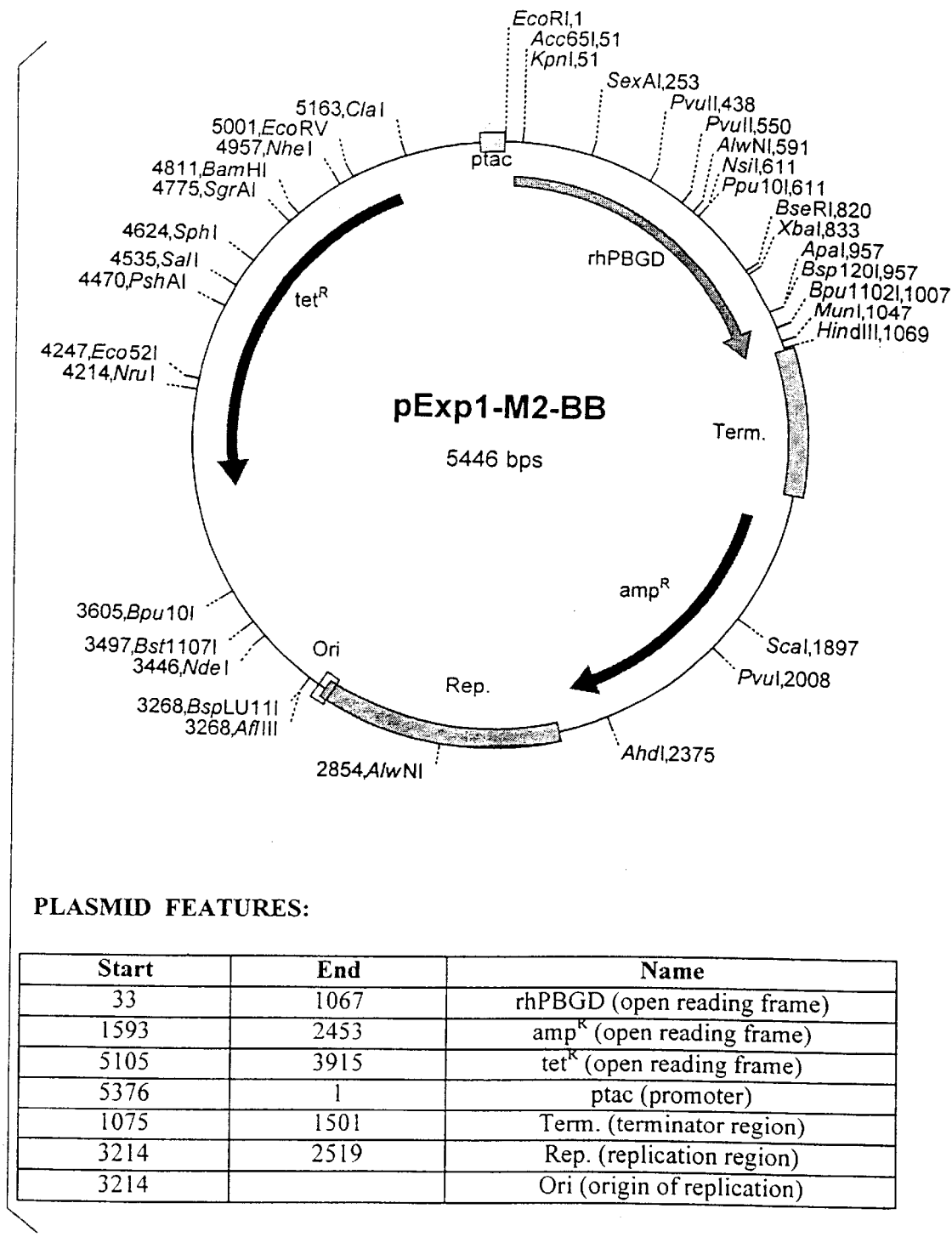
Figure 10:
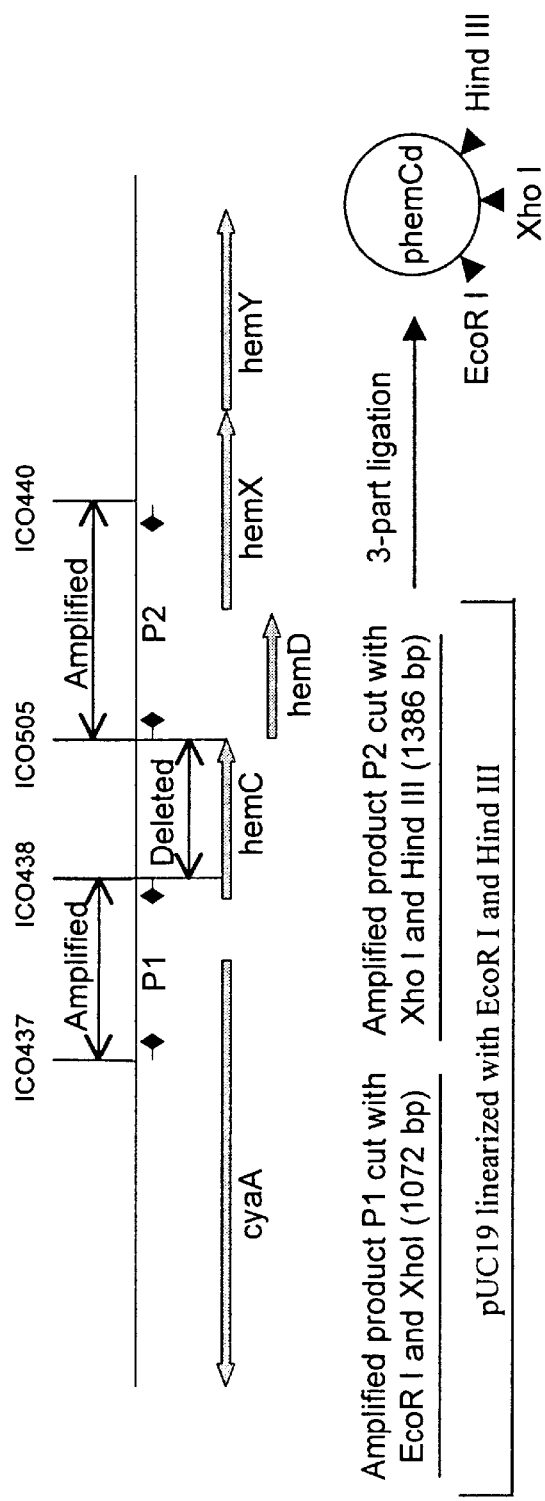

In the final step the rop gene contained between BsaA I and BsaBI was deleted to increase copy number (Makrides S. C. 1996, Microbiol.Rev. 60(3):512–538). For this the plasmid pExp1-M2 was cycled through the dam minus strain, JM110 (F' [traD36 proA$^+$ proB$^+$ lacI$^q$ Δ (lacZ)M15] dam dcm supE44 hsdR17 thi leu thr rpsL lacY galK galT ara tonA tsx Δ (lac-proAB) lambda$^-$) as restriction with BsaB I is blocked by overlapping dam methylation. It was then cut with BsaA I and BsaB I to excise the rop gene and the 5446 base-pairs long linear fragment was circularised by blunt-end ligation to yield the production plasmid pExp1-M2-BB (FIGS. 8 and 9).

Construction of the hemC-Deletion Host and the Final Expression Strain

The parent strain JM105 (F' [traD36 proA+ proB+ lacI$^q$ Δ(lacZ)M15]Δ(pro-lac) hsdR4 sbcB15 rpsL thi endA1 lambda$^-$), a derivative of E. coli K12 was obtained from Parmacia, Catalogue #27-1550-01. The hemC gene coding for the endogenous E. coli Porphobilinogen Deaminase was partially deleted. This was necessary to ensure that the purified product (rhPBGD) was free from contaminating E. coli PBGD as the E. coli and human enzymes are very similar in properties (Jordan P. M. 1994, Wiley, Chichester (Ciba Found Symp 180), p70–96) and may co-purify. The hemC-deletion host was derived from JM105 according to Scheme A. First a hemin-permeable variant was obtained by a three-step process. This was essential as a hemC-deletion mutant would require hemin for good growth and E. coli K12 strains are not freely permeable to hemin.

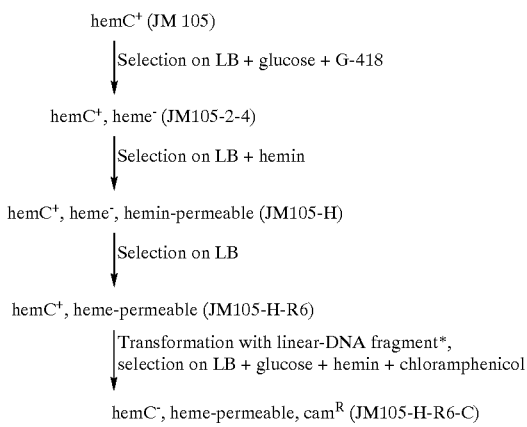

Scheme A. Scheme for obtaining hemC-deletion strain

All mutant isolation was spontaneous. Approximately 5×10$^{-8}$–5×10$^{-9}$ cells were plated on selective media. The media compositions are included as Appendix 1.

Figure 11:
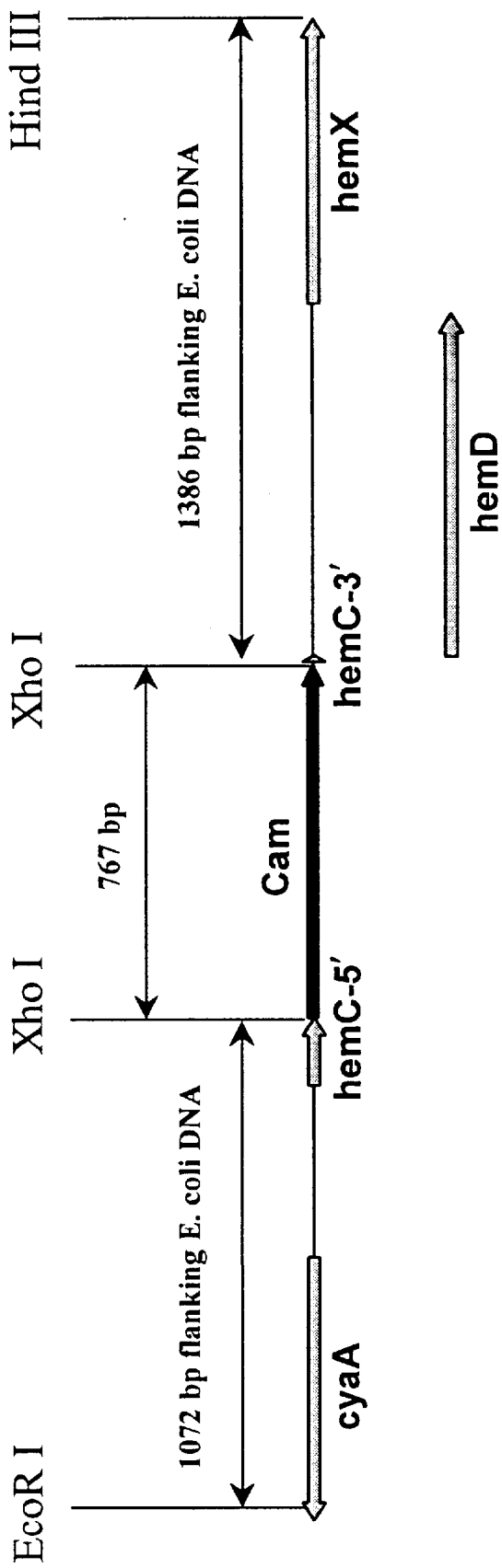

For details on the linear DNA-fragment see FIG. 11.

In the first step, a heme-minus mutant was isolated carrying a defect in any of the biosynthetic steps leading to the formation of heme. Heme strains fall into the general class of respiration deficient mutants that are defective in active transport and consequently resistant to low levels of antibiotics of the aminoglycoside family such as gentamicin (Lewis L. A. et al. 1991, Microbiol.Immunol. 35(4):289–301). Several spontaneous mutants were isolated as a dwarf colonies on LB+glucose +G-418 (gentamicin)-containing plates (Lewis L. A. et al. 1991, Microbiol.Immunol. 35(4):289–301). These were screened for their ability to respond weakly to hemin, indicating that they were heme$^-$ (as opposed to other respiration deficient mutants which would not respond to hemin at all). One such heme-strain (JM105-2-4, see Scheme A) which could also revert back spontaneously to robust growth on LB (as this is essential for the third step, see below) was selected. This strain was next plated on LB+hemin to obtain a better grower in the presence of hemin and was called JM105-H. It showed improved growth only in the presence of hemin, which meant that is still was heme$^-$ but had become hemin-permeable. To restore the functionality of the heme biosynthetic pathway in JM105-H, spontaneous revertants were isolated on LB plates and only those retained which resembled the starting strain JM105 in growth, both untransformed and after transformation with the expression plasmid. One such strain used in this study was called JM105-H-R6 and should have retained the heme-permeable trait of its parent strain.

Strain JM105-H-R6 was transformed with the EcoRI-Hind III fragment (see Scheme A), to obtain the hemC-deletion host called JM105-H-R6-C by homologous gene replacement. This strain has the genotype, F′[traD36 proA+ proB+ lacI$^q$ Δ(lacZ)M15] Δ(pro-lac) hsdR4 sbcB15 rpsL thi endA1 lambda$^-$ hemC:CAT hemin-permeable. It was transformed with the expression plasmid pExp1-M2-BB to yield the final production strain PBGD-2 (PBGD-2 was deposited under the Budapest Treaty on Jul. 9, 1999 with DSMZ (Deutsche Sammlung von Mikroorganismen und Zellkulturen, GmbH, Mascheroder Weg 1b, D-38124 Braunschweig, Germany) under the accession No. DSM 12915).

In order to obtain the EcoRI-Hind III fragment, a multiple PCR strategy was used. Oligunocleotide pairs ICO437, ICO438 and ICO505, ICO440 were used to amplify separately, portions of E. coli JM105 genomic DNA segments flanking the hemC gene (see FIG. 10). These amplified gene products were digested with pairs of enzymes EcoR I, Xho I and Xho I, Hind III respectively, and in essence, assembled together between the EcoR I and Hind III sites of pUC19 to give plasmid phemCd. Next the fragment containing the chloramphenicol-resistance gene was PCR amplified from plasmid pBC SK+ (Stratagene, Catalogue #212215) using oligonucleotides ICO510 and ICO511. This product was cut with Xho I and inserted into plasmid phemCd at the Xho I site. In essence, the plasmid having the Cam gene in the orientation shown was called phemCdCm and formed the source of the EcoR I-Hind III linear DNA-fragment depicted in FIG. 11.

In FIG. 11 the structure of the linear DNA-fragment used for the transformation is shown. The genetic organization of the E. coli polypeptides depicted by gray arrows (cyaA, hemC-5′, hemC-3′, hemX and hemD) is derived from the GenBank report Accession number AE000456. The black arrow represents the 767 base-pairs long PCR fragment carrying the cholamphenicol-resistance gene (Cam), encoding chloamphenicol acetyltransferase (CAT), replacing 806 base-pairs of the hemC coding sequence. HemC-5′ and hemC-3′ correspond to 149 and 16 base-pairs respectively, of the coding sequence of the disrupted hemC gene. EcoR I, Xho I and Hind III are engineered restriction sites. The sequence of this 3225 base-pairs long fragment is shown in Seq. ID NO 2. The two Xho I sites are at positions 1072 and 1839 in the sequence, respectively.

TABLE 4

Oligonucleotide primers used in the construction of the production strain PBGD-2

```
ICO386       (54 mer)   Construction of plasmid pExp1
5' AAT TCT AAC ATA AGT TAA GGA GGA AAA AAA AAT GAG AGT TAT TCG TGT CGG
TAC 3' (SEQ ID NO:25)

ICO387       (46 mer)   Construction of plasmid pExp1
5' CGA CAC GAA TAA CTC TCA TTT TTT TTT CCT CCT TAA CTT ATG TTA G 3' (SEQ ID NO:26)

ICO424       (32 mer)   Construction of plasmid pExp1-M2
5' GAT CAC TCA TGT TTG ACA GCT TAT CAT CGA TT 3' (SEQ ID NO:27)
A
ICO425       (31 mer)   Construction of plasmid pExp1-M2
5' AGC TAA TCG ATG ATA AGC GTC AAA CAT GAG T 3' (SEQ ID NO:28)

ICO437       (32 mer)   Amplification of product P1
5' AGT CAG AAT TCA GAC GCA CGG CGG TAC GAT AA 3' (SEQ ID NO:29)

ICO438       (32 mer)   Amplification of product P1
5' ATT CAC TCG AGG TCA CCA TCG GTA CCA GTT CA 3' (SEQ ID NO:30)

ICO440       (32 mer)   Amplification of product P2
5' AGA TCA AGC TTC GGC CAG ACG CAG GTT ATC TA 3' (SEQ ID NO:31)

ICO505       (34 mer)   Amplification of product P2
5' ATA CAC TCG AGA CCG GCA TGA GTA TCC TTG TCA C 3' (SEQ ID NO:32)

ICO510       (39 mer)   Amplification of Cam gene
5' ACT GAC CTC GAG CGG CAC GTA AGA GGT TCC 3' (SEQ ID NO:33)

ICO511       (29 mer)   Amplification of Cam gene
5' ACT GAA CTC GAG AAT TAC GCC CCG CCC TG 3' (SEQ ID NO:34)
```

Accordingly, the cDNA used for expressing rhPBGD was derived from plasmid pPBGD1.1. The starting host strain was derived from JM105 and is called JM105-H-R6-C. The genotype and the details on its construction are described above. A large part of the coding region of the hemC gene was replaced by the Cam gene, encoding chloramphenicol acetyltransferase. This gene replacement was confirmed by PCR amplification of the segment of the E. coli genome followed by restriction analysis of the amplified product. As a result of the gene replacement, the strain is resistant to chloramphenicol and grows extremely poorly on LB medium. Growth improves when LB medium is supplemented with hemin.

Expression Construct

The expression plasmid in the final production strain is pExp1-M2-BB. Its construction is described above. A detailed map of the plasmid showing the one reading frames and functionally relevant regions is shown in FIG. 9. The complete DNA sequence is included in Seq. ID NO 1. All synthetic adapters and linkers used during the construction have been sequenced along with all junctions created during ligation which directly impinge upon the expression of the cloned gene.

Production Strain

The final production strain is called PBGD-2. It was obtained by introducing the expression plasmid pExp1-M2-BB into the host strain JM105-H-R6-C, essentially, by rendering the cells competent with 100 mM $CaCl_2$ (Morrison D. A. 1979, Methods.Enzymol. 68:326–331) and selecting for transformants on LB+ampicillin media at 30° C. The plasmid is a derivative of pBR322 without the rop gene and should be present extrachromosomally in moderate copy number at 30° C. with a slightly higher copy number at elevated temperatures 37° C. and greater (Makrides S. C. 1996, Microbiol.Rev. 60(3):512–538). It has both the ampicillin and tetracycline resistance genes as selectable markers. It also expresses rhPBGD which can complement the hemC defect of the host strain. As a result, the production strain should grow normally on LB/M9 media, be resistant to the antibiotics ampicillin and tetracycline and also be resistant to the antibiotic chloramphenicol (because of the presence of the Cam gene in the genome). It was confirmed to have all these characteristics.

Expression

The expression of rhPBGD is driven by the tac promoter which is regulated by the copy of the $lacI^q$ gene present in the host. Due to the modifications made to the system as described in the study plant, the uninduced level of expression is 1.8 units/mg (see Appendix 3 for assay details), which amounts to approximately 10% of the total soluble protein. The culture is grown throughout at 30° C. and no induction step is used to increase expression.

Evaluation and Conclusions

The expression system developed for the production of rhPBGD in *E. coli* is a stable system, producing good amounts of rhPBGD in a constitutive manner when the cells are grown at 30° C. The host strain employed is partially deleted for the gene producing the endogenous *E. coli* porhobillinogen deaminase. After transformation with the expression plasmid, the resulting production strain PBGD-2 grows as well as the strain PBGD-1 (which is JM105 carrying the same expression plasmid) and makes the same amount of rhPBGD.

Alternative Expression Construct

Expression Plasmid pExp1-M2-Puc-BB and Expression of rhPBGD in *E. coli*

The plasmid pExp1-M2 was digested with Pvu I and Afl III and the larger of the two fragments corresponding to a size of 4745 base-pairs was isolated. This was ligated to the 1257 base-pairs long Pvu I-AflII fragment derived from pUC19 containing the origin of replication and part of the ampicillin resistance gene to obtain plasmid pExp1-M2-Puc. This was passaged through JM110 and cut with BsaA1 and BsaB1 to excise the rom gene contained between the two sites and blunt-ended together to yield the final expression plasmid pExp1-M2-Puc-BB. The pExp1-M2-Puc-BB plasmid has been fully sequenced and differs from pExp1-M2-BB only in that C in position 2769 is T in pExp1-M2-Puc-BB.

Expression of rhPBGD in *E. coli*

The *E. coli* K12 host strain JM105 genotype endA thi rpsL sbcB15 hsdR4 Δ(lac-proAB) [F'traD36 proAB $lacI^q$ Δ(lacZ) M15] containing the expression plasmid pExp1-M2-Puc-BB was grown in LB broth containing 100 μg/ml ampicillin at to mid-log phase at 30° C. from a 1 to 40 dilution of an overnight inoculum. The culture was then split into three and growth was continued for another 4 hours at 30° C., 37° C. and 42° C. respectively. Cells were spun down from 1 ml samples and frozen at −20° C. The thawed cell pellets were resuspended in 200–300 μl of B-PER reagent PIERCE Cat. #78243, incubated at room temperature for 10 minutes, spun at 16,000 for 10 minutes and PBGD activity was determined in the supernatants. Total protein was estimated by the Bradford method using the BioRad reagent Cat #500-0006 and bovine serum albumin as standard. The specific activities in the crude lysates obtained at the three growth temperatures are tabulated below. The results clearly show an increase of PBGD units/mg with increasing temperature in the range from 30° C. to 40° C.

| Temperature | PBGD Units/mg |
| --- | --- |
| 30° C. | 363 |
| 37° C. | 573 |
| 42° C. | 1080 |

Other Production Systems For rhPBGD

For yeast production, the PBGD coding sequence can be inserted into a plasmid vector, for example YEP type, containing 2 μ circular DNA (Ori) origin for high expression in yeast. YEP plasmids contain TRP 1 and URA 3 as markers for selective maintenance in trp1−, ura 3-yeast strains.

Alternatively, the PBGD gene can be inserted in bovine papilloma virus vectors BPV for high expression in a murine cell line C-127 (Stephens P. E. et al. Biochem J. 248, 1–11, 1987) or vectors compatible with expression in CHO cells or COS cells.

An expression of PBGD can be made intracellularly.

A secretory signal in Saccharomyces, for example alpha-mating factor presequence, can be added in front of the rhPBGD structural gene for efficient secretion in yeast.

Similarly, a sequence encoding a mammalian signal peptide can be added for secretion of rhPBGD into the culture medium upon expression in for example CHO cells or COS cells.

A bacterial promoter for example the tryptophane (trp) promoter or the lac promoter or alternatively an alkaline phosphatase promoter, should be inserted before the PBGD coding region for efficient transcription in prokaryotes for example *E. coli*.

A yeast promoter for example 3-phosphoglycerate kinase (PGK) or chelatin or alpha-mating factor should be inserted before the PBGFD coding region for efficient transcription in yeast for example *Saccharomyces cerevesiae* or *Saccharomyces pombe*.

A mammalian promoter for example Metallothionin-1 (MT-1) or

Aspartate transcarbamylaseor *Dihydrofolate reductase* (DHFR) should be inserted before the PBGD coding region for efficient transcription in mammalian cell lines for example CHO cells or COS cells.

The yeast plasmid (Y-G&F-PBGD) containing a yeast promoter, signal and/or ATG codon (methionine) in front of PBGD coding region and a yeast vector containing selectable markers such URA 3 or TRP 1 will be transformed into the yeast host cell such as *Saccharomyces cerevesiae* or *Saccharomyces pombe* for production of rhPBGD.

The mammalian plasmid (M-G&F-PBGD) containing a mammalian promoter for example Metallothionine-1 or *Dihydrofolate reductase* and a mammalian signal sequence or an ATG codon in front of the PBGD coding region and vector pAT or pSV2 respectively. Plasmid (M-G&F PBGD) may be transfected into a mammalian cell line for example CHO cells, for production of rhPBGD.

The *E. coli* cell containing plasmid (pExp1 or pExp1-M2 Puc-BB), may be fermented to stationary phase between 24–48 hours, in a medium containing casein hydrolysate, or yeast extract, glucose, vitamins and salts. pH oxygen may be monitored by electrodes during fermentation. Temperature will be kept at 37 +/−2 C during the fermentation.

The yeast cell containing the plasmid (Y-G&F-PBGD), may be fermented to late log phase between 20–40 hours in a medium containing yeast extract, glucose, salts and vitamins. pH and temperature will be monitored by specific electrodes during fermentation. Temperature will be kept at 30+/−2 C during fermentation.

The mammalian cell line containing the plasmid (M-G&F-PBGD) may be fermented in a medium containing, foetal calf serum (or serum free), vitamins, glucose, antibiotics, growth factors. pH and temperature will be monitored continuously during fermentation by specific electrodes.

Fermentation and Purification rhPBGD may be recovered from *E. coli* after fermentation by an extraction procedure involving for example ribipress, sonication, osmotic shock or total solubilization by detergent for example Tween 80, Triton X-100 or Brij. rhPBGD will be recovered from fermentation medium after production in yeast or from a total cellular extract using detergents such as Triton X-100, Tween 80 or Brij. rhPBGD will be recovered from mammalian culture medium or from a total cellular extract by ion-exchange chromatography or affinity chromatography.

rhPBGD may be purified from *E. coli* extract or from yeast medium or total cellular extract or from mammalian culture medium or total mammalian cellular extract by binding to an ion-exchange column for example DEAE-Sepharose or MonoQ-Sepharose and eluted with for example NaCl and Sodium phosphate buffer pH 7–8 or the corresponding potassium salts.

Alternatively, rhPBGD may be recovered from extracts by binding to an affinity chromatography column for example an anti-PBGD affinity column. rhPBGD will be eluted by lowering the pH to 4-2, or a thiol specific affinity column, rhPBGD has been "tagged" with thiols residues when a thiol affinity column step is used. Thiols will be removed by a specific enzymatic cleavage sep to generate authentic rhPBGD.

The ion-exchange or affinity purified rhPBGD will be further purified by hydrophobic interaction chromatography on for example, TSK Phenyl 5 PW column or Octyl-Sepharose or Phenyl-Sepharose columns.

Binding of rhPBGD may be done at high ionic strength for example in 10–50 mM Tris-HCl pH 7–8, 1M NaCl or 10–15 mM Sodium phosphate pH 7–8, 0.5 M MgSO$_4$ and eluted by lowering the ionic strength for example with 10–50 mM Tris-HCl pH 7–8 or 10–50 mM Sodium phosphate pH 7–8.

Three hydrophobic interaction steps will be applied consecutively.

rhPBGD is further purified with preparative RP-HPLC for example C12 or C18 matrixes. The rhPBGD is be eluted from the column by a gradient of 10–50 mM Sodium phosphate and 1–10% acetonitrile buffer.

Formulation of rhPBGD is done by passing the enzyme over a G-100 Sephadex column and eluting it in an isotonic solution for example 0.9% NaCl and 10–50 mM Sodium phosphate pH7.0 +/−0.5 or Sodium phosphate, glycin, mannitol or the corresponding potassium salts.

For the preparation of a medicament, the formulation solution of rhPBGD may be sterile filtered and filled aseptically in glass vials and lyophilised.

Alternatively, the sterile filtered rhPBGD solution is formulated in for example, lipid vesicles constituting phosphatidylcholine or phosphatidylethanolamine or combinations of these or incorporated into erythrocyte ghosts.

Reconstitution of lyophilised rhPBGD may be done in water for injection.

Alternatively, rhPBGD is formulated in a sustained release formulation involving a biodegradable microspheres, for example in polylactic acid, polyglycolic acid or mixtures of these.

Alternatively, rhPBGD is lyophilized in a two-compartment cartridge, where rhPBGD will be in the front compartment and water for reconstitution in the rear compartment. This two compartment cartridge may be combined with an injection device to administer either rhPBGD by a needle or needle less (by high pressure) device.

Alternatively, rhPBGD may be formulated in a physiological buffer containing an enhancer for nasal administration.

Alternatively, rhPBGD is formulated in an oral formulation containing for example, lipid vesicles (phospatidylcholine, phosphatidylethanolamine, sphingomyeline) or dextrane microspheres.

Although recombinant production of PBGD is preferred for the treatment of AIP, it can alternatively be produced from human red blood cells.

A general production and manufacturing of recombinant PBGD may be done by the following steps.

Recombinant PBGD production process; an outline

A: Fermentation
1. Master cell bank
2. Working cell bank
3. Production of seed culture
4. Fermentation in large fermenter (250 L >)

B. Purification
1. Cell concentration by filtration/centrifugation
2. Cell disruption
3. Ultrafiltration
4. Chromatography ion exchange DEAE-Sepharose, MonoQ-Sepharose
5. Hydrophobic interaction chromatography (Octyl/phenyl-Sepharose, TSK Phenyl, 5PW, Phenyl-Sepharose
6. Chromatography ion exchange (MonoQ)
7. Formulation by Gel filtration Sephadex G-100

C. Manufacturing
1. Sterile filtration
2. Aseptic filling
3. Lyophilization

Treatment of Other Porphyrias

In analogy with the new treatment of AIP patients with (recombinant) PBGD, hepatic Porphyrias such as ALA deficiency Porphyria (ADP), *Porphyria cutamea tarda* (PCT), Hereditary Coproporphyria (HCP) and Variegata Porphyria (VP) can benefit from substitution therapy by rALA dehydratase, rUroporphyrinogen decarboxylase, rCoproporphyrinogen oxidase and rProtoporphyrinogen oxidase, respectively.

Patients having Erythropoetic Porphyrias such as Congenital erythropoietic Porphyria (CEP) or Erythropoietic protoporphyria (EPP) will benefit from substitution therapy with rUroporphyrinogen III syntetase and rFerrochelatase, respectively.

Hepatoerythropoietic Porphyrias e.g. Hepatoerythropoietic Porphyrias (HEP) can be treated with rUroporphyrinogen decarboxylase.

All porphyrias can be treated by the administration of the enzymatic activity lacing or being reduced (normally 50%) in any of the eight steps in the heme biosynthetic pathway as described above.

The substitution of the enzymatic activity can be achieved by adding the corresponding recombinant enzyme or other molecules that will provide the missing enzymatic activity.

Gene Therapy as an Alternative Treatment for Patients with Acute Intermittent Porphyria (AIP)

The human enzyme Porphobilinogen deaminase PBGD is coded for by a single gene located on chromosome 11 q 24.

Mutations in this gene causes the disease Acute Intermittent Porphyria (AIP). The disease has been shown to be inhereted in an autosomal dominat way.

Today over 100 mutations in the PBGD gene has been identified (Grandchamp B. J. Ganstroenterology and Hepathology, 11, 1046–1052, 1996. Table A) and the number is expected to increase when modern diagnostic systems based on screening programs will be applied more routinely in hospitals. A number of these mutations are shown in Table A.

TABLE A

Reported mutations in the PBGD gene

|  | Position | Mutation | Consequences | Reference |
|---|---|---|---|---|
| Exon 1 | 3 | ATG→ATA | Translation impairment | 18 |
|  | 33 | GCG→GCT | DS | 17 |
| Intron 1 | 33 + 1 | gtg→atg | DS | 16 |
| Exon 3 | 76 | CGC→TGC | R26C | 25 |
|  | 77 | CGC→CAC | R26H | 26 |
| Exon 4 | 91 | GCT→CACT | A31T | 24 |
|  | 97 | Del A | Frameshift | 25 |
|  | 100 | CAG→AAG | Q34K | 27 |
|  | 100 | CAG→TAG | Q34X | 25 |
|  | 125 | TTG→TAG | L42X | 19 |
| Exon 5 | 163 | GCT→TCT | A55S | 24 |
|  | 174 | Del C | Frameshift | 24 |
|  | 182 | Ins G | Frameshift | 24 |
| Intron 5 | 210 + 1 | gta→ata | DS (Del exon 5) | 24 |
| Exon 6 | 218–219 | Del AG | Frameshift | 24 |
| Exon 7 | 277 | GTT→TTT | V93F | 24 |
|  | 293 | AAG→AGG | K98R | 25 |
|  | 331 | GGA→AGA | G111R | 26 |
| Intron 7 | 345 − 1 | cag→caa | AS (Del exon 8) | 29 |
| Exon 8 | 346 | CGG→TGG | R116W | 20 |
|  | 347 | CGG→CAG | R116Q | 30 |
| Exon 9 | 445 | CGA→TGA | R149X | 25 |
|  | 446 | CGA→CAA | R149Q | 31 |
|  | 446 | CGA→CTA | R149L | 24 |
|  | 453 | CAG→TAG | Q155X | 32 |
|  | 470 | Ins A | Frameshift | 29 |
| Intron 9 | 499 − 1 | cag→caa | AS (Del exon 10) | 21 |
| Exon 10 | 499 | CGG→TGG | R167W | 33 |
|  | 500 | CGG→CAG | R167Q | 27,34 |
|  | 518 | CGG→CAG | R173Q | 34 |
|  | 530 | CTG→CGG | L177R | 27 |
|  | 593 | TGG→TAG | W198X | 19 |
|  | 604 | Del G | Frameshift | 35 |
|  | 610 | CAG→TAG | Q204X | 30 |
|  | 612 | CAG→CAT | DS (Del 9 bp exon 10) | 31 |
| Exon 11 | 625 | GAG→AAG | E209K | 28 |
| Intron 11 | 652 − 3 | cag→gag | AS (Del exon 12) | 33 |
| Exon 12 | 667 | GAA→AAA | E223K | 24 |
|  | 673 | CGA→GGA | R225G | 25 |
|  | 673 | CGA→TGA | R225X | 25 |
|  | 713 | CTG→CGG | L238R | 25 |
|  | 715–716 | Del CA | Frameshift | 19 |
|  | 730–731 | Del CT | Frameshift | 36 |
|  | 734 | CTT→CGT | L245R | 31 |
|  | 739 | TGC→CGC | C247R | 36 |
|  | 740 | TGC→TTC | C247F | 18 |

TABLE A-continued

Reported mutations in the PBGD gene

|  | Position | Mutation | Consequences | Reference |
|---|---|---|---|---|
|  | 742 | Ins 8 bp | Frameshift | 24 |
|  | 748 | GAA→AAA | E250K | 24 |
|  | 754 | GCC→ACC | A252T | 36 |
|  | 755 | GCC→GTC | A252V | 36 |
|  | 766 | CAC→AAC | H256N | 27 |
|  | 771 | CTG→CTA | DS (Del exon 12) | 39 |
|  | 771 | CTG→CTC | DS (Del exon 12) | 37 |
| Intron 12 | 771 + 1 | gta→ata | DS (Del exon 12) | 19 |
| Exon 13 | 806 | ACA→ATA | T2691 | 30 |
|  | 820 | GGG→AGG | G274R | 30 |
| Exon 14 | 838 | GGA→AGA | G280R | 25 |
|  | 848 | TGG→TAG | W283X | 30 |
|  | 886 | CAG→TAG | Q296X | 25 |
|  | 900 | Del T | Frameshift | 31 |
| Intron 14 | 912 + 1 | gta→ata | DS (Del exon 14) | 26 |
| Exon 15 | 1062 | Ins C | Frameshift | 38 |
|  | 1073 | Del A | Frameshift | 25 |

In one aspect, the present invention relates to a therapeutic method for AIP patients based on gene therapy.

The gene therapy treatment may involve the following steps.

1. Identification mutations in the PBGD gene causing AIP in humans
2. Selection of human PBGD cDNA sequence for gene therapy
3. Construction of PBGD gene therapy vectors.
4. Production of PBGD gene transfer vector
5. Delivery system of PBGD gene transfer vector 1. Identification of Mutations in the PBGD Gene Causing AIP in Humans Patients having a point mutation in Exon 10 at position 593 TGG>TAG have a change in the amino acid sequence of the PBGD enzyme from W198X (stop codon). This mutation is carried by approximately 50% of all AIP patients in Sweden (Lee J S. et al. Proc. Natl. Acad. Sci. USA, 88, 10912–10915, and 1991). AIP patients with other mutations than W198X, which might also benefit from gene therapy, are given in Table A.

2. Selection of Human PBGD cDNA Sequence for Gene Therapy

There are two isoenzyme forms of human PBGD e.g. erythropoietic and the non-erythropoietic form, which are formed by an alternative splicing mechanism. The non-erythropoietic form has a 17 amino acid extension on the N-terminal end of the erythropoietic PBGD form.

Non-erythropoietic PBGD Form (nPBGD):

Met-Ser-Gly-Asn-Gly-Asn-Ala-Ala-Ala-Thr-Ala-Glu-Glu-Asn-Ser-Pro-Lys-Met-Arg-Val (SEQ ID NO:36)

ATG-TCT-GGT-AAC-GGC-ATT-GCG-GCT-GCA-ACG-GCG-GAA-GAA-AAC-AGC-CCA-AAG-ATG-AGA-GTG (SEQ ID NO:35).

Erythropoietic PBGD Form (ePBGD)

Met-Arg-Val-

ATG-AGA-GTC. . .

The nucleotide and amino acid sequence for human PBGD that will be used for gene therapy differs from that published by Raich N. et al. Nucl. Acid. Res. 14, 5955–5968, 1986 in that the amino acid residue in position 332 is an Asn residue rather than Thr. In order to make the "wild type enzyme" and avoiding formation of antibodies the PBGD sequence has to contain an Asn residue in position 332. The cDNA sequence that will be used for the erythropoietic PBGD form is shown above.

Patient with a defect erythropoietic PBGD enzyme will be transfected with the erythropoietic PBGD cDNA sequence and patients with a defect in the non-erythropoietic form will be transfected with the non-erythropoietic cDNA sequence.

3. Construction of PBGD Gene Therapy Vectors

Adenoviral Vector System

The vector is based on adenovirus type 5 (Ad5), containing three essential genetic loci E.g. E1, E2, E4, encoding important regulatory proteins and one locus E3 which is non-essential for virus growth. Deletion of E1A and E1B region renders the virus replication deficient in vivo. Efficient complementation of the E1 function (recombinant viral stocks) can be obtained in an E1 expressing cell line such as human 293-cell line.

The human PBGD cDNA will be inserted in an adenovirus vector system.

The PBGD transgenes will be driven by the endogenous PBGD promoter or a cytolomega virus promoter (CMV).

Retroviral Vectors

Retroviral vectors are well suited for gene delivery for several reasons:
1. simplicity
2. capacity to integrate up to 8 kbp DNA inserts
3. their safety, non pathogenic to humans
4. easy to improve and manipulate
5. defined integration sites of genes
6. long term regulated expression One major disadvantage with the retroviral vectors though, is that they can only transduce dividing cells.

Most common retroviridae considered for gene therapy, are the lentiviridae and the mammalian C-type viridae. Other type retroviruses have also been considered. One such example, is a Moloney-murine leukemia retrovirus (Mo-MLV), which has ben successfully used to transduce mouse and human fibroblasts with theuroporphyrinogen III synthetase (UROIIIS). (Moreau-Gaudry et al. Human Gene Therapy 6, 13–20, 1995).

The expression of the UROIIIS gene was driven by long terminal repeat (LTR). The UROIIIS cDNA was also successfully transduced by the retrovirus vectors into human peripheral blood progenitor cells.

The erythropoietic PBGD cDNA sequence can be inserted in a retrovbirus vector LXSN (Miller et al Bio Techniques 7, 980–990, 1989) and pMFG (Dranoff et al. Proc. Natl. Acad. Sci. USA. 90,3539–3543, 1993). This will lead to the following constructs e.g. LePSN and pMFG-ePBGD, respectively.

LePSN:

> 1032 bp <
LTR——/cDNA ePBGD/ SV40/ Neo/ —— LTR pMFG-ePBGD:

> 1032 bp <
LTR ——/cDNA ePBGD/ ——LTR

For transduction of non-erythropoietic tissues the non-erythropoietic cDNA (See sequence 12) will be inserted in the LSXN vector and the pMFG vector resulting in the LSnPN and pMFG-nBGD vectors, respectively.

LnPSN:

> 1083 bp <
LTR —— /cDNA nPBGD/ SV40/ Neo/—— LTR pMFG-nPBGD:

> 1083 bp <
LTR——/cDNAnPBGD/—— LTR

The LePSN and LnPSN vectors can be converted to the corresponding virus by transfer into an appropriate host cell line e.g. Ψ CRE as described by (Danos et al. Proc. Natl. Acad. Sci. USA, 85, 6460–6464, 1988). Filtered supernatants from ectopic virus producing cells were added to amphotropic cells Ψ CRIP, in the presence of Polybrene. Clones can be isolated and tested for virus. Clones that show titers over 1.000.000 cfu/ml will be saved (resistant to G418). The LnPSN vector will be cotransfected with the pMCI-Neo plasmid (Pharmacia, Sweden) into the packaging cell line Ψ CRIP. Clones that shows integration of provirus and high expression levels of message will be selected.

Filtrate from supernatants from virus producing cells (erythropoietic PBGD form) can be mixed with Polybrene and incubated with peripheral blood progenitor cells (bone marrow transplant) from an AIP patient for several hours. The transduced progenitor cells can then be transplanted back into an AIP patient.

The success of the treatment will be measured as the increase in the PBGD activity in erythrocytes and reduced excretion of ALA and PBG in the urine. Clinically a success of the treatment can be evaluated as a reduction of frequency of spontaneous acute attacks or drug-induced attacks. This will be a more convenient way of administering the recombinant PBGD enzyme than regular injections. The efficacy of the therapy can be evaluated by measuring the PBGD activity in blood and reduced excretion of PBG and ALA in the urine. Clinically, a successful treatment should result in less number of acute attacks or preferably no more attacks.

Associated Adenovirus System (AAV)

AAV is a non-pathogenic human virus (Parvovirus) carried by more than 80% of all people. The advantage with AAV as compared to retroviral systems is that AAV can transduce both dividing and non-dividing cells. The virus genome, which is small, contains two Inverted Therminal Repeats (ITR) and a REP and CAP functions. The REP and CAP functions can be deleted and exogenous cDNA inserted. Construction of an AAV vector containing the erythropoietic PBGD cDNA can be made. This AAV/IPBGD vector will be suitable to transduce AIP patient's bone muscle cells, as a "muscle factory" for PBGD enzyme production. The PBGD cDNA will be engineered in such a way that a signal sequence for secretion will be added on the 5'-end of the cDNA. This will allow the erythropoietic PBGD enzyme to become secreted from the muscle cells into the blood stream. By this system patients will receive a constant delivery of active PBGD enzyme into the blood stream, which will metabolize PBG thereby avoiding acute attacks.

Non-Erythropoietic

Alternatively, liver cells can be transduced with AAV containing the non-erythropoietic PBGD cDNA. The construct will be engineered in such a way that the translated PBGD enzyme will remain intracellular e.g. contain a Met residue at the N-terminal end of the PBGD enzyme without a signal sequence for secretion in mammalian cells. The PBGD transgene will be transcribed and translated into new PBGD enzymes that will remain intracellularly. Levels of new PBGD enzymes made in the liver will be normalized the PBGD activity to 100%. AIP patients have usually reduced PBGD activity (50–80%) in the liver depending on the mutation and individual variations.

This treatment would alleviate the clinical symptom e.g. acute attacks with abdominal pain and reduce excretion of PBG and ALA in the urine. The AAV containing the non-erythropoietic PBGD form can also be used to correct the genetic defect in other cell types such as neuronal tissue, pancreas spleen e.g. non-erythropoietic tissue, by a similar mechanism.
Erythropoietic The erythropoietic PBGD cDNA can be inserted in an AAV vector and used to transduce erythropoietic cells and stem cells in AIP patients, having a mutation affecting the erythropoietic form of PBGD.

4. Production of PBGD Gene Transfer Vector

Adenovirus have approximately 36 kbp double stranded DNA, containing three essential early gene loci (E1, E2, and E4) encoding important regulatory proteins. Loci E3 codes for a gene product that block immune response to virus infected cells in vivo. The PBGD gene transfer adenovirus vector can be produced by deleting the E1 and E3 loci. The PBGD gene cassette is inserted in that position instead. The virus will be replication defective when the E1 locus has been deleted. Efficient E1 complementation and this high yield of recombinant virus vector (PBGD) can be obtained in an E1 expressing cell line, such as the human 293 cell line. (Graham, F. et al. 1977, Characteristics of a human cell line transformed by DNA from human adenovirus 5. J. Gen. Virol. 36, 59–72).

5. Delivery Systems of PBGD Gene Transfer Vectors

Delivery of viral vectors are based on injection into the patient of a virus particle that will transduce human cells in vivo.

Correction of Point Mutations Causing AIP by Chimeraplasty Gene Repair

The basic technique involves the synthesis of chimeric (RNA-DNA) oligonucleotides. The oligonucleotide will repair point mutations on the chromosome by binding to the site of mutation and create a mismatch. The endogenous "mismatch repair system" which is present in all living cells, will correct the mutation.

The Chimeric oligonucleotides has the following general properties:
a. 68 mer (65–70 is acceptable size)
b. 25 base DNA stretches at the 5'-end homologous to the normal sequence of the gene
c. the 25 base DNA is designed n such a way the 12 bp on each side of the mutation is complementary to "wild-type DNA" where the mutation to be altered is located at position 13
d. the 25 mere contains 4 T bases at the one end to loop back the oligo to the other DNA strand with a 25 base sequence homologous to the other strand of the chromosomal DNA.
e. the second strand is chimeric in that it contains 10 homologous bases of 2'O methyl RNA followed by 5 bases of DNA (containing a central mismatch e.g. correction of the human point mutation by mismatch repair) followed by another stretch of 10 bases of homologous 2'O methyl RNA. This stretch of DNA/RNA is followed with 5 bases of GC clamp and 4 T bases to form the second loop and finally a 5 base CG clamps complementary to the other one.

EXAMPLE A

Correction of the PBGD Mutation at Position 593 TGG>TAG Resulting in W198X

Normal Chromosomal Sequence:

5'-AG CGC ATG GGC TGG CAC,AAC CGG,GT-3' (SEQ ID NO:37)

Gln Arg Met Gly Trp His Asn Arg Val (SEQ ID NO:38)

AIP Chromosomal Sequence:

5'-AG CGC ATG GGC TAG CAC AAC CGG GT-3' (SEQ ID NO:39)

Stop

The sequence of the chimeric oligonucleotide (Heme593W/X) is (SEQ ID NO:40):

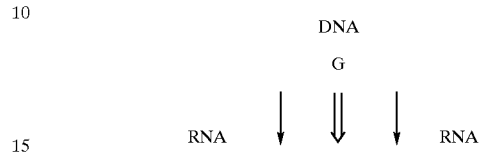

The same principle of chimeric oligonucleotide can be constructed to correct any of the mutations causing AIP depicted in Table A.

Chimeric oligonucleotides can be used to correct any other point mutation causing any of the 8 known Porphyrias in a similarly as described above.

Delivery of PBGD Gene Transfer of Non Viral Vectors to Humans

The chimeric oligonucleotide can be formulated in a vehicles preparation containing anionic or cationic phospholipids or phospholipids mixed with neutral lipids or lictosylated PEI.

Alternatively, the non-viral vectors can be formulated in liposomes containing mixtures of natural phospholipids and neutral lipids.

Specific protein sequences can be incorporated into liposomal membranes, that recognizes cellular receptors for specific targeting of non-viral vectors to a specific cell type such as liver, neuronal tissue or erythropoietic tissues, can be incorporated. Alternatively specific antibodies recognizing specific cellular surface antigens can be used for targeting. Thirdly, carbohydrates on the liposomal membrane can be used for liver uptake of chimeric oligonucleotides.

The formulated chimeric oligonucleotide (HemeBiotech 595 W/X) will be administered by sc. or IV, injections to AIP patients.

The efficacy of the treatment can be evaluated as above. Gene therapy as an alternative treatment of other porphyric diseases The gene therapy strategies outlined herein can also be used for other Porphric diseases. The general principle is to increase the cellular or systemic content of a particular defective enzyme causing the disease. The following Porphyric diseases can be encompassed by this strategy:
1. ALA deficiency porphyria (ADP)
2. Porphyria cutanea tarda (PCT)
3. Hereditary coproporphyria (HCP)
4. Harderoporphyria (HDP)
5. Variegata porphyria (VP)
6. Congenital erythropoietic porphyria (CEP)
7. Erythropoletic protoporphyria (EPP)
8. Hepatoerythropoietic porphyria (HEP)

In the following Examples, preferred embodiments of the invention is disclosed relating to rhPBGD.

EXAMPLE 1

Fermentation of Recombinant Human Porphobilinogen Deaminase (rhPBGD)

Strain PBGD-1 is an E. coli K12 host strain JM105 genotype endA thi rpsL sbcB15 hsdR4 Δ(lac-proAB)

[F'traD36 proAB lacI$^q$ Δ(lacZ)M15] containing the expression plasmid pExp1-M2-BB. Strain PBGD-2 has the same expression plasmid pExp1-M2-BB but the host cell is deleted for the hemC gene to facilitate rhPBGD purification. Since the strain PBGD-2 was not ready at the start of the study, the decision was made to start the study with strain PBGD-1. Both the strains are resistant against both tetracycline and ampicillin, but due to regulatory advantages it was decided to use oxytetracycline as selection pressure. To focus the first part of the study on the expression level of rhPBGD, and not the strain stability, it was decided to start the development with selection pressure in the fermenter. When the expression level was satisfactory strain stability without selection pressure in the fermenter should be investigated. Preliminary tests performed showed that the expression level of rhPBGD was 1,5 times higher at 37° C. compared to the expression at 30° C. At 42° C. it was as much as 3 times higher. Based on this knowledge one would suggest a temperature induction to either 37° C. or 42° C. during the fermentation to boost the rhPBGD production. However, at higher fermentation temperatures the strain stability might be a problem. The time frame was too narrow to study the rhPBGD expression at all three temperatures, so the decision was to start the study without temperature induction and to keep the temperature at 30° C. during the whole process.

Short Description of the Work

During the first two months the strain PBGD-1 was cultivated on agar plates and in shake flasks to obtain information about the strain characteristics. In parallel to this purchase of study dedicated chemicals, build up of the documentation system and technology transfer of the analytical methods took place. When the PBGD-1 intermediary cell bank was prepared the actual fermentation work started. First two "simple" 1-L batch fermentations of strain PBGD-1 were used to test the newly designed substrate and to calculate the maximum growth rate for the strain. After that three 10 L fed batch fermentations of strain PBGD-1 was performed.

As soon as the strain PBGD-2 was available and an intermediary cell bank was prepared, this strain was implemented in the fermentation procedure developed for strain PBGD-1. At present two 10-L fermentations of strain PBGD-2 have been performed. The general outline of the fermentation is starting with inoculum preparation on M9-tc agar plates and shake flasks. The cells are incubated at 30° C. for 24 h on M9-tc agar plates and are then transferred to M9-tc shake flasks. The shake flasks are incubated for 12–14 h at 30° C. The broth from 1–2 shake flasks are used to inoculate the 10 L fermenter containing a minimal medium supplemented with yeast extract, trace elements, thiamine and oxytetracycline as selection pressure. The fermentation starts with a 14-h batch phase where the cells grow at maximum growth rate. The glucose feed is started after 14 h and the feed rate profile is varied between 25–75 ml/h of a 600 gl$^{-1}$ glucose solution.

Broth taken from shake flasks and fermentations have been used to develop the down stream processing and to test and adjust the analytical methods provided. The general outline in the down stream processing is concentration of the fermentation broth on a 0,22 μm cross flow membrane followed by diafiltration (washing) with a buffer to exchange 90–95% of the substrate with buffer. The diafiltered cell concentrate is homogenised in a homogeniser, where the pressure has been varied between 600–1000 bars. The cell debris is then removed from the homogenate either by filtration on the same membrane as mentioned above or by centrifugation. Finally the extract is sterile filtered into sterile containers.

Results

Fermentation

The maximum growth rate for strain PBGD-1 was determined in shake flask experiments and in 1-L batch fermentations. The results are summarized in Table 5 below. The reason for the lower values in the shake flask with fermenter medium is probably acetic acid production and hence lower pH since the pH is not controlled. No experiments have been performed to calculate the maximum growth rate of strain PBGD-2, but from the fact that the batch phase has the same duration as for PBGD-1 we can draw the conclusion that the maximum growth rate is approximately the same.

TABLE 5

Maximum growth rates

| Conditions | Maximum growth rate ($\mu_{max}$) [h$^{-1}$] |
| --- | --- |
| M9-tc Shake flask | 0,3 |
| Shake flask with fermenter substrate | 0,3 |
| 1 L Fermenter with pH controlled at 7,0 | 0,4 |

The developed substrate for the fermentation is given in Table 6 on the next page. When implementing strain PBGD-2 it seems like this strain has different requirements on either the amount of yeast extract or the thiamine concentration in the substrate. When using the substrate developed for strain PBGD-1 the growth stops or lags during the fermentation (PD14). When adding extra yeast extract and thiamine the growth starts again. This pattern is repeated at least two times during the fermentation.

TABLE 6

Fermenter substrate

| Component | Mw [g/mol] | Concentration | Unit |
| --- | --- | --- | --- |
| $(NH_4)_2SO_4$ | 114,12 | 2,70 | [g/l] |
| $KH_2PO_4$ | 136,08 | 3,25 | [g/l] |
| $K_2HPO_4*3H_2O$ | 228,23 | 2,80 | [g/l] |
| $C_6H_5Na_3O_7*2H_2O$ | 258,07 | 0,60 | [g/l] |
| Yeast extract | | 5,00–20,0 | [g/l] |
| $C_6H_{12}O_6*H_2O$ | 198,17 | 10,00 | [g/l] |
| $MgSO_4*7H_2O$ | 246,50 | 1,07 | [g/l] |
| Thiamine chloride $C_{12}H_{18}Cl_2N_4OS*xH_2O$ | | 1,00–10,0 | [mg/l] |
| $H_3BO_3$ | 61,83 | 2,1 | [mg/l] |
| $CuSO_4*5H_2O$ | 249,70 | 10,5 | [mg/l] |
| $FeCl_3*6H_2O$ | 270,30 | 35,5 | [mg/l] |
| $MnSO_4*H_2O$ | 169,02 | 6,6 | [mg/l] |
| $ZnSO_4*7H_2O$ | 287,50 | 5,3 | [mg/l] |
| $CoCl_2*6H_2O$ | 237,93 | 9,3 | [mg/l] |
| $CaCl_2*H_2O$ | 147,02 | 14,0 | [mg/l] |
| $Na_2MoO_4*H_2O$ | 241,95 | 9,3 | [mg/l] |
| HCl | 34,46 | 6,9 | [ml/l] |
| Oxytetracycline $C_{22}H_{24}N_2O_9*HCl$ | 496,90 | 6,0 | [mg/l] |

The strains seem to utilise different components in the yeast extract in a sequential order. The metabolism and respiration is different for different compounds. This gives rise to an irregular fermentation pattern with large changes in the respiration of the population during the fermentation, e.g. the $CO_2$ and the $O_2$ outlet gas analysis and the dissolved oxygen tension (DOT) signal (see FIG. 12).

As the fermentation proceeds, the fermentation broth is gradually coloured bright pink. When centrifuging broth for dry weight analysis it is observed that it is the actual cells and not the supernatant that is pink. The colonies on the M9-tc agar plates used to inoculate the shake flasks are not coloured pink, they are rather yellow or white like "normal" E. coli cells.

The colonies on the agar used for the colony forming units (CFU) analysis from the fermentation are also pink. However, on the CFU plates from PD14, the first fermentation with the new strain PBGD-2, a small portion of yellow or white colonies was observed. This observation was made already from the plates spread with broth from the inoculum shake flask. The percentage of yellow-white cells was varying inn the range 2–8% during the fermentation. Both the white and red colonies were resistant against the antibiotic oxytetracycine. When observing the white and red colonies in the microscope they both appeared as E. coli rod like cells. It was hard to see any clear difference, but possibly the white cells were a little bit shorter than the red ones. To investigate this further shake flask cultivation were started with one red and one yellow colony. The CFU analysis showed that there were only red colonies from the shake flask inoculated with the red colony, but that the white colony gave rise to approximately 70% white and 30% red cells. The rhPBGD activity and protein concentration were measured in the broth from these shake flasks. The results are shown in Table 7 below. The difference in the protein concentration and the rhPBGD activity is in accordance with the difference in the $OD_{620}$ reached in the shake flask, probably due to different size of the inoculum colony.

TABLE 7 rhPBGD activity and total protein from single colony shake flasks

| Start colony | Protein [mg/ml broth] | PBGD activity [U/L broth] | Specific activity [U/mg protein] |
|---|---|---|---|
| White | 0,01 | 9 | 0,8 |
| Red | 0,04 | 27 | 0,7 |

In the Table 8 below a summary of the final values of the fermentations are given. The lower $OD_{620}$ and Dw (dry weight) values in fermentation PD12 is a result of the lower amount of glucose that totally was fed into the fermenter in this fermentation (600 ml compared to approximately 850 ml in PD11 and PD14). It is also interesting to notice the very high expression and specific activity of rhPBGD in fermentation PD14 compared to the earlier fermentations.

TABLE 8

Summary of final fermentation results

| Batch | Strain | Time [h] | $OD_{620}$ | Dw [g/l] | PBGD activity [U/ml broth] | Specific PBGD activity [U/mg protein] |
|---|---|---|---|---|---|---|
| PD11 | PBGD-1 | 27 | 82 | 29 | 7.7 | 2.6 |
| PD12 | PBGD-1 | 31 | 59 | 19 | 15.3 | 1.8 |
| PD14 | PBGD-2 | 30 | 87 | 32 | 39 | 3.1 |

Until now we have achieved the best fermentation results in fermentation PD14. In the FIGS. 12 and 13 the fermentation results from this fermentation with the new strain PBGD-2 are shown. After a 14h batch phase the glucose feed is started according to a schedule with three step changes in the feed rate. However after 16 h the glucose begins to accumulate in the fermenter due to that something else is limiting the growth more. The glucose feed is then stopped and restarted when the glucose concentration becomes limiting again.

Figure 12:
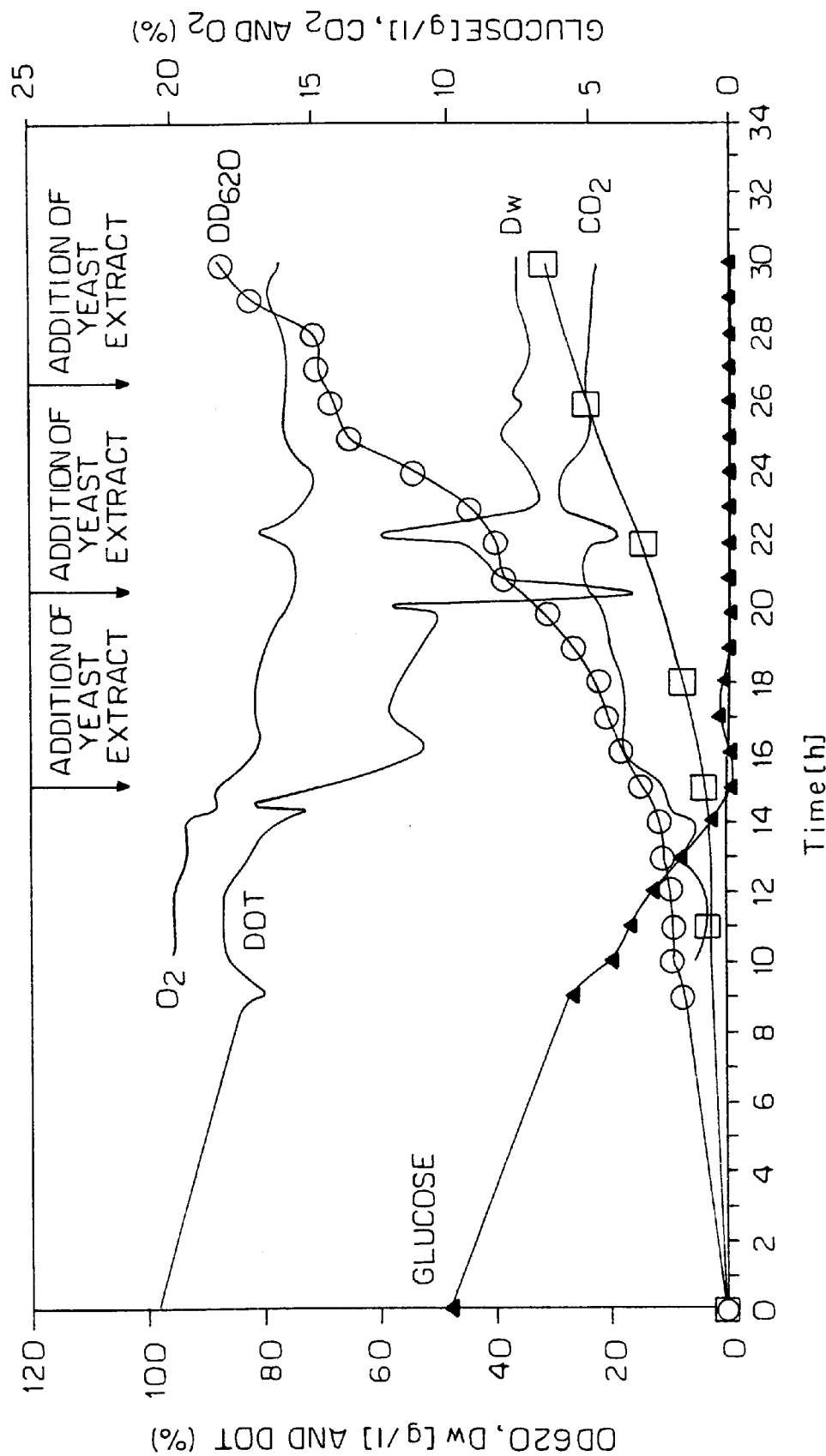

The respiration pattern (i.e., $CO_2$, $O_2$ and DOT signals) indicated that something in the substrate was depleted after 14,5 and 22,3 h and 26, 3h (see FIG. 12). When extra yeast extract and thiamine was added to the fermenter growth respiration increased dramatically for a while. There was a steady increase in the $OD_{620}$ and Dw during the whole fermentation and the final values are rather high. The increase in produced amount of rhPBGD correlates very well with the increase in biomass. This is something that has been observed also in the other fermentations. However, in fermentation PD14 there also seems to be a steady increase in the specific activity of the produced rhPBGD. Something that has been much less pronounced in the other fermentations.

Down Stream Processing

The different broths have been concentrated 1,9–6,9 times, the different values reflect problems with clogging of the membrane. This problem can probably be avoided by not concentrating the broth too much. Instead a somewhat longer diafiltration has to be done. The homogenisation has given a good yield of released enzyme compared to sonication. Removal of cell debris is in the laboratory scale rather easily done by centrifugation. For the production scale it would be preferred to use membrane filtration and because of that filtration has been tested. However, so far the transmission of enzyme through the membrane has been low resulting in low yields. This yield may be improved by better controlled filtration parameters or extended diafiltration. Otherwise a separate could be used in the production.

In Table 9 some data from the down stream processing are shown.

TABLE 9

Summary of down stream results

| Debris Broth removal by | Sterile filtered extract | | | Yield from broth, % | |
|---|---|---|---|---|---|
| | protein mg/ml | activity U/ml | Spec. activity U/mg protein | protein | U |
| PD11 Filtration | 2.7 | 5.1 | 1.9 | 30–60 1) | 35–45 1) |
| PD12 Centrifugation | 31 | 84 | 2.7 | 79 | 120 2) |

TABLE 9-continued

Summary of down stream results

Sterile filtered extract

| Debris<br>Broth removal by | protein<br>mg/ml | activity<br>U/ml | Spec. activity<br>U/mg protein | Yield from broth, % | |
|---|---|---|---|---|---|
| | | | | protein | U |
| PD14 Centrifugation | 32 | 92 | 2.9 | 85 | 67 |
| PD14 Filtration | 3.8 | 11 | 2.8 | 15 | 18 |

1) Uncertainties in analysis, because the methods were not fully evaluated at this time.
2) Uncertainty in volume because of a tube leakage.

Conclusion

Strain PBGD-2 has a maximum growth rate of approximately 0,4 $h^{-1}$ in the fermenter substrate. This is similar to the maximum growth rate of strain PBGD-1, however the substrate requirement seems to be different for strain PBGD-2. An increase of the initial yeast extract and thiamine concentration in the substrate to 20 $gl^{-1}$ and 10 $mgl^{-1}$ respectively supports growth to a biomass similar to those achieved with the old strain PBGD-1.

The general fermentation process outline is a 14 h batch phase followed by a 16 h feed phase were the glucose feed rate is increased in three steps.

The production of rhPBGD correlates very well with the biomass production and the specific activity of the rhPBGD also seems to increase during the fermentation. The best result so far with strain PBGD-2 is a rhPBGD concentration of 39 U/ml and a specific activity of 3,1 U/mg protein after 30-hour fermentation. The final dry weight and $OD_{620}$ was 32 $gl^{-1}$ and 87 respectively. The plasmid stability is good during the fermentation when oxytetracycline is present as selection pressure.

EXAMPLE 2

Development of a Purification Process for Recombinant Human Porphobilinogen Deaminase (rhPBGD)

Introduction

For the capture step a weak anion exchange (DEAE-Sepharose FF) matrix has been tested primarily, because this has been the most common initial step for purification of PBGD. The disadvantage with anion exchange is that endotoxins and DNA adsorb on this type of gel. There is a risk that these impurities are coeluted with rhPBGD. To use a cation exchange in this project is not possible, because pI for rhPBGD is too low. For that reason a hydrophobic gel has also been tested as a capture step.

Material and Methods

Cells extract

Cell extract (PD12, see Example 1) was supplied frozen (8×50 ml) from Biogaia. After the initial thawing a precipitation was found in the sample. The extract was centrifuged and the next day a new precipitation was found. This means that the extract has to be centrifuged in connection to a chromatography experiment. The protein content in the extract (BCA) was estimated to 29 mg/ml and the enzyme activity was found to be 63 U/ml. The pH and conductivity were estimated to 7.0 and 6 mS/cm, respectively.

Ion-Exchange

A DEAE-Sepharose FF hitrap (1 ml) column was used. The gel was equilibrated with Tri-HCl 25 mM, pH 8.5. The pH of the extract was adjusted to pH 8.5 with NaOH 5M and the sample volume applied on the gel was 1.4 or 2.0 ml.

After the sample has been applied, the gel was washed with 15 column volumes with equilibration buffer. For the desorption of the gel the following KCl concentrations have been tested; 40, 120, 150 and 300 mM. Finally, after every experiment the gel was cleaned with NaOH 1M.

Hydrophobic interaction chromatography

A Butyl-Sepharose 4 FF hitrap (1 ml) column was used. The gel was equilibrated with potassium 1.0–1.3M pH 7.5 To the extract, potassium phosphate (2.5M) was added to an end concentration of 1.0–1.3M and the sample volume applied on the gel was 2.0 ml. After the sample has been applied the gel was washed with 15 column volumes with equilibration buffer. For the desorption of the gel 500 mM, 20 mM potassium phosphate and water were tested. Finally, after every experiment the gel was cleaned with NaOH 1M.

Results

Ion-exchange

In FIGS. 14 and 15 chromatograms from two DEAE runs are shown. In Table 10 the results from these runs are shown. The difference between these experiments are that peak b in the first run was desorbed with 120 mM KCl and 150 mM in the second. Further, in the first run less sample was applied and the gel was also desorbed with 300 mM KCl. The recovery was in the best experiment found to be 75% and the yield 47%. To get this recovery and yield 300 mM KCl has to be used. The purity of rhPBGD in peak b (DEAE2) was estimated to 31% (RPC).

Hydrophobic interaction chromatography

In FIG. 16 a chromatogram from a Butyl run is shown. In Table 11 the result from the run is shown. In this experiment 1.3M potassium phosphate was used and the desorption was done with water. Conductivity in peak b was found to be 60 mS/cm. The recovery was calculated to 78% and the yield 75%. In an investigation it was found that precipitation was formed in the extract at a potassium phosphate concentration of 1.5M. The purity of rhPBGD in peak be was estimated to 40% (RPC).

Comments and Conclusions

From the results of the experiments it can be seen that the mass balance in all experiments are not in balance. This seems to be valid for all analyses. The main reasons for this are probably insecurity of the analyses and that all proteins are not eluted from the gel. The first reason is confirmed by the enzyme activity that seems to be too high in the extract when high concentration of potassium phosphate is added. The second reason is confirmed by the elution peak with NaOH in ion-exchange experiments. This peak is not analyzed. For the hydrophobic matrix a cleaning with organic solution can be necessary.

The conclusion of the results so far is that the Butyl-Sepharose 4 FF seems to be the best alternative for the capture step. The main reason for that is the higher yield of rhPBGD. Another advantage to use Butyl-Sepharose 4 FF is the small peak after cleaning with NaOH 1M compared with the large peak in DEAE-Sepharose FF runs. This probably means that few impurities stick on Butyl matrix. On the other hand there is a risk that a precipitation is formed when adding potassium phosphate. A desalting before the next chromatography step can be necessary, caused by the high ion strength in the product peak.

imidizole, a molecule identical to the histidine side chain, in the elution buffer which competitively dislodges the tagged protein off the support. The purpose of this study is to obtain pure rhPBGD-His for antibody production and for use as a standard in assays and protein purification.

Study objectives

TABLE 10

Ion-exchange

| | Applied | | | Peak a | | | Peak b | | | Peak c | | |
|---|---|---|---|---|---|---|---|---|---|---|---|---|
| Exp. | BCA mg | A280 mg | Act. U | BCA mg | A280 mg | Act. U | BCA mg | A280 mg | Act. U | BCA mg | A280 mg | Act. U |
| DEAE1 | 37 | 166 | 76 | 10 | 122 | 21 | 5 | 6 | 29 | 9 | 11 | 7 |
| DEAE2 | 42 | 229 | 129 | 17 | 143 | 56 | 10 | 14 | 25 | — | — | — |

TABLE 11

Hydrophobic interaction chromatography

| | Applied | | | Peak a | | | Peak b | | | Peak c | | |
|---|---|---|---|---|---|---|---|---|---|---|---|---|
| Exp. | BCA mg | A280 mg | Act. U | BCA mg | A280 mg | Act. U | BCA mg | A280 mg | Act. U | BCA mg | A280 mg | Act. U |
| Butyl | 31 | 137 | 93 | 7 | 84 | 3 | 11 | 23 | 70 | — | — | — |

EXAMPLE 3

Development of a Method for the Purification of Recombination Human Porphobilinogen deaminase with a "His-Tag" (rhPBGD-His)

Nature and purpose of the study

Many groups have reported in the literature on the purification of porphobilinogen deaminase from various sources including *E. coli* and Human erythrocytes (Anderson P. M. and R. J. Desnick, 1979, The Journal of Biological Chemistry 255(5): 1993–99, Awan S. J. et al. 1997, Biochemistry 36(30): 9273–82, Grandchap B. et al. 1987, Eur. J. Biochem. 162(1): 105–10, Jordan P. M. 1994; Wiley, Chichester (Ciba Found Symp 180). p 70–96, Jordan P. M. et al. 1988, Biochhem J. 254:427–435, Lambert R. et al. Wiley, Chichester (Ciba Found Symp 180), p97–110, Louie G. V. et al. 1996, Proteins 25(1): 48–78, Maniatis T., E. F. Fritsch, J. Sambrook. Molecular Cloning (A laboratory Manual) Cold Spring Harbor Laboratory. 1982, Miyagi K. et al. 1979, Proc. Natl. Acad. Sci. 76(12):6172–76, Racich N. 1986, Nucleic Acids Research 14(15): 5955–67, Shoolingin-Jordan P. M. et al. 1997, Methods in Enzymology, 281:317–327). Most use a combination of ion exchange, hydrophobic interaction and size exclusion chromatography to obtain fairly pure protein preparations. With the engineering of 5 additional Histidine residues on the C-terminus of recombinant human porphobilinogen dearinase. rhPBGD we have a convenient "Tag" to help with purification. Histidine has an affinity to electropositive transition metals such as nickel, copper, zinc and cobalt. When a series of 6 or more electron-rich histidine residues are expressed on the end of a protein they can function as an anchor, firmly attaching the protein to a solid support coated with metal-lions. Very thorough washing can be done without dislodging the bound moiety. Elution can be accomplished in one of two ways, either by decreasing the pH to protonate the imidizole nitrogen (pKa of 5.97) of histidine, or by including The objective of this study is to obtain 10 mg of highly pure active rhPBGD-His.

Study Plan

Plan outline

1. Optimize induction time for the expression system and lysis
2. Purity 10 mg of rhPBGD-His for antibody production and standard
    (2.1) 2 liter scale induction and lysis of strain
    (2.2) DEAE ion exchange chromatography
    (2.3) Immobilized metal affinity chromatography
3. Characterization of rhPBGD-His
    (3.1) SDS-PAGE
    (3.2) Amino acid analysis
    (3.3) Specific activity
    (3.4) HPLC
    (3.5) Mass spectrometry
    (3.6) Amino terminal sequencing Plain body 1. Expression of rhPBGD-His is regulated by the bacterial Taq promoter, a derivative of the lac promoter which is inducible with IPTG (See FIG. 17 for plasmid map). Different proteins are produced at different rates in *E. coli* upon induction. This necessitates the optimization of the time required for optimum rhPBGD-His yield upon induction. To accomplish this a culture in mid-log phase will be induced with an excess of IPTG and expression followed at timepoints with activity and protein concentration measurements. After induction the cells must be lysed to release rhPBGD-His. Of the options available, sonication the best for this scale of purification. It is compatible with any buffer system and should not be damaging to the protein. To follow efficiency of lysis, absorbance at 600 nm will be measured after each cycle.
2. For use as a standard and for antibody production at least 10 mg of rhPBGD-His will be purified.

(2.1) For protein purification a 2 liter tack culture of the strain producing rhPBGD-His is sufficient. The culture will be inoculated with a fresh over-night culture of cells and grown to mid long phase then induced with IPTG.

(2.2) Plans are to utilize a two step purification process. After lysis the debris will be removed by centrifugation and supernatant loaded onto a DEAE ion exchange column. This will remove the vast majority of contaminants from the lysate and leave a limited number of protein contaminants in the elution fractions containing rhPBGD-His. Protein will be loaded in a high pH and low ionic strength buffer to ensure binding of the weakly charged rhPBGD-His. Extensive washing will be used to remove material that is not firmly bound to the column. A very shallow step gradient of KCl will be used to elute rhPBGD-His. This should separate the different forms of rhPBGD-His with differing charge properties from each other. Separation of different charged forms of PBGD, by ion exchange chromatography, has been reported by others (Anderson P. M. and R. J. Desnick, 1979, The Journal of Biological Chemistry 255(5) 1993–99, Jordan R. M. et al. 1988, Biochhem. J. 254:427–435, Miyagi K. et al. 1979 Proc. Natl. Acad. Sci. USA 76(12):6172–76).

(2.3) The second chromatographic step planned is a column containing Talon fast flow immobilized cobalt metal affinity resin (Clontech). This makes use of the 6-residue histidine tract at the amino terminus of the recombinant protein. Initially, a metal chelating resin (Pharmacia) charged with nickel (Sigma) was tried for purification of rhPBGD-His but it was found to bind other proteins in the lysate as well which coeluted with rhPBGD-His. Although this cobalt resin has less binding affinity to His tagged proteins than nickel it retains the high binding capacity and is more discriminating which proteins to bind. This leads to elution from the metal with a lower concentration of imidizole or with higher pH and achieves a higher level of purity. The cobalt is also bound more tightly to the matrix by a tetradentate metal chelator, effectively eliminating the leaching of metal ions from the solid support during purification. The loss of reactive metal ions during elution is common problem with nickel based affinity columns personal communications) which can lead to unwanted precipitation of purified proteins.

3. rhPBGD-His will be characterized by the following methods:

(3.1) The first measure of protein purity will be by SDS-PAGE (polyacrylamide gel electrophoresis). This method will also give an indication of the molecular weight of the protein being produced.

(3.2) To determine the specific activity of rhPBGD-His in the preparation it is first necessary to accurately determine protein concentration in solution. Amino acid analysis will be used as an accurate method. The method also provides the amino acid composition of the protein. The concentration can be used to establish an extinction coefficient of rhPBGD-His.

(3.3) Activity of the enzyme is an important measure of correct structure of the enzyme. The proper structure, equivalent to that produced in humans, is essential for rhPBGD-His to be used as a therapeutic. Any deviation from the natural structure can cause activation of the patient's immune system. Historically, activity of porphobilinogen deaminase has been measured in one of two ways, either by the metabolism of porphobilinogen substrate or by the formation of preuroporphyrinogen product. In the reaction catalyzed by PBGD, porphobilinogen monomers are covalently attached one at a time starting from the free alpha position of the dipyrromethane cofactor. After four molecules are added the linear tetramer of PBG, preuroporphyrinogen, is spontaneously released by hydrolysis from the cofactor, regenerating the active holoenzyme with covalently attached cofactor for further reactions (See FIG. 18). After release the tetrapyrrole is circularized by the next enzyme of the heme pathway, uroporphyrinogen III synthase, forming uroporphyrinogen III, the central ring of heme and vitamin B12 in animals and chlorophyll in plants. The liner preuroporphyrinogen molecule can instead be oxidized to uroporphyrin with benzoquinone creating a molecule, which absorbs light at 405 nm. This is the basis for the activity assay used to measure PBGD activity (3.4) The rhPBGD-His preparation will be further characterized by mass spectrometry, which will give an accurate measure of rhPBGD-His molecular weight and potentially identify molecular heterogeneity in the preparation. rhPBGD-His can exist with 1,2,3 and 4 substrate molecules bound to it. Each substrate molecule added to the holoenzyme will add roughly 209 daltons to the mass, which is detectable through mass spectrometry.

(3.5) Characterization by reversed phase HPLC will provide purity data.

(3.6) Amino terminal sequencing of rhPBGD-His will be used to ensure the correct amino terminus.

Materials and Methods

Induction and Lysis:

From a freshly streaked colony, a culture of pExp-2 in JM105 was grown for 13.5 hours in 100 ml LB (10 g/l bacto-tryptone, 5 g/l bacto-yeast extract, 10 g/l NaCl pH 7.0)+100 µg/ml ampicillin in a 500 ml baffled flask at 37° C. at 350 rpm. The optical density measured at 600 nm reached 1.6. This culture was used to inoculate 2 liters of terrific broth (12 g/l bacto-tryptone, 24 g/l bacto-yeast extract, 4 ml/l glycerol, 2.31 g/l KH2PO4, 12.54 g/l $K_2HPO_4$ (Maniatis T., E. F. Fritsch, J. Sambrook, Molecular Cloning (A laboratory Manual) Cold Spring Harbor Laboratory, 1982) with 100 µg/ml ampicillin and split into four 2 liter baffled flasks with 400 ml each and two 1 liter baffled flasks with 200 ml culture each. These were grown at 37° C. with 350 rpm in a New Brunswick Scientific Innova 4000 incubator. When reaching an optical density of 0.7 at 600 nm the Taq promoter was induced with 4 mM IPTG, causing rhPBGD-His protein to be made. Growth was followed by hourly readings of absorbance at 600 nm. After 9 hours the cultures were stopped by chilling to 0° C. after an absorbance of 1.93 was reached. The culture was centrifuged, 4×250 ml at a time, for 10 min at 4,000 xg in a Beckman Avanti J251 centrifuge with a JLA-16.250 rotor. Supernatant was decanted and the remainder of the culture was added to the cell pellets and spun for an additional 10 min. The pellets were resuspended in 2 pools of 250 ml 50 mM Tris/Cl pH 8.5 (prechilled) each and stored for 8 hours on ice. Cells were centrifuged for 10 min at 4,000 xg, liquid decanted and resulting pellets weighed in the bottles to determine the wet weights. Cells were then resuspended in 400 ml ice cold 50 mM Tris/HCl pH 8.5 and lysed by sonication with a Branson Sonifier 450 with ½ inch diameter stepped, tapped horn.

Each round was for 30 seconds at maximal power with constant duty cycle in a Pyrex 150 ml glass beaker on ice. Lysate was mixed between cycles by either drawing into a 50 ml pipet a few times or by pouring between beakers on ice. Progress of lysis during sonication was ascertained by reading absorbance of the lysate at 600 nm. After six rounds of sonication for each of the 100 ml aliquots of cells, debris was removed by centrifuging at 16,000 xg for 30 minutes at 4° C. Lysate was then pooled and vacuum filtered through a 0.22 μm Durapore membrane (Millipore) to remove any remaining particulate matter.

DEAE Sepharose Chromatography:

The first chromatographic step in purifying rhPBGD-His was by ion exchange chromatography on a DEAE Sepharose fast flow column (Pharmacia). A 2.5×50 cm Spectrum LC column with degassed resin was washed extensively with degassed 25 mM Tris/HCl pH 8.5 buffer. Filtered lysate (380 ml) was applied to the column at 5 ml/min. The column was then washed with 720 ml 25 mM Tris/cl pH 8.5. Elution of bound rhPBGD-His was with a shallow step gradient of KG from 50 to 120 mM in 10 mM increments in 25 mM Tris/HCl pH 8.5 and degassed. Volumes for each step varied from between 105 and 470 ml depending on the elution profile (see Table 12).

TABLE 12

| 0 mM KCl | 50 | 60 | 70 | 80 | 90 | 100 | 110 | 120 |
|---|---|---|---|---|---|---|---|---|
| 720 ml | 470 | 120 | 175 | 270 | 105 | 130 | 180 | 300 |

Fractions were collected about every 50 ml. Absorbance at 280 nm was followed closely during elution. The next step was only applied after the absorbance had declined following a peak. BioRad's protein assay II in microliter format was used per manufacturer's protocol to assay the amount of protein in each fraction. Coomassie stained 10% acrylamide Bis/Tris gels (Novex) were then prepared, with 5 μg protein in each lane, to characterize the purity of each peak.

Cobalt Affinity Chromatography:

The resin slurry was degassed prior to pouring into a 2.5×30 cm Spectrum LC column. It was then washed extensively with degassed 25 mM Tris/HCl pH 8.5/150 mM NaCl at a flow rate of 5 ml/min. The sodium chloride was included to decrease protein to protein ionic interactions and to reduce ion exchange effects with the column matrix itself. A relatively high pH of 8.5 was used to keep rhPBGD-His well above the pI, and therefore negatively charged, to maintain high solubility during the purification. Two consecutive rhPBGD-His affinity purifications were then run on the column. The first sample loaded was a sterile filtered pool of the entire first beak of eluate of activity from the DEAE sepharose column including fractions 9 through 12. The column was then washed with 2 liters of 25 mM Tris pH8.5/150 mM NaCl at 8 ml/min. To elute bound contaminants the column was then washed with 100 ml of 25 mM Tris pH 8.5/150 mM NaCl/5 mM imidizole at 5 ml/min followed by 100 ml of 10 mM imidizole buffer solution. Elution of his tagged protein was with 25 mM Tris pH8.5/ 150 mM NaCl/50 mM imidizole at 5 ml/min. A final elution with 100 mM imidizole was included to be certain all rhPBGD-His was eluted. To prepare the column for the second loading it was merely washed with ~100 ml of 25 mM Tris pH8.5/150 mM NaCl. It was hoped that rhPBGD-His would displace the imidizole bound to the column (which turned out to be the case). The second loading of the column was with a sterile filtered pool with ~900 ml of all remaining peaks of activity from the DEAE Sepharose column at a flow rate of 5 ml/min. The column was then washed with 2 liters of 25 mM Tris pH8.5/150 mM NaCl at 5 ml/min, followed by imidizole containing buffers as with the first run above.

Polyacrylamide Gel Electrophoresis: (SDS-PAGE)

Gel electrophoresis was with the Novex system with Nupage 10% Bis/Tris gels run at 125V for 2 hours with or without reducing agent. Staining with 50% methanol/10% acetic acid/0.25% Coomassie brilliant blue R-250 for 2 to 4 hours. Destaining was in 30% methanol/10% acetic acid in a Bio-Rad gel destainer.

Amino Acid Analysis:

Amino acid analysis was performed by AAA Laboratory (6206 89$^{th}$ Avenue Southeast, Mercer Island, Washington 98040). rhPBGD-His was hydrolyzed for 20 hours with 6N-HCl/0.05% mercaptoethanol/0.02% phenol at 115° C. Serine was increased by 10% and Threonine increased by 5% to compensate for destruction of the individual acids during hydrolysis. A Beckman 7300 Amino Acid Analyzer was used coupled with System Gold software. Analysis was performed by post column derivitization with ninhydrin using the ion-exchange chromatographic methods developed by Moore and Stein.

PBGD Activity Assay:

We performed assays in 96 well microtiter format with validation in cuvets. Procedures were derived from published procedures (Awan S. J. et al. 1997, Biochemistry 36(30): 9273–82, Shoolingin-Jordan P. M. et al. 1997, Methods in Enzymology, 281:317–327). From 0.125 to 8 μg of purified rhPBGD-His protein per well have been used to determine enzymatic activity. Assay buffer is 50 mM Tris/ HCl pH 8.2 with 1.0 mg/ml BSA (Sigma fraction 5) and 10 mM DTT. A Perkin Elmer 9700 PCR machine was used for thermal regulation, allowing for tight control of the temperature and reaction time. Assays have been started in two ways. One method was to start the reactions at 37° C. with prewarmed substrate in a PCR block. Strategic placement of pauses in a thermocycle program was used with beeping at defined intervals for both addition of the substrate and for stopping the reaction. An example cycle program is shown in Table 13 with reaction times varying from 10, 20, 40 and 60 minutes.

The reaction block is a 96 well block with tubes arranged in an 8×12 matrix. It is kept throughout at 37° C. The reaction is initiated by adding PBG to eight tubes in the first row using an eight-channel pipettor. The addition is staggered so that each row receives PBG every 30 seconds. A ten second pause and beep interval is setup every 20 seconds to signal each addition at the end of the period. In this fashion all the 96 reactions are started which takes a total of six minutes. At the end of a further four-minute incubation, the first three rows are stopped in a staggered manner giving a total of a ten-minute incubation period. This procedure is repeated for the next three rows after an additional ten minutes amounting to a total of twenty-minute reaction time. This scheme is illustrated in Table 13. The p@37 represents the 10-second beep period which is configured in the thermocyclor as a pause plus beep interval.

TABLE 13

| start add PBG | stop 10 min | stop 20 min | stop 40 min | stop 60 min |
|---|---|---|---|---|
| ⊢—12X—⊣ | ⊢—3X—⊣ | ⊢—3X—⊣ | ⊢—3X—⊣ | ⊢—3X—⊣ |
| 37  p@37 | 37  37  p@37 | 37  37  p@37 | 37  37  p@37 | 37  37  p@37 |
| 20 sec 10 sec 4 min | 20 sec 10 sec 10 min | 20 sec 10 sec 20 min | 20 sec 10 sec 20 min | 20 sec 10 sec |

Reactions were stopped by acidification with HCl/p-benzoquinone solution. The final concentration of HCl used was 1 molar. Benzoquinone, which oxidizes the uroporphyrinogen to uroporphyrin was used at a final concentration of 0.002% w/v (from 0.2% stock solution in methanol). At defined intervals the 150 µl samples were removed from the reaction tubes and added to 850 µl HCl/p-benzoquinone solution in wells of a 96 well X 2 ml plate on ice. The second method of initiating the assay was to set up the reactions complete with substrate ice then to transfer to the PCR block for incubation at 37° C. Following the reaction the block was brought to 4° C. to stop the reaction after which samples were removed and added to HCl/p-benzoquinone solution. For both methods the incubation was allowed to proceed for 20 minutes on ice and in the dark after the last addition of reaction solutions. Then the plate was centrifuged for 10 min at 350 rpm in a swing out rotor in a GS-6KR centrifuge to pellet precipitated protein (mostly BSA). 250 µl was removed to a Corning 96 well assay plate. Absorbance was measured at 405 nm with a 605 nm reference wavelength in a BioTek FL-600 plate reader. Selected samples (normally the standard curve) were diluted 10X with 1M HCl and read in a quartz cuvet in a Beckman DU640B spectrophotometer at 405.5 nm. A 605 nm reference wavelength was used to subtract out background absorbance. These measurements in cuvets produced a conversion factor from 1 cm pathlength reads to the plate data. Analysis was performed using the KC4 software included with the plate reader and with excel spreadsheets. An extinction coefficient of 548 $M^{-1}cm^{-1}$ was used to quantitate the oxidized reaction product (Shoolinging-Jordan P. M. et al. 1997, Methods in Enzymology, 281:371–327).

HPLC:

HPLC analysis were performed at the University of Washington Mass Spectrometry Analysis Facility for HPLC. Samples were prepared free of salts for mass spectrometry analysis by HPLC on a C4 columns and eluted with an increasing gradient of acetonitrile. The instrument used was an Applied Biosystems (ABI) 140A Solvent Delivery System with an ABI 785A Programmable Absorbance Detector.

Mass Spectrometry:

Mass spectrometric analysis was performed at the University of Washington Mass Spectrometry Analysis Facility. One tenth of the HPLC run within the main elution peak was diverted prior to the absorbance detector to a Perkin Elmer SCIEX AP13 Biomolecular Mass Analyzer for electro-spray mass spectrometry. Analysis was by HyperMass method on an average of 16 peaks (for Cobalt run #1 eluate).

Amino Terminal Sequencing:

Amino terminal sequence analysis was performed at the University of Washington Mass Spectrometry Analysis Facility. An ABI 477A Protein Sequencer was used with an ABI 120A PTH Analyzer.

Results

Purification:

Induction and Lysis;

Growth of the 2-liter culture of bacteria slowed down after the first hour but growth still continued to 9 hrs (see Table 14).

TABLE 14

| start | 1 hr | 2 hr | 3 hr | 4 hr | 5 hr | 6 hr | 7 hr | 8 hr | 9 hr |
|---|---|---|---|---|---|---|---|---|---|
| 0.699 | 1.300 | 1.521 | 1.607 | 1.660 | 1.732 | 1.797 | 1.841 | 1.890 | 1.927 |

After about 3 hrs of induction cells tended to clump together with most turbidity settling out of the broth by gravity in about an hour. Final density of cells stayed low for growth in a rich media such as terrific broth but final weight of pellets was adequate. The total wet weight was 35.3 g, corresponding to 17.7 g/liter culture. Interestingly the cells were orange/pink probably due to various intermediates in the heme biosynthetic pathway. It is clear from the low growth rate and final densities achieved that cultures were limited by the amount of oxygen available.

Lysis by sonication was essentially complete after 5 cycles as seen by following absorbance readings (Table 15).

TABLE 15

| # rounds | 0 | 1 | 2 | 3 | 4 | 5 | 6 | 7 |
|---|---|---|---|---|---|---|---|---|
| OD600 | 30.33 | 20.15 | 12.90 | 9.43 | 6.14 | 3.86 | 3.31 | 2.99 |
| % down | — | 34 | 36 | 27 | 35 | 37 | 14 | 9.7 |

It appears from the % decrease of optical density that for each of the first 5 rounds of sonication, about the same percentage of cells were lysed. After this the percentage of newly lysed cells dropped rapidly. For each of the first 4 rounds viscosity of the lysate was relatively high due to the presence of unfragmented genomic DNA but this decreased significantly after further rounds from shearing of the DNA into smaller fragments.

DEAE Sepharose:

Elution of proteins from the DEAE ion exchange column occurred in 4 distinct peaks as seen in the elution profile in FIG. 19 and by protein assay in Table 16. SDS-PAGE analysis of the eluted fractions shows that these peaks contain four separate peaks of rhPBGD-His eluted with the step gradient of KCl (FIG. 20). The first and major peak was eluted in fractions 9 through 13 with 50 to 70 mM KCl. As seen by gel analysis (see FIG. 20) purity was fairly good for a first step of the purification, especially in fractions 10 through 13. The second peak eluted in fractions 15 through 18 with 80 mM KCl. The major contaminant in this peak, in about equal molar proportions to desired product, was a protein running at about 5 kDa smaller than rhPBGD-His. The third peak in fractions 20 through 23 eluted with 90 to 100 mM KCl and had less visible contaminants than the second peak. The fourth and final peak eluted in fractions 26 through 29+ with 110 to 120 mM KCl. The fractions were split into 2 pools for further purification. The first pool, comprising the major peak of rhPBGD-His elution contained fractions 9 through 12. The second pool contained fractions 13 through 29 along with the next 50 ml of 120 mM KCl elution buffer. These two pools eluted by on exchange contained 877 mg protein out of 3253 mg loaded, corresponding to a 3.7 told decrease in total protein (See Table 16).

Cobalt Affinity:

From the first cobalt run the majority of rhPBGD-His eluted in a sharp peak with a volume of 30 ml upon addition of 50 mM imidizole (see Table 17 for protein assay and FIG. 22 for SDS-PAGE results). A final elution with 100 mM imidizole released no detectable protein absorbing at 280 nm. In the second cobalt run (FIG. 21) surprisingly, the first imidizole wash of 5 mM eluted a small uncolored peak of absorbance with a volume of about 50 ml. The second wash with 10 mM imidizole then eluted a larger and broader orange/pink colored peak of about 150 ml. Further elution with 50 mM imidizole yielded a large sharp uncolored peak of 23 ml.

Characterization:
Amino Acid Analysis:

Amino acid analysis of 3 of the fractions (Cobalt run #1 50 mM imidizole eluate (in duplicate,) Cobalt run #2 10 and 50 mM imidizole eluates) yielded conclusive data that rhPBGD-His was being purified. Results from the analysis allowed for a very accurate measure of protein concentration calculated from the concentration of individual amino acids (see Table 18).

Specific Activity:

Specific activity of the first 50 mM imidizole eluate of rhPBGD-His from the cobalt column turns out to be high at approximately 24 L/mg (Units are in $\mu$mol PBG consumed per mg protein in one hour). Activity of rhPBGD-His was found to be strongly dependent on pH with a sharp rise from 7.0 to 8.0 where it approached a plateau. The optimum was around pH 8.2. The optimum PBG substrate concentration was found to be around 1 mM. rhPBGD-His had activity with all concentrations of PBG, however with amounts less than 1 mM the reaction was limited by available substrate, decreasing both the Vmax and the linearity over time as substrate was depleted. It was not found to be necessary to decolorize remaining benzoquinone with sodium metabisulfite as used in a published assay (Shooligin-Jordan P. M. et al. 1997; Methods in Enzymology, 281:317–327). Strangely enough if acidification and oxidation were done in a smaller total volume (240 $\mu$l vs 1 ml) as done by this research group then a highly colored product develops during the incubation on ice. This product must be decolorized with a saturated solution of sodium metabisulfite to obtain accurate reaction absorbances. There was no significant difference in enzymatic activity found as measured by these two variations of the method.

Generally assays have been set up with both time and enzyme concentration as variables. This allows for a more detailed analysis of the results with a built in validation. If activity is fairly linear from different timepoints at any enzyme concentration then it can be inferred that substrate is not limiting and that reaction measurements are valid over that range. If a measurement is taken at only one timepoint then there is no indication of whether the enzyme is still functioning at V-max.

Reaction volumes in 96 well format have been limited by the size of PCR tubes to 150 $\mu$l. Volumes from between 50 and 150 $\mu$l have been tried with a noticeable increase in linearity over time and with increasing enzyme amounts seen with the larger volumes. Additional increases in volume would make even more substrate available and dilute the protein further, thereby increasing the linearity over time and enzyme concentrations. However the increase in cost of the assay from PBG substrate would be substantial.

For routine analysis of similar protein preparations at similar concentrations it should be possible to standardize the assay and use far fewer data points and still obtain an accurate measure of PBGD activity. Optimally a standard curve of rhPBGD-His of known activity would be included to validate the results and to simplify analysis. Basically multiple variables including time would be internally controlled. With a four-parameter logistic curve of the standards one could use any time point and a wide range of sample concentrations to obtain accurate activity measurements. Single use aliquots of highly pure rhPBGD-His could be stored frozen for use as standards.

Mass Spectrometry:

Mass spectrometry of the 50 mM imidizole elution peaks from the two cobalt runs yielded molecular weights of:
$1^{st}$ cobalt run eluate: 38,816.8, standard deviation=3.68
$2^{nd}$ cobalt run eluate: 38,814.6, standard deviation=4.70
$1^{st}$ cobalt eluate dialyzed for antibodies: 38.817.1, STD deviation=3.33

These weights corresponds to the holoenzyme without any additional substrate molecules attached.

Evaluation and conclusions

We found that with a simple two step purification process involving ion exchange and cobalt affinity chromatography we could achieve a yield of 173 mg/l rhPBGD-His with a purity of greater than 98% starting from a bacterial crude lysate. Each one of the enzyme intermediate complexes is stable and can be independently isolated (Anderson P. M. and R. J. Desnick, 1979, The Journal of Biological Chemistry 255(5): 1993–99, Jordan P. M. et al. 1988, Biochem. J. 254:427–435, Miyagi K. et al. 1979, Proc. Natl. Acad. Sci. USA 76(12):6172–76). This may be a major contributing factor to the differential binding of different enzyme fractions to the DEAE ion exchange matrix. Due to the negative charges contributed by acetate and propionate side groups on the growing chain of porphobilinogen molecules it could be theorized that binding affinity to the ion exchange resin would be in the order, E<ES<ES2<ES3. That would imply that the first peak could be the holoenzyme followed by the others in the same order of the reaction progression. The cobalt column also eluted rhPBGD-His in different fractions during the second run. It is strange that the elution profile from the second run was different from the first. It would be expected that all closely related proteins with a his-tag would bind to cobalt with the same affinity. This implies that either the His-tag is partially digested away or partially obscured due to protein conformational changes or charge interactions. The difference in elution characteristics may also be due to differences between the various enzyme-substrate intermediate complexes as hinted by the color difference in the 10 mM elution peak. From a report in the literature by Jordan P. M. 1994, Wiley, Chichester (Ciba Found Symp 180), p 70–96, the ES2 intermediate complex has a pink colored chromophore. The 10 mM imidizole fraction from the second cobalt column run has a pink color while the other fractions do not. This implies a separation of different enzyme substrate intermediates in different fractions. If the colored protein peak is predominantly composed of the ES2 intermediate then it could be extrapolated that the peak at 5 mM would be ES3. Whatever would be decreasing the binding of ES2 to cobalt whether conformational or charge related as compared to ES would likely be enhanced with the ES3 intermediate. The peak released with 50 mM imidizole and with stronger binding to DEAE could then be the ES form. Holoenzyme by itself may be the remaining form, purified during the first cobalt run, binding less tightly to DEAE due to a higher pI and elute from nickel with 50 mM imidizole. When the mass of the two 50 mM cobalt eluates were compared however there was no significant difference detected. Both corresponded to the weight expected for holoenzyme alone. Unfortunately no reliable mass measurement of the 10 mM eluate was obtained due possibly to precipitation problems with a lower rhPBGD-His protein concentraiton. If a difference of elution characteristics between the different enzyme substrate intermediates is occurring then a likely explanation would be due to the large conformational changes that take place during the course of the reactions From E to ES4 (Jordan P. M. 1994, Wiley, Chichester (Ciba Found Symp 180), p70–96, Louie G. V. et al. 1996, Proteins 25(1): 48–78). The C-terminal His-tag on the third domain of the protein could become partially hidden and rendered sterically less accessible when the reaction proceeds past the ES1 form. A direct interaction between the his-tag and the growing substrate chain would be less likely. At a pH of 8.5 histidines should be in an electron rich unprotonated state and the substrate complex should also be in an electron rich state even though acidic side chains are neutralized by basic amino acids in the catalytic cleft (Jordan P. M. 1994, Wiley, Chichester (Ciba Found Symp 180), p70–96, Louie G. V. et al. 1996, Proteins 25(1): 48–78). Conformational changes in rhPBGD-His occurring during the reaction could conceivably make accessible other charge groups for interaction with the his-tag either on the surface or perhaps the same ones meant for dampening charges from the growing substrate polymer in the cleft.

Equipment and supplies lists are shown in appendix 4 and 5, respectively.

TABLE 16

Protein assay results on DEAE fractions (with BioRad's Protein assay II kit):

| sample | vol (ml) | mM KCl | protein mg/ml | rhPBGD-His mg/ml | mg prot | gel # | well # | pool | protein mg pool |
|---|---|---|---|---|---|---|---|---|---|
| DEAE Load | 380 | 0 | 8.56 | | 3253 | 1 | 2 | | |
| DEAE FT | 380 | 0 | 1.33 | | 505 | 1 | 3 | | |
| DEAE #1 | 16 | 0 | 0.26 | 0.00 | 4 | 1 | 4 | | |
| 2 | 60 | 0 | 0.23 | 0.00 | 14 | 1 | 5 | | |
| 3 | 100 | 0 | 0.044 | 0.00 | 4 | 1 | 6 | | |
| 4 | 215 | 0 | 0.002 | 0.00 | 0 | 1 | 7 | | |
| 5 | 320 | 0 | 0.005 | 0.00 | 2 | 1 | 8 | | |
| 6 | 75 | 50 | 0.11 | 0.00 | 8 | 1 | 9 | | |
| 7 | 100 | 50 | 0.19 | 0.00 | 19 | 1 | 10 | | |
| 8 | 100 | 50 | 0.14 | 0.00 | 14 | 1 | 11 | | |
| 9 | 94 | 50 | 0.61 | 0.31 | 57 | 1 | 12 | 1 | 334 |
| 10 | 100 | 50 | 1.44 | 1.15 | 144 | 2 | 1 | 1 | \| |
| 11 | 38 | 60 | 1.05 | 0.84 | 40 | 2 | 2 | 1 | \| |
| 12 | 135 | 60–70 | 0.69 | 0.48 | 93 | 2 | 3 | 1 | V |
| 13 | 100 | 70 | 0.4 | 0.10 | 40 | 2 | 4 | 2 | 543 |
| 14 | 50 | 80 | 0.43 | 0.09 | 22 | 2 | 5 | 2 | \| |
| 15 | 50 | 80 | 0.96 | 0.34 | 48 | 2 | 6 | 2 | \| |
| 16 | 50 | 80 | 0.98 | 0.49 | 49 | 2 | 7 | 2 | \| |
| 17 | 50 | 80 | 0.57 | 0.29 | 29 | 2 | 8 | 2 | \| |
| 18 | 50 | 80–90 | 0.48 | 0.14 | 24 | 2 | 9 | 2 | \| |
| 19 | 50 | 90 | 0.42 | 0.13 | 21 | 2 | 10 | 2 | \| |
| 20 | 50 | 90 | 0.61 | 0.24 | 31 | 3 | 1 | 2 | \| |
| 21 | 50 | 90–100 | 0.93 | 0.70 | 47 | 3 | 2 | 2 | \| |
| 22 | 50 | 100 | 1.08 | 0.86 | 54 | 3 | 3 | 2 | \| |
| 23 | 50 | 100 | 0.57 | 0.34 | 29 | 3 | 4 | 2 | \| |
| 24 | 50 | 110 | 0.41 | 0.08 | 21 | 3 | 5 | 2 | \| |
| 25 | 50 | 110 | 0.61 | 0.09 | 31 | 3 | 6 | 2 | \| |
| 26 | 50 | 110 | 0.69 | 0.17 | 35 | 3 | 7 | 2 | \| |
| 27 | 50 | 110–120 | 0.73 | 0.44 | 37 | 3 | 8 | 2 | \| |
| 28 | 28 | 120 | 1.07 | 0.86 | 30 | 3 | 9 | 2 | \| |
| 29 | 50 | 120 | 1.08 | 0.76 | 54 | 3 | 10 | 2 | V |

TABLE 17

Second cobalt run fraction with other samples in FIG. 20 gel

| Sample description | Imidizole mM | volume ml | Conc. mg/ml | Total mg | Gel lane | Ico-pure mg |
|---|---|---|---|---|---|---|
| Co-1 load | 0 | 367 | 0.78 | 286.3 | 2 | |
| Co-1 FT | 0 | 367 | 0.22 | 80.7 | 3 | |
| Co-1 Eluate | 50 | 30 | 8.46 | 193.8 | 4 | 193.8 |
| Ml #1 Nickel | 500? | | 9.65 | | 5 | |
| PBGD-1 Lys | 0 | | 1.73 | | 6 | |

TABLE 17-continued

Second cobalt run fraction with other samples in FIG. 20 gel

| Sample description | Imidizole mM | volume ml | Conc. mg/ml | Total mg | Gel lane | Ico-pure mg |
|---|---|---|---|---|---|---|
| Ab prep #1 | 0 | 3.3 | 4.00 | 13.2 | 7 | |
| Cobalt-2 FT | 0 | 900 | 0.23 | 207.0 | 8 | |
| FT tail | 0 | 30 | 0.02 | 0.6 | — | |
| Cobalt-2 w1 | 5 | 100 | 0.01 | 1.0 | — | |
| Cobalt-2 w2 | 5 | 50 | 0.14 | 7.0 | — | |
| Cobalt-2 w3 | 5 | 52 | 0.02 | 1.0 | — | |
| Cobalt-2 w4 | 5 | 100 | 0.04 | 4.0 | — | |
| Cobalt-2 w5 | 10 | 50 | 0.07 | 3.5 | — | |
| Cobalt-2 w6 | 10 | 50 | 0.81 | 40.5 | 9 | |
| Cobalt-2 w7 | 10 | 50 | 0.81 | 40.5 | 10 | 101.5 |
| Cobalt-2 w8 | 10 | 50 | 0.41 | 20.5 | 11 | |
| Cobalt-2 w9 | 10 | 130 | 0.20 | 26.0 | — | |
| Cobalt-2 E1 | 50 | 22.5 | 2.29 | 51.5 | 12 | 51.5 |
| Cobalt-2 E2 | 50 | 30 | 0.11 | 3.3 | — | |
| Total mg highly pure rhPBGD-His (by amino acid analysis) = | | | | | | 346.8 |

TABLE 18 rhPBGD-His amino acid analysis:

| | | | #1 | | #2 | | #3 | | #4 | |
|---|---|---|---|---|---|---|---|---|---|---|
| | | | | | umol/ml→ | | | | | |
| aa | # aa | % whole | aa | [PBGD] | aa | [PBGD] | aa | [PBGD] | aa | [PBGD] |
| Ala | 29 | 8.31 | 4.8220 | 0.166 | 0.5920 | 0.020 | 1.6950 | 0.058 | 4.5406 | 0.157 |
| Arg | 21 | 6.02 | 3.7279 | 0.178 | 0.4550 | 0.022 | 1.3050 | 0.062 | 3.5129 | 0.167 |
| Asn | 10 | 2.87 | | | | | | | | |
| Asp | 19 | 5.44 | 4.7157 | 0.163 | 0.5755 | 0.020 | 1.6510 | 0.056 | 4.4442 | 0.153 |
| Cys | 4 | 1.15 | | | | | | | | |
| Gln | 19 | 5.44 | | | | | | | | |
| Glu | 21 | 6.02 | 6.7648 | 0.169 | 0.8152 | 0.020 | 2.3592 | 0.059 | 6.3524 | 0.159 |
| Gly | 27 | 7.74 | 4.3933 | 0.163 | 0.6120 | 0.023 | 1.5595 | 0.058 | 4.1137 | 0.152 |
| His | 18 | 5.16 | 2.5664 | 0.143 | 0.2539 | 0.014 | 0.7947 | 0.044 | 2.4518 | 0.136 |
| Ile | 20 | 5.73 | 3.0511 | 0.153 | 0.3661 | 0.018 | 1.0561 | 0.053 | 2.8381 | 0.142 |
| Leu | 43 | 12.32 | 7.0235 | 0.163 | 0.8565 | 0.020 | 2.4506 | 0.057 | 6.6020 | 0.154 |
| Lys | 18 | 5.16 | 2.9241 | 0.162 | 0.3538 | 0.020 | 1.0427 | 0.058 | 2.7135 | 0.151 |
| Met | 6 | 1.72 | 0.8691 | 0.145 | 0.0996 | 0.017 | 0.3072 | 0.051 | 0.8252 | 0.138 |
| Phe | 9 | 2.58 | 1.4713 | 0.163 | 0.1825 | 0.020 | 0.5216 | 0.058 | 1.4045 | 0.156 |
| Pro | 16 | 4.58 | 2.7268 | 0.170 | 0.3708 | 0.023 | 1.1194 | 0.070 | 2.8441 | 0.178 |
| Ser | 18 | 5.16 | 2.8356 | 0.158 | 0.3570 | 0.020 | 1.0121 | 0.056 | 2.8680 | 0.159 |
| Thr | 20 | 5.73 | 3.4426 | 0.172 | 0.4272 | 0.021 | 1.2154 | 0.061 | 3.2746 | 0.164 |
| Trp | 2 | 0.57 | | | | | | | | |
| Tyr | 3 | 0.86 | 0.5150 | 0.172 | 0.0626 | 0.021 | 0.1734 | 0.058 | 0.4823 | 0.161 |
| Val | 26 | 7.45 | 4.0526 | 0.156 | 0.4920 | 0.019 | 1.4292 | 0.055 | 3.7740 | 0.145 |
| Avg μmol/mol rhPBGD-His: (w/o bold values) | | | | 0.167 | | 0.021 | | 0.059 | | 0.159 |
| Avg mg/ml rhPBGD-His: (MW = 38759.4) | | | | 6.46 | | 0.81 | | 2.29 | | 6.17 |
| Volume (ml): | | | | 30 | | 100 | | 22.5 | | 5 |
| amount in fraction (mg): | | | | 193.7 | | 80.8 | | 51.6 | | 30.8 |

| sample | run # | imidazole | Notes |
|---|---|---|---|
| #1 | 1 | 50 mM | Major peak of cobalt eluate (from 50→60 mM KCl elution from DEAE) |
| #2 | 2 | 10 mM | 70→120 mM KCl elution from DEAE; cobalt fractions W-6.7 |
| #3 | 2 | 50 mM | 70→120 mM KCl elution from DEAE; fraction E-1 |
| #4 | 1 | — | #1 dialyzed → PBS + 5 mM Tris/Cl pH 8.0 (used for 2nd round Antibodies) |
| | Analysis done at: | | AAA Laboratory |
| | By: | | Lowell Ericsson, Nancy Ericsson |
| | Address: | | 6206 89th Ave SE, Mercer Island, Washington 98040-4599 |

COMBINATION THERAPY

Combination therapy of rhALAD AND rhPBGD

The etiology behind AIP is not fully understood. However, the accumulation of the two heme-precursors delta-aminolevulinic acid (ALA) and porphobilinogen (PBG) are likely to be involved. ALA and PBG have been suggested to be toxic to the central and peripheral nervous system causing the well known symptoms such as abdominal pain, muscle weakness, loss of sensory functions as well as epileptic seizures, respiratory paralysis, hallucinations and psychosis, observed during acute attacks.

The rationale for the enzyme substitution therapy in AIP patients is based on the administration of rhPBGD by sc. injections to lower serum and intracellular PBG levels. PBG will be metabolized to preurophorphyrinogen. Preuroporphyrinogen will subsequently enter the normal heme biosynthetic pathway and be metabolized to heme. Hence, rhPBGD enzyme replacement therapy will have a dual action, i) reduce circulating levels of toxic PBG and ii) restore heme production.

In the etiology of the disease it has always been suggested that ALA might have an even more toxic effect that PBG. Hence, a reduction of both ALA and PBG is important to achieve. Treatment of AIP patients with rhPBGD will i) reduce circulating levels of PBG as well as ALA, since ALA and PBG are in equilibrium with each other through coupled enzyme reactions e.g. deta-aminolevulinic acid dehydratase (ALAD) and porphobilinogen deaminase PBGD and ii) restore heme production. A block in the PBGD enzyme will result in the accumulation of both PBG and ALA. Administration of rhPBGD will quickly metabolise PBG and lower ALA levels as well, through changes in the equilibrium of the ALAD enzyme reaction.

An accelerated reduction of ALA might be beneficial to AIP patients. Hence, a coadministration of both rhPBGD and rhALAD will rapidly reduce both heme precursors. The mixing and administration of rhALAD and rhPBGD could be done in two ways, either: i) a product containing both enzymes at fixed proportions or ii) administration of rhPBGD and rhALAD by two separate subcutaneous injections. In the latter case the dose of the two enzymes could be adjusted to obtain optimal individual therapy. Administration of separate enzymes provides also a possibility for optimal temporal order of administration to obtain the best individual therapeutic effect.

Combination therapy of rhPBGD and rhUroporphyrinogen III cosynthetase

Coadministration of rhPBGD and rhUroporphyrinogen III cosynthetase to some AIP patients are likely to be beneficial, by improving conversion of preuroporphyrinogen to its uroporphyrinogen III isomer rather than the I isomer. The I isomer forms spontaneously from preuroporphyrinogen and can not be further metabolised into heme. Hence, a coadministration of rhPBGD and Uroporphyrinogen III cosynthetase will ensure a better restoration of normal heme synthesis in that less amount of the uroporphyrinogen I isomer will be formed.

Combination therapy of rhALAD, rhPBGD and rhUroporphyrinogenIIIcosynthetase rhPBGDcosynthetase can be coadministered with both rhPBGD and rhALAD to specific patients to obtain beneficial heme synthesis restoration.

It is within the scope of the present invention to extend a combination therapy to other enzymes mentioned herein and to treatment of the other porphyias.

TREATMENT OF OTHER PORPHYRIAS

In analogy with the new treatment of AIP patients with (recombinant) PBGD, hepatic Porphyrias such as ALA deficiency Porphyria (ADP), Porphyria cutanea tarda (PCT), Hereditary Coproporphyria (HCP) and Variegata Porphyria (VP) can benefit from substitution therapy by rhALA dehydratase, rhUroporphyrinogen decarboxylase, rhCoproporphyrinogen oxidase and rhProtoporphyrinogen oxidase, respectively.

Patients having Erythropoetic Porphyrias such as Congenital erythropoietic Porphyria (CEP) or Erythropoietic protoporphyria (EPP) will benefit from substitution therapy with rhUroporphyrinogen III synthetase and rhFerrochelatase, respectively.

Hepatoerythropoietic Porphyrias e.g. Hepatoerythropoietic Porphyrias (HEP) can be treated with rhUroporphyrinogen decarboxylase.

All porphyrias can be treated by the administration of the enzymatic activity lacking or being reduced (normally 50%) in any of the eight steps in the heme biosynthetic pathway as described above.

The substitution of the enzymatic activity can be achieved by adding the corresponding recombinant enzyme or other molecules that will provide the missing enzymatic activity. In situations where a combination of enzymes are beneficial, such therapy may be applied in a manner similar as disclosed above.

REFERENCES

Anderson P. M. and R. J. Desnick. 1979, Purification and Properties of Uroporphyrinogen I Synthase from Human Erythrocytes: Identification of Stable Enzyme-Substrate Intermediates The Journal of Biological Chemistry 255 (5):1993–99

Andersson, Christer, Thesis, 1997, ISBN 91/7191/280/0, pp. 22–23

Amann, E., Brosius, J., and Ptashne, M. 1988, Vectors bearing a hybrid trp-lac promoter useful for regulated expression of cloned genes in Escherichia coli. Gene 25(2–3):167–178

Awan S. J. et al. 1997, Reconstitution of the Holoenzyme Form of E. coli Porphobilinogen Deaminase from Apoenzyme with Porphobilinogen and Preuroporphyrinogen: A Study Using Circular Dichroism Spectroscopy Biochemistry 36 (30):9273–82

Gold, L. and Stormo, G. D. 1990, High-level translation initiation. Methods Enzymol. 185:89–93:89–93

Grandchamp B. et al. 1987, Tissue-specific expression of porphobilinogen deaminase. Two isoenzymes from a single gene. Eur J Biochem. Jan;162(1):105–10

Grandschamp B. et al. 1996, J. of Gastroenerology and Hepatology 11, 1046–1052

Herrick A. L. et al. 1989, Lancet 1, 1295–1297

Jeans J. et al. 1996, American J. of Medical Genetics, 65, 269–273

Jordan P. M., S. D. Thomas and M. J. Warren. 1988, Purification, crystallization and properties of porphobilinogen deaminase from a recombinant strain of Escherichia coli K12. Biochem. J. 254: 427–435

Jordan, P. M. The biosynthesis of uroporphyrinogen III: mechanism of action of porphobilinogen deaminase. In: The biosynthesis of the tetrapyrrole pigments 1994 Wiley, Chister (Ciba Found Symp 180), p70–96

Lambert R. et al. 1994, Structural studies on porphobilinogen deaminase. In: The biosynthesis of the tetrapyrrole pigments. Wiley, Chichester (Ciba Found Symp 180), p97–110

Lewis, L. A., Li, K. B., Gousse, A., Pereira, F., Pacheco, N., Pierre, S., Kodaman, P., and Lawson, S. 1991, Genetic and molecular analysis of spontaneous respiratory deficient (res-) mutants of Escherichia coli K-12. Microbiol. Immunol. 35(4):289–301

Lithner F. et al. 1984, Acta.Med.Scand. 215, 271–274

Louie, G. V. et al. 1996, The three-dimensional structure of Escherichia coli porphobilinogen deaminase at 1.76-A resolution Proteins 25(1):48–78

Makrides, S. C. 1996, Strategies for achieving high-level expression of genes in Escherichia coli. Microbiiol.Rev. 60(3):512–538

Maniatis T., E. F. Fritsch, J. Sambrook. Molecular Cloning (A laboratory Manual) Cold Spring Harbor Laboratory. 1982

Miller et al. 1989, Bio Techniques 7, 980–990

Miyagi K. et al. 1979, Uroporphyrinogen I synthase from human erythrocytes: Separation, purification, and properties of isoenzymes. Proc. Natl. Acad. Sci. 76:12 6172–76

Morrison D. A. 1979, Transformation and preservation of competent bacterial cells by freezing. *Methods Enzymol.* 68, 326–331.

Mustajoki et al. 1989, Sem. Hematol. 26, 1–9

Raich N. et al. 1986, Molecular cloning and complete primary sequence of erythrocyte porphobilinogen deaminase. Nucleic Acids Research 14(15):5955–67

Raich N. et al. 1986, Nucleic. Acid. Res, 14, 5955–5968

Saiki R. K. et al. 1985, Enzymatic amplification of beta-globin genomic sequences and restriction site analysis for diagnosis of sickle cell anemia. Science, 20;230(4732):1350–4.

Sassa S. 1996, Blood Review, 10, 53–58

Shoolingin-Jordan P. M., M. J. Warren and S. J. Awan, 1997, Dipyrromethane Cofactor Assembly of Porphobilinogen Deaminase: Formation of Apoenzyme and Preparation of Holoenzyme. Methods in Enzymology 281:317–327

Stephens P. E. et. al. Biochem J. 248, 1–11, 1987

Strand et al. 1970, Proc. Natl. Acad. Sci. 67, 1315–1320

Tishler P. V. et al. 1985, Am.J.Psychiatry 142, 1430–1436

Waldenström J. 1937, Acta.Med. Scand. Suppl.82

Welland F. H. et al. 1964, Metabolism, 13, 232

Wetterberg L. 1967, Svenska bokförlaget Nordstedt, Stockholm

Wetterberg L. 1976, In Doss M. Nowrocki P. eds. Porphyrias in Human Disease. Reports of the discussion. Matgurg an der Lahn, 191–202

Yeung L. et al. 1983, Q J. Med 52, 92–98

Yoo H. W. et al. 1993, Hydroxymethylbilane synthase: complete genomic sequence and amplifiable polymorphisms in the human gene. Genomics Jan; 15(1):21–9

APPENDICES

APPENDIX 1

Equipment list

| Item | Manufacturer | Ser. No. |
|---|---|---|
| Pipetman-P-1000 | Gilson | N55287E |
| Pipetman-P-200 | Gilson | N52324E |
| Pipetman-P-20 | Gilson | N53465M |
| Pipetman-P-10 | Gilson | P626586 |
| 5415C centrifuge | Eppendorf | 5415B68381 |
| GS-6KR centrifuge | Beckman | NGD97J18 |
| Avanti J-25 I centrifuge | Beckman | JJY97J14 |
| DU 640B Spectrophotometer | Beckman | 4323015 |
| Genie II vortex | VWR | 2-241186 |
| GeneAmp PCR system 2400 | Perkin Elmer (PE)/Applied Biosystem (ABI) | 803N6021903 |
| GeneAmp PCR system 2400 | PE/ABI | 803S7100104 |
| GeneAmp PCR system 9700 | PE/ABI | 805S7121566 |
| 1545 incubator | VWR | 0902597 |
| heat block 1 | VWR | 0795 |
| heat block 1 | VWR | 0511 |
| Gene Pulser II Apparatus | BioRad | 340BR2745 |
| Pulse Controller Plus | BioRad | 339BR1377 |
| Power Pac 1000 | BioRad | 286BR00770 |
| Sub Cell | BioRad | 16S/8860 |
| Wide-Mini Sub Cell | BioRad | 02S/7951 |
| Foto/Prep trans-illuminator | Fotodyne | PTG1-0997-2831 |
| Elutrap Electro-separator | Schleicher + Schuell | Order No. 57880 |
| Innova 4000 incubator | New Brunswick Scientific | 890165366 |

APPENDIX 1-continued

Equipment list

| Item | Manufacturer | Ser. No. |
|---|---|---|
| Power Mac G3 computer | Macintosh | XA8061A3BBW |
| Trinitron Multiscan 200GS monitor | Sony | 8057052 |
| DNA analysis Software: Geneworks | Intelligenetics | Version 2.5.1 |

APPENDIX 2

Supplies List

| Item | Supplier | Cat No. | Lot No. |
|---|---|---|---|
| Human Spleen Poly A + RNA | Clontech | 6542-1 | 7120266 |
| Human Bone Marrow Poly A + RNA | Clontech | 6573-1 | 56714 |
| Human Lung Poly A + RNA | Clontech | 6524-1 | 7050104 |
| Human Lymph Node Poly A + RNA | Clontech | 6594-1 | 6120292 |
| Human Brain Poly A + RNA | Clontech | 6516-1 | 63101 |
| Human Adipose Total RNA | Clontech | D6005-01 | 7907005 |
| Superscript II reverse transcriptase | Gibco/BRL | 18064-014 | JM6418 |
| 100 mM dNTP set | Pharmacia | 27-2035-01 | 6072035011 |
| pBluescriptII SK-phagemid | Stratagene | 212206 | 0270702 |
| Advantage cDNA polymerase mix | Clontech | 8417-1 | 8060354 |
| GeneAmp dNTP | PE/ABI | N-808-0007 | H0172.4, H0553 |
| Xba-I endonuclease | New England Biolabs (NEB) | 145S | 30 |
| Pvu-II endonuclease | NEB | 151L | 14 |
| EcoR-I endo-nuclease | NEB | 101L | 25 |
| Hind-III endo-nuclease | NEB | 104S | 49 |
| Tris six-Pack "C" | Sigma | T-PAC-C | 77H9049 |
| 0.5M EDTA pH 8.0 | Sigma | E-7889 | 16H8924 |
| Chromaspin TE 400 | Clontech | K1323-1 | 7090795 |
| Chromaspin 400 DepC dH$_2$O | Clontech | K1333-1 | 7040086 |
| Quiaquick gel extraction kit | Qiagen | 28704 | BY97017/0397/119 |
| Microcon-30 | Amicon | 42410 | L8JM4330B |
| Microcon-100 | Amicon | 42413 | L8DM3296A |
| Micropure 0.22 µm | Amicon | 42544 | CCB017 |
| Seakem GTG agarose | FMC | 50074 | 709397 |
| 100 bp DNA Ladder | NEB | 323-1 | 3 |
| 123 bp DNA Ladder | Gibco/BRL | 15613-029 | JK9706 |
| T4 DNA Ligase | NEB | 202S | 64 |
| Ampicillin | Sigma | A-9518 | 76H0434 |
| LB media | Gibco/BRL | 12795-084 | 12E1072B |
| Bacto Agar | Difco | 0140-07-4 | 106728JA |
| DH10B electromax | Gibco/BRL | 18290-015 | KHN430 |
| SOC media | Gibco/BRL | 15544-042 | 1010351 |
| Taq polymerase | Fisher | FB-6000-15 | H0436 |
| TaqStart antibody | Clontech | 5400-1 | 6070479 |
| Qiafilter Midi DNA isolation kit | Qiagen | 12243 | PO No. 514 |
| Isopropanol | Sigma | I-9516 | 47H3724 |
| Big Dye terminator cycle sequencing kit | PE/ABI | 4303152 | 9803008 |

Appendix 3

Media, Strains and Transformation:

LB media (Bacto LB broth, Miller et al. 1989, Bio Techniques 7, 980–990, from Difco, Catalogue #0446007-5) was used as the basic growth media throughout the course of this study. The antibiotics ampicillin (Sigma, Catalogue # A9518), tetracycline (Sigma, Catalogue # T-3383), chloramphenical (Sigma, Catalogue # C-1919) and G-418 (Gibco/BRL, Catalogue # 11811-015) were used at concentrations of 150 µg/ml, 12 µg/ml, 25 µg/ml and 12 µg/ml, respectively. Wherever indicated, glucose (Sigma, Catalogue # G-5400) was added at 0.2% and hemin (Sigma, Catalogue # H-2258) at 50 µg/ml. The stock solution for hemin was 50 mg/ml in 0.1M NaOH. The composition of M9 medium was from Maniatis T., E. F. Fritsch, J. Sambrook. Molecular Cloning (A laboratory Manual) Cold Spring Harbor Laboratory. 1982. It was supplemented with 1 mM $MgSO_4$ and 1 g/ml thiamine hydrochloride. For all solid media, Bacto Agar (Difco, Catalogue # 0140-07-4) was used at a concentration of 1.5%.

The ligation mixes for constructing plasmids pExp0, pPBGD1,1 and pExp1 were transformed in to DH12S (Gibco/BRL, Catalogue # 18312-017). For the plasmids pExp1-M2 and pExp1-M2-BB strain JM105 was used. For all steps leading to the construction of the plasmid phemCdCm (used as the source of the EcoR I-Hind III linear fragment for hemC disruption) strain DH10B cells (Gibco/BRL, Catalogue # 18290-015) were used. Transformation into DH12S or DH10B was by electroporation using a BioRad electroporator at 2.0 Kv/200 Ohms/25 mF in 0.1 cm cuvets. Transformations into JM105 and all it derivatives and JM110 was done using $CaCl_2$ (Morrison D. A 1979, *Methods Enzymol.* 68, 326–331).

Enzyme Assays:

All enzyme assays were performed as described in example 3 under the subtitle "PBGD Activity Assay". The cultures were grown in LB+ampicillin under the conditions of temperature and induction as described in the report. The final densities of harvest ranged between 0.8 and 1.3 OD units at $A_{600}$. For activity determinations, cells were spun down from 1 ml samples and frozen at −20° C. The thawed cell pellets were resuspended in about 100 µl of B-PER reagent (PIERCE, Catalogue # 78243), incubation at room temperature for 10 minutes, spun at 16,000 for 10 minutes and PBGD activity was determined in the supernatants. Total protein was estimated by the Bradford method using the BioRad reagent (Catalogue # 500-0006) and bovine serum albumin as stsndard.

Molecular Biology Supplies:

All restriction endonucleases and T4 DNA ligase purchased from New England Biolabs, the kit for PCR reactions from Clonetech (Catalogue # 8417-1) and the kit for DNA sequencing for the Big Dye terminator cycle sequencing from PE/ABI (Catalogue # 4303152). Plasmid DNAs were made using either the RPM AFS Kit (BIO 101, Catalogue # 2072-200), the RPM SPIN Midi Kit (BIO 101, Catalogue # 2005-200) or the RMP-1G Kit (BIO 101, Catalogue # 2077-000). DNA was extracted from agarose gel slices with GENECLEAN III (BIO 101, Catalogue # 1001-600), GENECLAN Spin Kit (BIO 101, Catalogue # 1101-000) or Quiaquick gel extraction kit (Qiagen, Catalogue # 28704).

APPENDIX 4

Equipment list:

| Item | Manufacturer | Serial Number |
| --- | --- | --- |
| Pipetman P-1000 | Gilson | N55287E |
| Pipetman P-200 | Gilson | N52324E |
| Pipetman P-20 | Gilson | N53465M |
| Pipetman P-10 | Gilson | P626586 |
| 5415C centrifuge | Eppendorf | 5415B68381 |
| GS-6KR centrifuge | Beckman | NGD97J18 |
| Avanti J-25 I centrifuge | Beckman | JJY97J14 |
| DU 640B Spectrophotometer | Beckman | 4323015 |
| Genie II vortex | VWR | 2-241186 |
| GeneAmp PCR system 2400 | Perkin Elmer (PE)/ Applied Biosystems (ABI) | 803N6021903 |
| GeneAmp PCR system 2400 | PE/ABI | 803S7100104 |
| GeneAmp PCR system 9700 | PE/ABI | 805S7121566 |
| 1545 incubator | VWR | 0902597 |
| BioTek FL-600 plate reader | BioTek | |
| ProTeam LC System 210 | ISCO | |
| Nupage Electrophoresis System | NOVEX | |
| Gel Destainer | BioRad | |
| Power Pac 200 | BioRad | |
| Power Pac 1000 | BioRad | |
| Innova 4000 incubator | New Brunswick Scientific | 890165366 |
| Innova 4000 incubator | New Brunswick Scientific | |
| Power Mac G3 computer | Macintosh | XA8061A3BBW |
| Trinitron Multiscan 200GS monitor | Sony | 8057052 |
| DNA analysis Software: Geneworks | Intelligenetics | Version 2.5.1 |
| Sonifier 450 | Branson | |
| ½" diameter stepped disruptor horn | Branson | |
| 2.5 × 50 cm LC column | Spectrum | |
| 1.5 × 30 cm LC column | Spectrum | |

APPENDIX 5

Supplies List

| Item | Supplier | Cat # | Lot # |
| --- | --- | --- | --- |
| Ampicillin | Sigma | A-9518 | 76H0434 |
| Bacto Agar | Difco | 0140-0704 | 106728JA |
| Tris six-pack "C" | Sigma | T-PAC-C | 77H9049 |
| Trizma Base | Sigma | T-8524 | 28H5436 |
| HCl | Sigma | H-1758 | 37H3495 |
| PBG (5 mg) | Sigma | P-1134 | 77H0930 |
| PBG (1 mg) | Sigma | P-1134 | 36H1297 |
| BSA (fraction 5) | Sigma | A-6003 | 87H7603 |
| DTT | Sigma | D-9779 | 105H7711 |
| Methanol | Fisher | A452SK-4 | 982215 |
| P-Benzoquinone | Acros | 10563-0050 | A011202801 |
| DEAE Sepharose Fast Flow | Pharmacia | 17-0709-01 | 256288 |
| Chelating Sepharose Fast Flow | Pharmacia | 17-0575-01 | 253865 |
| Nickel Sulfate | Sigma | N73-100 | 985482 |
| Talon Superflow Metal Affinity Resin | Clontech | 8908-2 | 8110601 |
| Centricon Plus-80 (Biomax 8) | Millipore | UFC5 BFC 02 | Not available |
| Nupage 10% Bis/Tris gels | Novex | NP0302 | Various |
| Protein Assay Kit II | BioRad | 500-0002 | 59163A, 62171A |
| Centricon-10 | Millipore | 4321 | L8PM2042 |
| KCl | Sigma | P-9333 | 68H01001 |
| NaCl | Sigma | S-3014 | 97H1151 |

APPENDIX 5-continued

Supplies List

| Item | Supplier | Cat # | Lot # |
| --- | --- | --- | --- |
| Imidizole | Fisher | 03196-500 | 985421 |
| Corning microtiter plate | Fisher | 07-200-89 | Not available |
| Costar 96 well × 2 ml plate | Fisher | 097-61-117 | Not available |
| MicroAmp Reaction Tubes | Perkin Elmer | N801-0838 | S18N8-41 |
| MicroAmp Full Plate Cover | Perkin Elmer | N801-0550 | 090397 |
| Spectra/Por 2.1 Biotech Dispo-Dialyzers MWCO: 15k | Spectrum | 135030 | 11987 |
| Bacto LB broth, Miller | Difco | 0446007-5 | 133116JC |
| Bacto Yeast Extract | Difco | 0127-17-9 | 132389JC |
| Bacto Tryptone | Difco | 0123-17 | 135850XA |
| Nalgene 0.22 µm filter 500 ml | Fisher | 169-0020 | Not available |
| Nalgene 0.22 µm filter 250 ml | Fisher | 168-0020 | Not available |
| Millipore Durapore Filter | Fisher | SCGF-U05RE | Not available |

We claim:

1. The expression plasmid pExp1-M2-BB as shown in Seq. ID NO 1.

2. The DNA fragment of Seq. ID NO 2, capable of obtaining hemC-deletion in a host.

3. The rhPBGD production strain (DSM Accession No. 12915) obtained by use of the DNA fragment, EcoR I-Hind III linear fragment as shown in Seq. ID NO 2 to obtain hemC-deletion in the host JM105-H-R6-C by homologous gene replacement and transforming the resulting strain with the expression plasmid pExp1-M2-Bb to yield the final production strain which is free from production of PBGD of non human origin.

4. A method for the preparation of a protein comprising the amino acid sequence of a human porphobilinogen deaminase (PBGD) by a method comprising a) providing a transformed host cell transformed with a recombinant DNA molecule which is a vector comprising a nucleic acid sequence encoding an expression product comprising the amino acid sequence of a human PBGD;

b) culturing the transformed host cell under conditions facilitating expression of the nucleic acid sequence; and c) recovering the expression product, where said human PBGD comprises an amino acid sequence encoded by a nucleotide sequence selected from the group consisting of SEQ ID NOs:3–11.

5. The method according to claim 4 further comprising a fermentation step.

6. The method according to claim 4 further comprising a purification step.

7. The method according to claim 6 wherein the purification is performed with a His-Tag and the expression product is a fusion protein (rhPBGD-His) comprising a human PBGD and a His-Tag.

8. The method of claim 4 in which the human PBGD is the allelic form of human PBGD encoded by clone PBGD1.1 (SEQ ID NO:3).

9. The method of claim 8 in which the expression product is a fusion protein consisting of a human PBGD and a His-Tag.

10. The method of claim 4 in which the transformed cell does not produce a nonhuman PBGD.

11. The method of claim 10 in which the transformed cell is an *E. coli* cell from which the hemC gene has been deleted.

12. The method of claim 4 in which the expression product is a fusion protein consisting of a human PBGD and a His-Tag.

13. The method of claim 4 where said human PBGD consists of an amino acid sequence encoded by a nucleotide sequence selected from the group consisting of SEQ ID NOs:3–11.

* * * * *